United States Patent
Montgomery

(10) Patent No.: US 6,444,111 B1
(45) Date of Patent: *Sep. 3, 2002

(54) ELECTROCHEMICAL SOLID PHASE SYNTHESIS OF POLYMERS

(75) Inventor: Donald D. Montgomery, Millbrae, CA (US)

(73) Assignee: CombiMatrix Corporation, Mulkilteo, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/416,860

(22) Filed: Oct. 13, 1999

Related U.S. Application Data

(63) Continuation of application No. 09/003,075, filed as application No. PCT/US97/11463 on Jul. 3, 1997, now Pat. No. 6,093,302.
(60) Provisional application No. 60/021,002, filed on Jul. 5, 1996.

(51) Int. Cl.[7] .............. C25B 1/00; C25B 3/00; C25C 1/00; C25C 3/00; C25C 3/08
(52) U.S. Cl. .......... 205/334; 205/687; 205/688
(58) Field of Search ............... 205/334, 418, 205/687

(56) References Cited

U.S. PATENT DOCUMENTS

| | | | | |
|---|---|---|---|---|
| 4,280,885 A | * | 7/1981 | Savery | 204/129 |
| 5,364,851 A | * | 11/1994 | Joran | 530/345 |
| 5,405,766 A | * | 4/1995 | Kallury et al. | 435/174 |
| 5,510,481 A | * | 4/1996 | Bednarski et al. | 536/120 |
| 5,667,667 A | * | 9/1997 | Southern | 205/687 |
| 5,798,035 A | * | 8/1998 | Kirk et al. | 205/335 |
| 5,824,470 A | * | 10/1998 | Baldeschwieler et al. | 435/6 |
| 5,837,859 A | * | 11/1998 | Teoule et al. | 536/25.3 |
| 5,929,208 A | * | 7/1999 | Heller et al. | 530/333 |
| 5,952,172 A | * | 9/1999 | Meade et al. | 435/6 |
| 6,086,748 A | * | 7/2000 | Durst et al. | 205/775 |

* cited by examiner

Primary Examiner—Donald R. Valentine
Assistant Examiner—Erica Smith-Hicks
(74) Attorney, Agent, or Firm—Albert P. Halluin; Adam K. Whiting; Howrey Simon Arnold & White

(57) ABSTRACT

A solid phase synthesis method for the preparation of diverse sequences of separate polymers or nucleic acid sequences using electrochemical placement of monomers of nucleic acids at a specific location on a substrate containing at least one electrode that is preferably in contact with a buffering or scavenging solution to prevent chemical crosstalk between electrodes due to diffusion of electrochemically generated reagents.

44 Claims, 39 Drawing Sheets

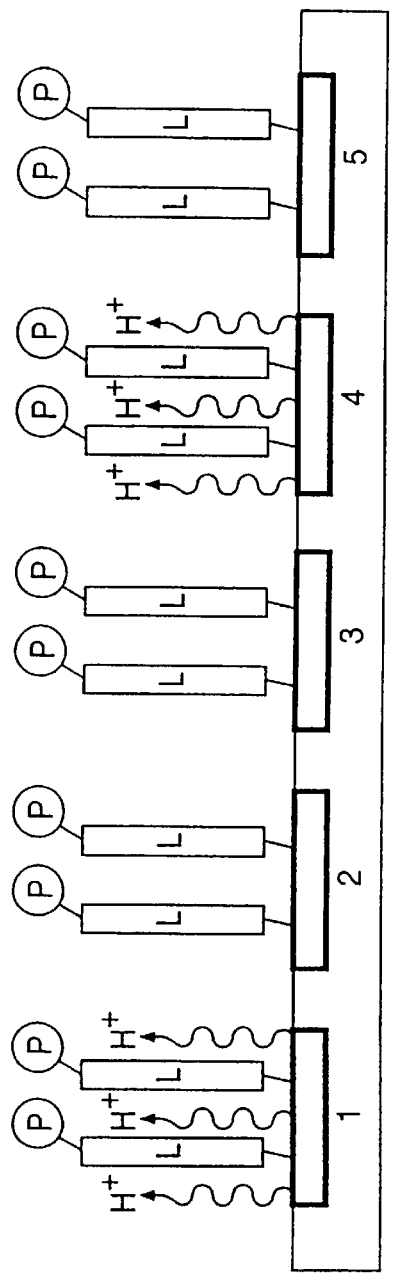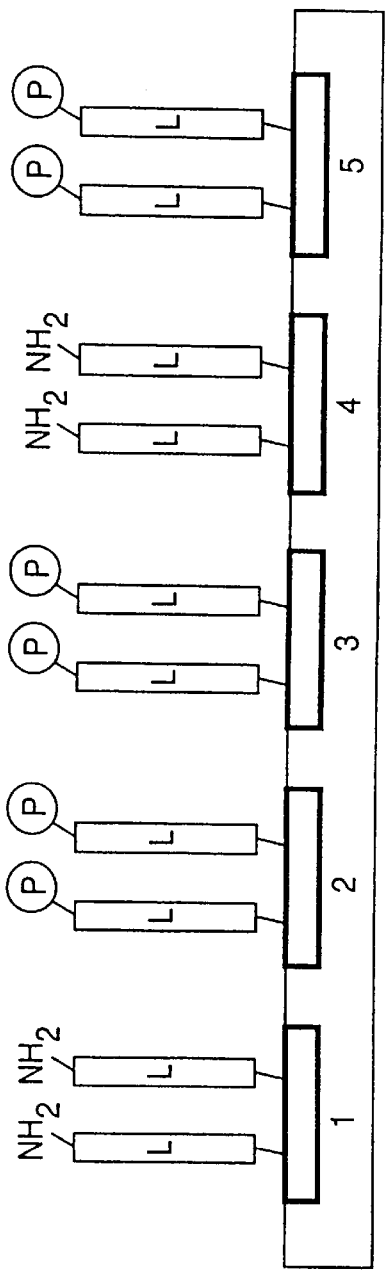

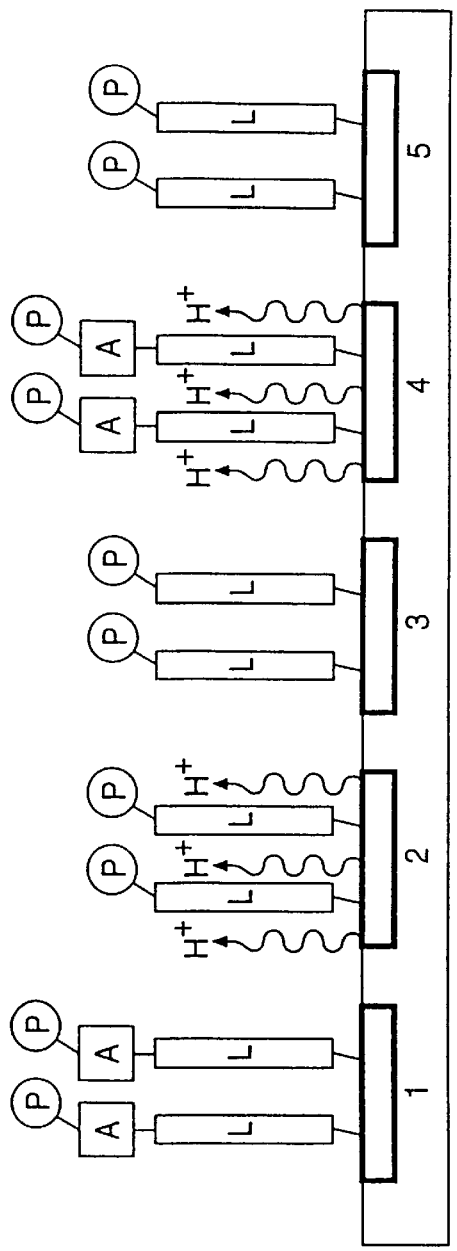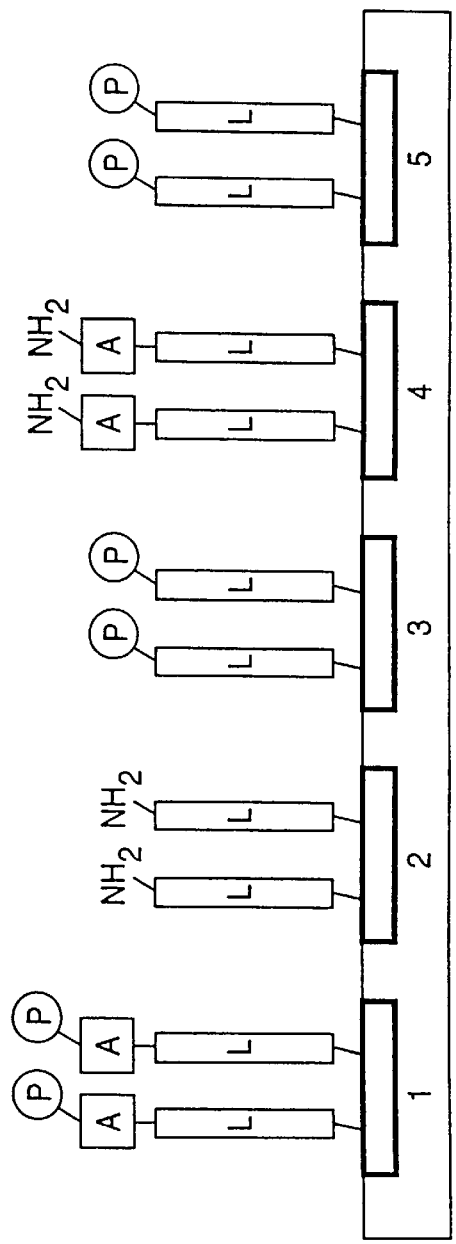
FIG. 3a
FIG. 3b

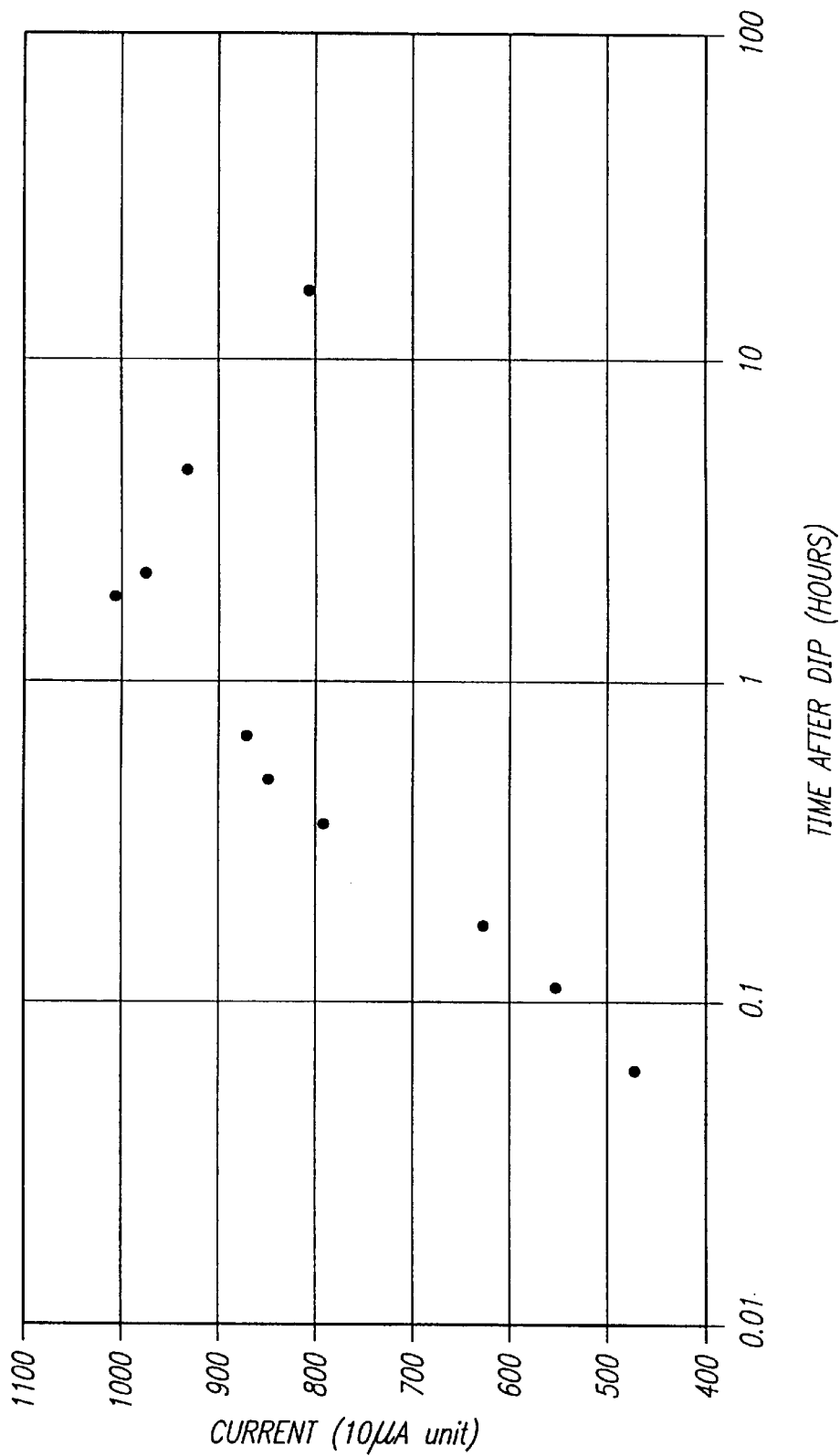

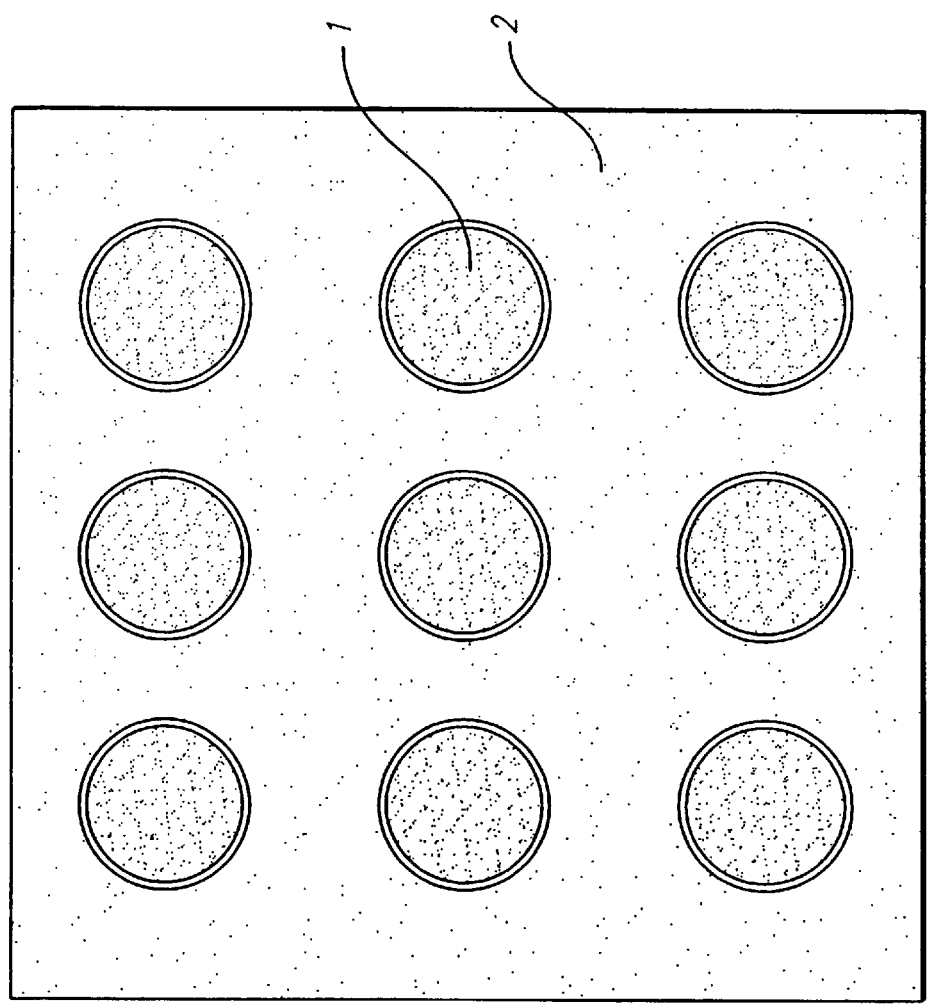
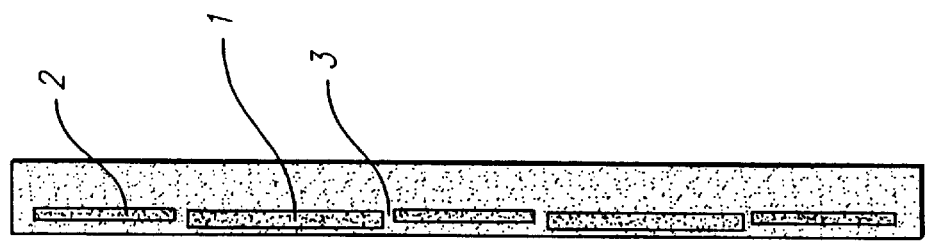
FIG. 34a
FIG. 34b

ELECTROCHEMICAL SOLID PHASE SYNTHESIS OF POLYMERS

The present application is a continuation of U.S. Ser. No. 09/003,075, filed Jan. 5, 1998 now U.S. Pat. No. 6,093,302 which is a 371 of PCT/US97/11463, filed Jul. 3, 1997 and claims benefit of provisional application No. 60/021,802, filed Jul. 5, 1996.

FIELD OF THE INVENTION

The present invention is directed to the synthesis and placement of materials at select locations on a substrate. In particular, the present invention is directed to a method for providing separate sequences of chemical monomers at select locations on a substrate.

The present invention may be applied in the field of, but is not limited to, the preparation of peptide, oligomer, polymer, oligosaccharide, nucleic acid, ribonucleic acid, porphyrin, and drug congeners. In particular, the present invention may be used as a method to create sources of chemical diversity for use in screening for biological activity, for example, for use in the rapidly developing field of combinatorial chemistry.

BACKGROUND OF THE INVENTION

There are many known assays for measuring the binding capabilities of known target molecules and the various molecules known to bind selectively to target molecules, i.e., ligands. The information that may be gained from such experiments often is limited by the number and type of ligands that are available. Continuing research is focused on the discovery of new ligands. Novel ligands are sometimes discovered by chance, or by application of techniques for the elucidation of molecular structure, or by systematic analysis of the relationships between molecular structure and binding activity.

Small peptide molecules are useful model systems for exploring the relationship between structure and function in biology. A peptide is a sequence of amino acids. For example, the twenty naturally occurring amino acids can be condensed into polymeric molecules. These polymeric molecules form a large variety of three-dimensional spatial and electronic structures. Each structure arises from a particular amino acid sequence and solvent condition. The number of possible hexapeptides of the twenty naturally occurring amino acids, for example is $20^6$, or 64 million different peptides. As shown by epitope studies, the small peptide molecules are useful in target-binding studies, and sequences as short as a few amino acids are recognized with high specificity by some antibodies.

The process of discovering ligands with desirable patterns of specificity for targets of biological importance is central to many contemporary approaches to drug discovery. These approaches, based on structure-activity relationships, involve rational design of ligands and large scale screening of families of potential ligands. Often, a combination of approaches is used. The ligands are often, but not exclusively, small peptide molecules.

Yet methods of preparing large numbers of different ligands have been painstakingly slow and prohibitively expensive when used as a scale sufficient to permit effective rational or random screening. For example, the well-known "Merrifield" method (*J. Am. Chem. Soc.* (1963) 85:2149–2154), which is incorporated herein by reference, has been used to synthesize peptides on solid supports. In the Merrifield method, an amino acid is bound covalently to a support made of an insoluble polymer. Another amino acid with an alpha protected group is reacted with the covalently bonded amino acid to form a dipeptide. After washing, the protective group is removed and a third amino acid with an alpha protective group is added to the dipeptide. This process is continued until a peptide of a desired length and sequence is obtained. Using the Merrifield method, synthesis of more than a handful of peptide sequences in a day is not technically feasible or economically practical.

To synthesize larger numbers of polymer sequences, it has been proposed to use a series of reaction vessels for polymer synthesis. For example, a tubular reactor system may be used to synthesize a linear polymer on a solid phase support by automated sequential addition of reagents. This method, however, also does not enable the synthesis of a sufficiently large number of polymer sequences for effective and economical screening.

Another method of preparing a plurality of polymer sequences uses a porous container enclosing a known quantity of reactive particles, larger in size than pores of the container. The particles in the containers may be selectively reacted with desired materials to synthesize desired sequences of product molecules. However, as with the other methods know in the art, this method is not practical for the synthesis of a sufficient variety of polypeptides for effective screening.

Other techniques have also been described and attempted. Several of these methods include synthesis of peptides on 96 plastic pins that fit the format of standard microtiter plates. Unfortunately, while these techniques have been somewhat useful, substantial problems remain. For example, methods using standard microtiter plates continue to be limited in the diversity of sequences that can be synthesized and screened. Although it is recognized that using microtiter plates produces essentially pure polymers because each polymer is synthesized in an isolated well of the microtiter plate, the number of polymers that can be produced in any given time is limited by the number of wells in a microtiter plate, i.e., 96. Moreover, the equipment needed for synthesis in the microtiter plates is large. Because of this limitation, use of microtiter plates requires a large amount of space to produce a relatively small number of peptides.

One attempt at synthesizing a large number of diverse arrays of polypeptides and polymers in a smaller space is found in U.S. Pat. No. 5,143,854 granted to Pirrung et al. (1992). This patent describes the use of photolithogrpic techniques for the solid phase synthesis of arrays of polypeptides and polymers. The disclosed technique uses "photomasks" and photolabile protecting groups for protecting the underlying functional group. Each step of the process requires the use of a different photomask to control which regions are exposed to light and thus deprotected. The necessity of having to fabricate a new set of photomasks for each array of chemical monomers results in a method that is extremely expensive and not well-suited to automation. Moreover, this method is tedious and time consuming because each step of the synthesis requires the mechanical removal, replacement and realignment of a photomask. Thus, synthesizing a large number of libraries of polymers with the Pirrung method is an inefficient and uneconomical process.

Another drawback of the Pirrung method is that the photolabile protecting groups used cannot be removed as effectively as conventional acid or base labile protecting groups can be removed and are plagued by contamination due to undesired side reactions. Consequently, using Pirrung's method, the purity of the chemical array is often compromised due to incomplete removal of the protecting groups and subsequent failure of the underlying functional groups to react with the desired monomer, as well as contamination from undesired side reactions.

Another attempt to synthesize large numbers of polymers is disclosed by Southern in International patent application WO 93/22480, published Nov. 11, 1993. Southern describes a method for synthesizing polymers at selected sites by electrochemically modifying a surface; this method involves providing an electrolyte overlaying the surface and an array of electrodes adjacent to the surface. In each step of Southern's synthesis process, an array of electrodes is mechanically placed adjacent the points of synthesis, and a voltage is applied that is sufficient to produce electrochemical regents at the electrode. The electrochemical reagents are deposited on the surface themselves or are allowed to react with another species, found either in the electrolyte or on the surface, in order to deposit or to modify a substance at the desired points of synthesis. The array of electrodes is then mechanically removed and the surface is subsequently contacted with selected monomers. For subsequent reactions, the array of electrodes is again mechanically placed adjacent the surface and a subsequent set of selected electrodes activated.

This method requires that a large amount of control be exercised over the distance that exists between the electrode array and the surface where synthesis occurs. Control over the distance between the electrodes and the surface for modification is required to ensure precise alignment between the electrodes and the points of synthesis and to limit the extent of diffusion of electrochemically generated reagents away from the desired points of synthesis. However, the inherent difficulty in positioning electrodes repeatedly and accurately within a few microns of the surface frequently results in the production of electrochemically generated reagents at undesirable synthesis points. Moreover, the diffusion of the electrochemically generated reagents from desired sites of reaction to undesired sites of reaction results in "chemical cross-talk" between synthesis sites. This cross-talk severely compromises the purity of the final product, as undesired binding reactions occur at unselected sites. The amount of cross-talk is further aggravated by the disruptions of surface tension that occur whenever the electrodes are moved, leading to convective mixing that causes increased movement of the electrochemically generated reagents. While Southern attempts to minimize the amount of cross-talk by applying a potential designed to counteract diffusion, as a practical matter, the electric fields Southern can generate are too low to prevent diffusion. When the potential is raised to increase the electric field, large quantities of undesired electrochemically generated reagents are produced. Hence, Southern is not a practical method for generating large number of pure polymers.

A more recent attempt to automate the synthesis of polymers is disclosed by Heller in International patent application WO 95/12808, published May 11, 1995. Heller describes a self-addressable, self-assembling microelectronic system that can carry out controlled multi-step reactions in microscopic environments, including biopolymer synthesis of oligonucleotides and peptides. The Heller method employs free field electroporesis to transport analytes or reactants to selected micro-location where they are effectively concentrated and reacted with the specific binding entities. Each micro-location of the Heller device has a derivatized surface for the covalent attachment of specific binding entities, which includes an attachment layer, a permeation layer, and an underlying direct current microelectrode. The presence of the permeation layer prevents any electrochemically generated reagents from interacting with or binding to either the points of synthesis or to reagents that are electrophoretically transported to each synthesis site. Thus, all synthesis is due to reagents that are electrophoretically transported to each site of synthesis.

The Heller method, however, is severely limited by the use of electrophoretic transport. First, electrophoretic transport requires that the reactants be charged in order to be affected by the electric fields; however, conventional reactants of interest for combinatorial chemistry are usually uncharged molecules not useable in an electrophoretic system. Second, the Heller method does not, and cannot, address the large amount of chemical crosstalk that inherently occurs because of the spatial distribution of the electric fields involved in the electrophoretic transport of the reagents for binding. In a system utilizing electrophoresis, one cannot use protecting groups to protect the reactive functional groups at the microlocations since there is no mechanism for removing the protective groups; yet, the use of electrophoresis results in various binding entities and/or reactants being located throughout the solution used as they migrate, often coming into contact with unselected reaction sites. Thus, the combination of the lack of protecting groups and the spatial distribution of the electric fields inherent to electrophoresis allow such binding reactions to occur randomly, compromising the fidelity of any polymer being synthesized.

From the above, it is seen that there is an existing need and desire for an improved method for synthesizing a variety of chemical sequences at known locations that uses highly efficient deprotection and coupling mechanisms. It is further seen that there is an existing need and desire for a method for synthesizing a variety of chemical sequences at known locations that is cost-effective and practical, and that allows use of a smaller sized apparatus affording more efficient production in a specific area and time, while maintaining the fidelity of the chemical sequence produced. As should be clear to those skilled in the art, the above discussion directed to polypeptide synthesis from monomers is equally applicable to oligonucleotide, and more specifically, deoxyribonucleic acid (DNA) synthesis from deoxyribonucleotide monomers.

It is therefore an object of the present invention to provide an improved method for the placement of a material at a specific location on a substrate. It is further an object of the present invention to provide an improved method for the rapid synthesis of an array of separate, diverse and pure polymers or oligonucleotides on a substrate.

It is still a further object of the invention to provide a substrate for separate and pure polymer or oligonucleotide or DNA synthesis that contains a multi-electrode array that allows electrodes to be placed in very close proximity for use in combinatorial chemistry. It is still another object of the invention to provide a substrate for separate and pure polymer or DNA synthesis that contains a multi-electrode array of electrodes in very close proximity, that allows for automation of a polymer or DNA synthesis process, and that can be used in functional genomics, diagnostics, gene screening, drug discovery and screening for materials useful for research, industrial, commercial and therapeutic uses.

Additional features and advantages of the present invention will be set forth in part in the description that follows, and in part will be apparent from the description, or may be learned by practice of the invention. The objectives and other advantages of the present invention will be realized and attained by means of the elements and combinations particularly pointed out in the written description and appended claims.

SUMMARY OF THE INVENTION

The foregoing objects have been accomplished in accordance with this invention by providing a method for electrochemical placement of a material at a specific location on a substrate, which comprises the steps of:

providing a substrate having at its surface at least one electrode that is proximate to at least one molecule that is reactive with an electrochemically generated reagent, applying a potential to the electrode sufficient to generate electrochemical reagents capable of reacting to the at least one molecule proximate to the electrode, and producing a chemical reaction thereby.

The present invention also includes a method for the electrochemical placement of a material at a specific location on a substrate comprising the steps of:

providing a substrate having at its surface at least one electrode that is proximate to at least one molecule bearing at least one protected chemical functional group, applying a potential to the electrode sufficient to generate electrochemical reagents capable of deprotecting at least one of the protected chemical functional groups of the molecule, and bonding the deprotected chemical functional group with a monomer or a pre-formed molecule.

The present invention also includes a method for electrochemical synthesis of an array of separately formed polymers on a substrate, which comprises the steps of:

placing a buffering or scavenging solution in contact with an array of electrodes that is proximate to a substrate surface, said surface being proximate to one or more molecules bearing at least one protected chemical functional group attached thereto, selectively deprotecting at least one protected chemical functional group on at least one of the molecules;

bonding a first monomer having at least one protected chemical functional group to one or more deprotected chemical functional groups of the molecule;

selectively deprotecting a chemical functional group on the bonded molecule or another of the molecules bearing at least one protected chemical functional group;

bonding a second monomer having at least one protected chemical functional group to a deprotected chemical functional group of the bonded molecule or the other deprotected molecule; and repeating the selective deprotection of a chemical functional group on a bonded protected monomer or a bonded protected molecule and the subsequent bonding of an additional monomer to the deprotected chemical functional group until at least two separate polymers of desired length are formed on the substrate surface.

Another embodiment of the present invention also includes a method for electrochemical synthesis of an array of separately formed oligonucleotides on a substrate, which comprises the steps of:

placing a buffering or scavenging solution in contact with an array of electrodes that is proximate to a substrate surface, said surface being proximate to one or more molecules bearing at least one protected chemical functional group attached thereto, selectively deprotecting at least one protected chemical functional group on at least one of the molecules;

bonding a first nucleotide having at least one protected chemical function group to one or more deprotected chemical functional groups of the molecule;

selectively deprotecting a chemical functional group on the bonded molecule or another of the molecules bearing at least one protected chemical functional group;

bonding a second nucleotide having at least one protected chemical functional group to a deprotected chemical functional group of the bonded molecule or the other deprotected molecule; and repeating the selective deprotection of a chemical functional group on a bonded protected nucleotide or a bonded protected molecule and the subsequent bonding of an additional nucleotide to the deprotected chemical functional group until at least two separate oligonucleotides of desired length are formed on the substrate surface.

A further embodiment of the present invention includes placing a "getter" structure such as a second electrode proximate to the array of electrodes or proximate to each of the electrodes individually. Such a "getter" structure may reduce chemical crosstalk between adjacent electrodes and/or prolong the life of semiconductor circuitry. Various semiconductor circuitry may be placed in a manner to control electrodes individually or corporately according to any one of the methods that are well known in the art. A "getter" structure in accordance with the present invention may be placed in an appropriate location either exposed to the external environment or internal to a semiconducting device.

By using the electrochemical techniques discussed herein, it is possible to place monomers, both those that can be used for polymer synthesis and those that can be decorated, and pre-formed molecules at small and precisely known locations on a substrate. It is therefore possible to synthesize polymers of a known chemical sequence at selected locations on a substrate. For example, in accordance with the presently disclosed invention, one can place nucleotides at selected locations on a substrate to synthesize desired sequences of nucleotides in the form of, for example, oligonucleotides.

It is to be understood that both the foregoing general description and the following detailed description are exemplary and explanatory only and are intended to provide further explanation of the present invention, as claimed.

BRIEF DESCRIPTION OF THE DRAWINGS

FIGS. 1a and 1b illustrate selective deprotection by electrochemically generated reagents (protons) generated at electrodes 1 and 4 to expose reactive functionalities ($NH_2$) on linker molecules (L) proximate electrodes 1 and 4. The substrate is shown in cross section and contains 5 electrodes.

FIGS. 3a and 3b illustrate selective deprotection by protons generated at electrodes 2 and 4 of a second set of reactive functionalities on the molecule and monomer proximate electrodes 2 and 4, respectively.

As shown in FIG. 18a, the chip is attached to the PGA package with glue on the opposite side of the chip from the active area (active area is the area having electrodes at its surface), which leaves the active electrode area protruding from the end of the PGA package in a manner that allows the active area of the chip to be dipped or immersed into solutions. The electrical wires that connect the bond pads on the chip to the bond pads on the PGA package are encased in epoxy. The pins shown in FIG. 18b are located on the opposite side of the PGA package shown in FIG. 18a.

FIG. 19b shows the electrode array after all of the electrodes in the array were exposed to the same voltage and deprotection occurred at each electrode in the array. A voltage of 2.8 volts was applied for 10 minutes. This photomicrograph was taken using a 4 x objective and using a 1 second integration time.

FIG. 33 demonstrates that the getter current continues to rise for several hours after initial exposure to ions indicating a concomitant lowering in the threshold voltage of the gate. These results indicate that the sodium ions are diffusing away from the gate region. The time course of the current rise follows an approximately logarithmic course for the first few hours.

FIG. 34a depicts a top view of an electrode array having a "getter" structure 2 which forms a substantial sheet around the individual electrodes 1 configured in the electrode array. Such a "getter" structure 2 in a sheet functions to capture ions which may diffuse into or toward the semiconductor circuitry. FIG. 34b depicts a cross-section of a selected electrode having a "getter" structure 2 placed substantially at the interface between an insulating dielectric layer 3 and the metal surface of the semiconductor, The "getter" structure in this figure forms a substantially solid sheet with holes allowing the selected electrodes to contact the environment. This and similar structures extend the lifetime of semiconductor circuitry thereby making practical the submersion of a chip in ionic solutions.

FIG. 35a represents a top view showing a selected electrode having a "getter" structure 2 forming a substantial ring around the selected electrode. FIG. 35b presents a cross section of the same showing a selected electrode having a "getter" structure 2 forming a substantial ring around the selected electrode 1.

FIG. 36a represents a top view showing a selected electrode having a "getter" structure 2 forming a substantial ring around the selected electrode 1 and beneath the top surface of the selected electrode. FIG. 35b represents a cross section of the same showing a selected electrode having a "getter" structure 2 forming a substantial ring around the selected electrode 1. The "getter" structure is placed beneath the external surface of the insulating dielectric 3 in this configuration.

DETAILED DESCRIPTION OF THE INVENTION

Figure 2A:
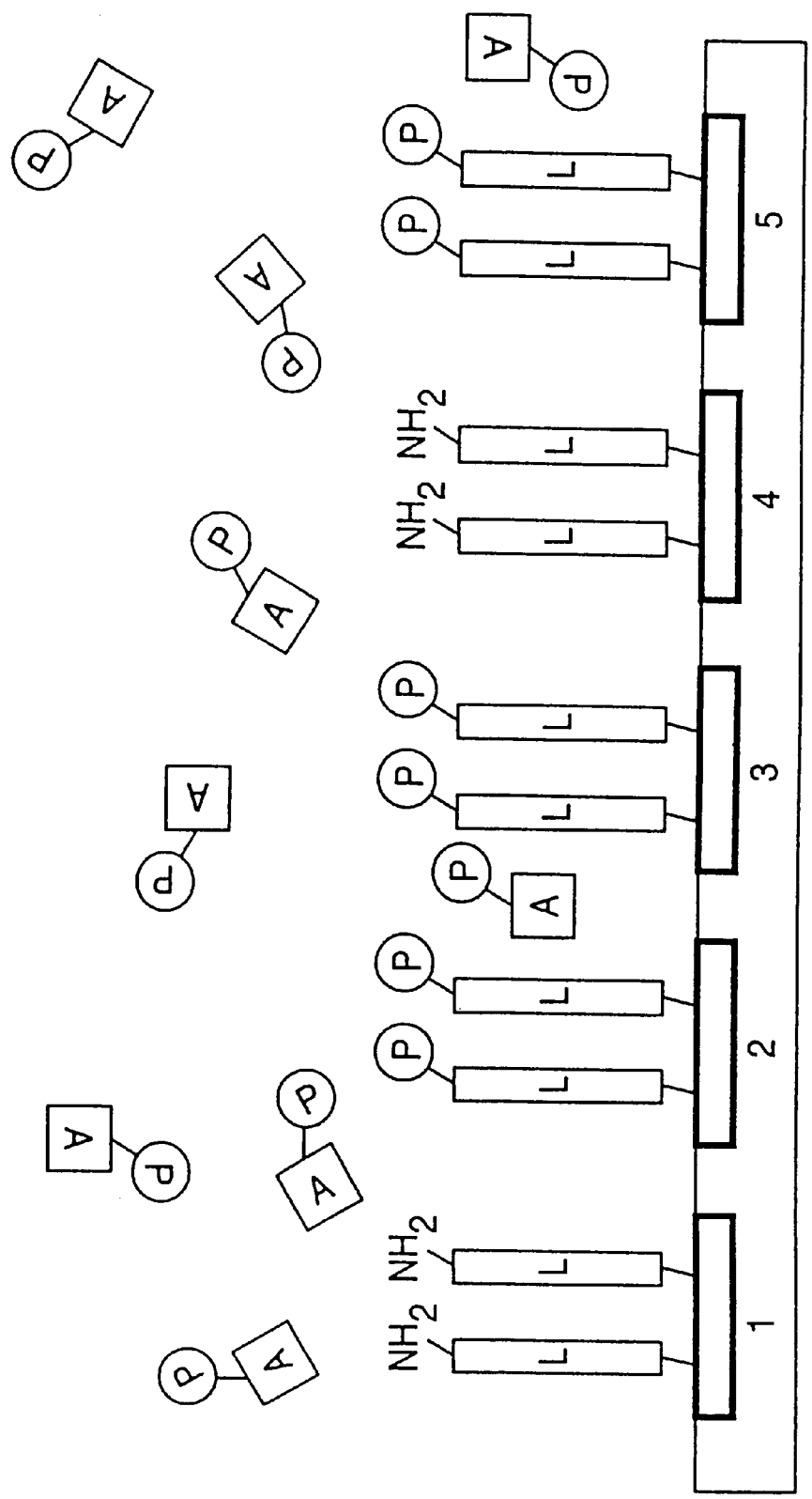
FIGS. 2a and 2b illustrate the bonding of monomers (A) bearing protected chemical functional groups (P) with the deprotected linker molecules (bearing reactive functionalities) proximate electrodes 1 and 4.
Figure 2B:
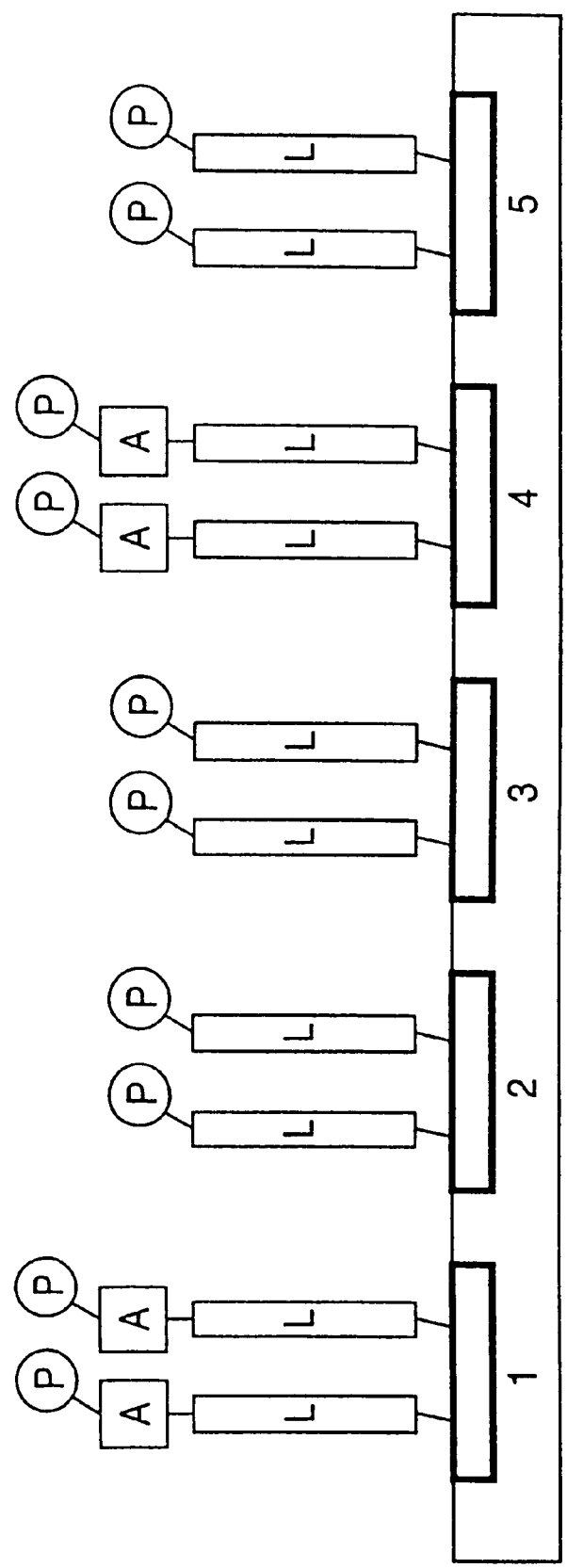
Figure 4A:
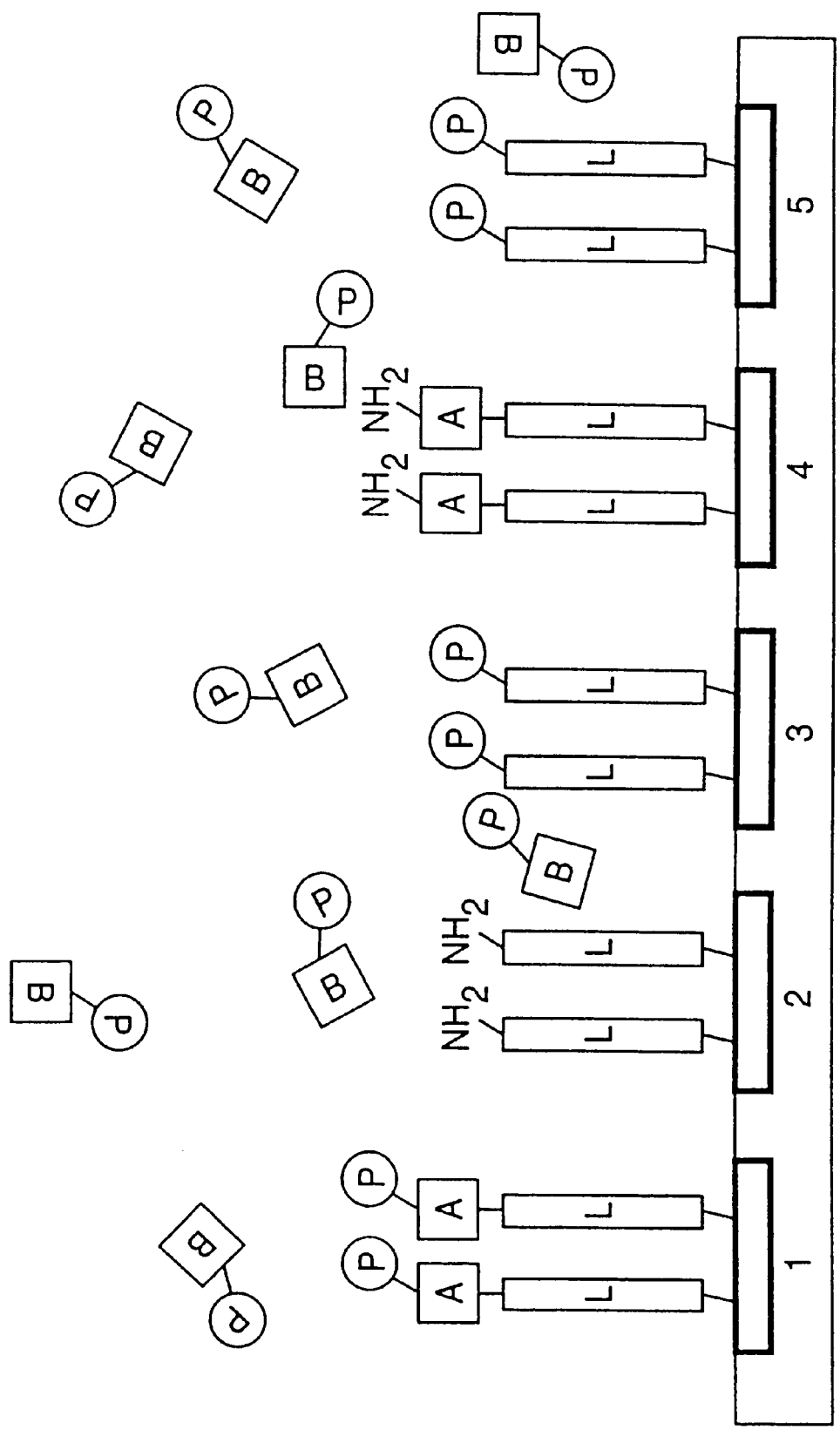
FIGS. 4a and 4b illustrate the bonding of monomers (B) bearing protected chemical functional groups (P) with the deprotected molecule and monomer proximate electrodes 2 and 4, respectively.
Figure 4B:
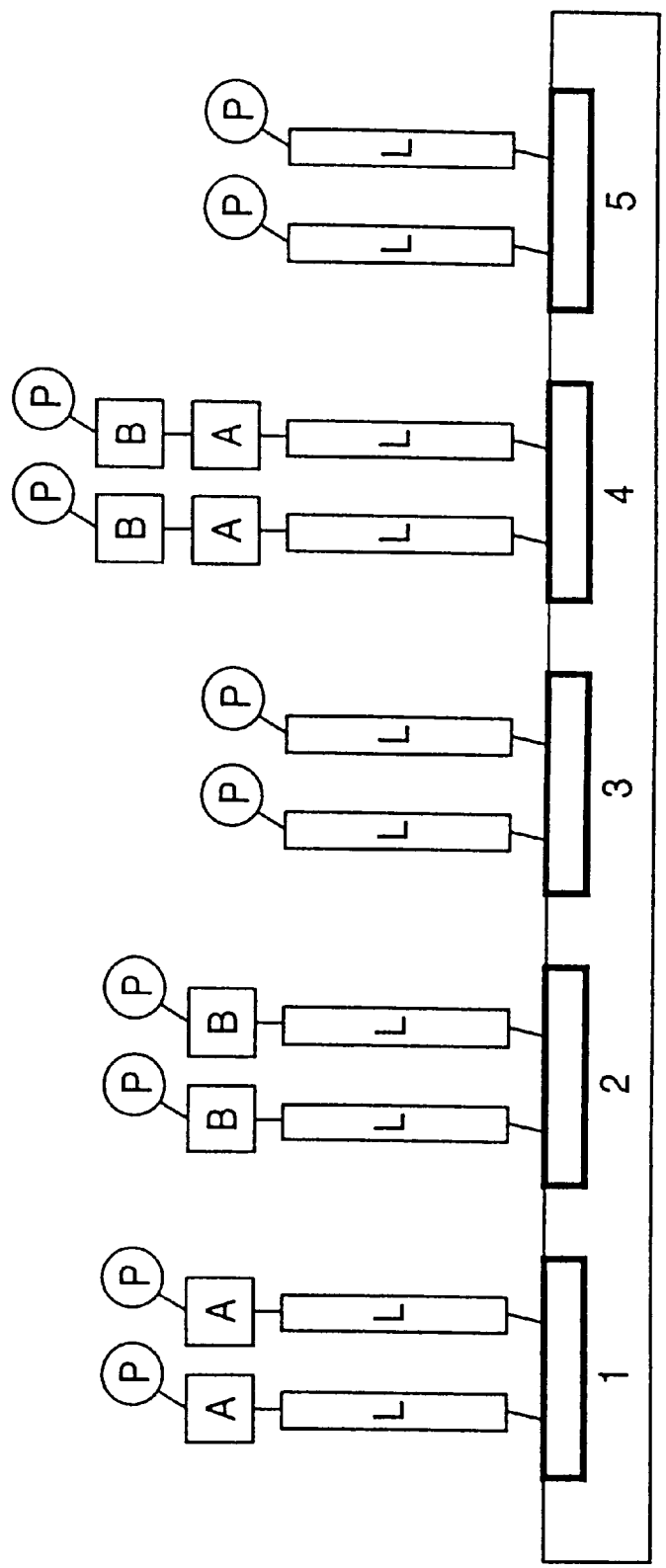
Figure 5:
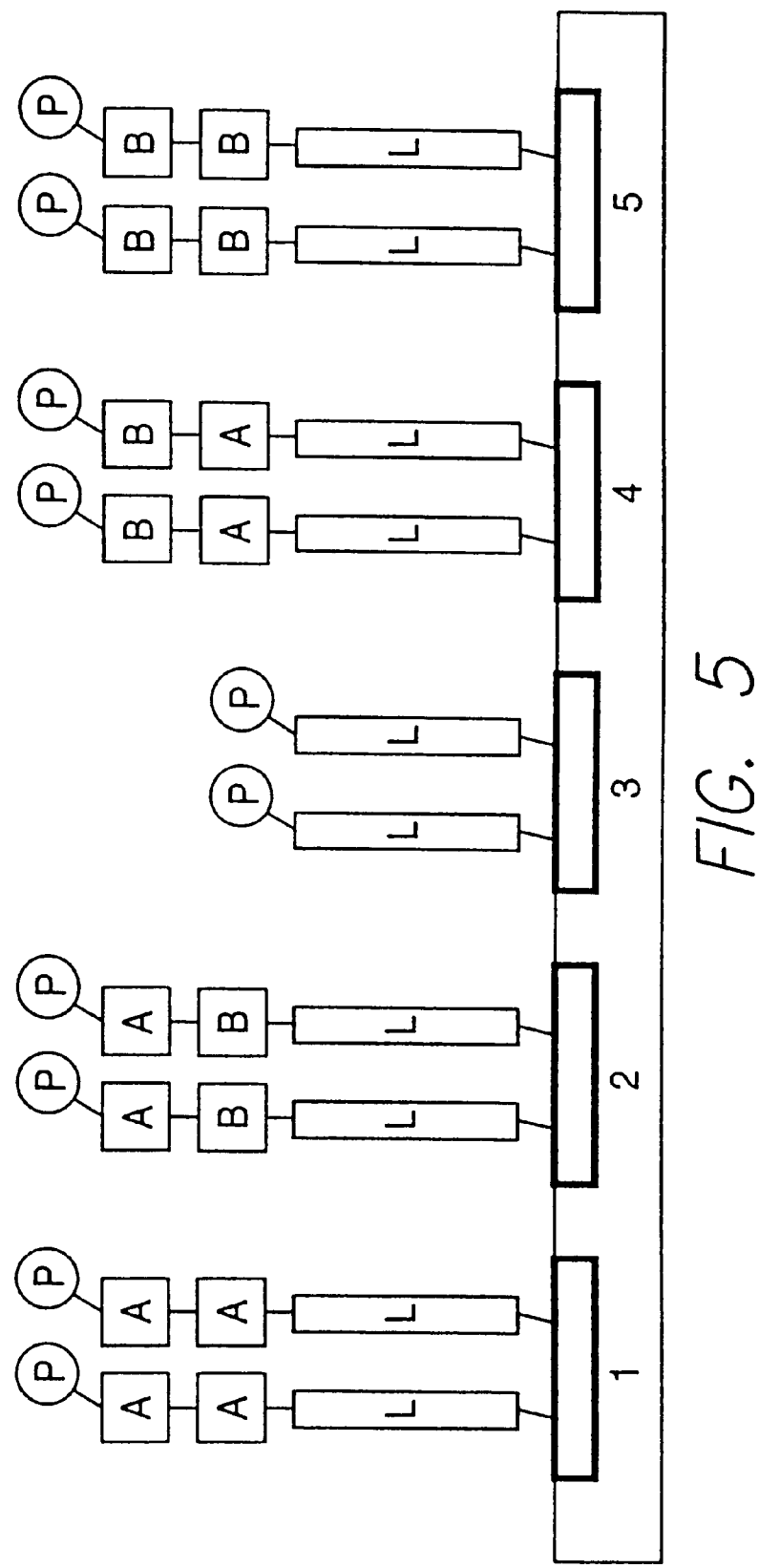
FIG. 5 illustrates a 5 electrode substrate bearing all possible combinations of monomers (A) and (B). The linker molecule proximate electrode 1 has a protected dimer, e.g., a dipeptide, containing two (A) monomers bonded thereto. The linker molecule proximate electrode 2 has a protected dimer containing a (B) monomer bonded to the linker molecule (L) and a protected (A) monomer bonded to said (B) monomer. The linker molecule proximate electrode 3, which represents a control electrode, demonstrates a linker molecule where no synthesis occurs because no potential is applied to the proximate electrode. The linker molecule proximate electrode 4 has a protected dimer containing an (A) monomer bonded to a linker molecule (L) and a protected (B) monomer bonded to said (A) monomer. The linker molecule proximate electrode 5 has a protected dimer containing two (B) monomers bonded to a linker molecule (L).

The present invention provides methods for the preparation and use of a substrate having one or a plurality of chemical species in selected regions. The present invention is described herein primarily with regard to the preparation of molecules containing sequences of amino acids, but could be readily applied to the preparation of other polymers, as well as to the preparation of sequences of nucleic acids. Such polymers include, for example, both linear and cyclic polymers of nucleic acids, polysaccharides, phospholipids, and peptides having either alpha-, beta-, omega- amino acids, polyurethanes, polyesters, polycarbonates, polyureas, polyamides, polyethyleneimines, polyarylene sulfides, polysiloxanes, polyimides, polyacetates, or other polymers which will be apparent upon review of this disclosure. In a preferred embodiment, the invention herein is used in the synthesis of peptides. In another preferred embodiment, the present invention is used for the synthesis of oligonucleotides and/or DNA.

The present invention is directed to placing molecules, selected generally from monomers, linker molecules and pre-formed molecules, including, in particular, nucleic acids, at a specific location on a substrate. The present invention is more particularly directed to the synthesis of polymers at a specific location on a substrate, and in particular polypeptides, by means of a solid phase polymerization technique, which generally involves the electrochemical removal of a protecting group from a molecule provided on a substrate that is proximate at least one electrode. The present invention is also particularly directed to the synthesis of oligonucleotides and/or DNA at selected locations on a substrate, by means of the disclosed solid phase polymerization technique.

Electrochemical reagents capable of electrochemically removing protecting groups from chemical functional groups on the molecule are generated at selected electrodes by applying a sufficient electrical potential to the selected electrodes. Removal of a protecting group, or "deprotection," in accordance with the invention, occurs at selected molecules when a chemical reagent generated by the electrode acts to deprotect or remove, for example, an acid or base labile protecting group from the selected molecules.

In one embodiment of the present invention, a terminal end of a monomer nucleotide, or linker molecule (i.e., a molecule which "links," for example, a monomer or nucleotide to a substrate) is provided with at least one reactive functional group, which protected with a protecting group removable by an electrochemically generated reagent. The protecting group(s) is exposed to reagents electrochemically generated at the electrode and removed from the monomer, nucleotide or linker molecule in a first selected region to expose a reactive functional group. The substrate is then contacted with a first monomer or pre-formed molecule, which bonds with the exposed functional group(s). This first monomer or pre-formed molecule may also bear at least one protected chemical functional group removable by an electrochemically generated reagent.

The monomers or pre-formed molecules can then be deprotected in the same manner to yield a second set of reactive chemical functional groups. A second monomer or pre-formed molecule, which may also bear at least one protecting group removable by an electrochemically generated reagent, is subsequently brought into contact with the substrate to bond with the second set of exposed functional groups. Any unreacted functional groups can optionally be capped at any point during the synthesis process. The deprotection and bonding steps can be repeated sequentially at this site on the substrate until polymers of oligonucleotides of a desired sequence and length are obtained.

In another embodiment of the present invention, the substrate having one or more molecules bearing at least one protected chemical functional group bonded thereto is proximate an array of electrodes, which array is in contact with a buffering or scavenging solution. Following application of an electric potential to selected electrodes in the array sufficient to generate electrochemical reagents capable of deprotecting the protected chemical functional groups, molecules proximate the selected electrodes are deprotected to expose reactive functional groups, thereby preparing them for bonding. A monomer solution or a solution of pre-formed molecules, such as proteins, nucleic acids, polysaccharides, and porphyrins, is then contacted with the substrate surface and the monomers or pre-formed molecules bond with the deprotected chemical functional groups.

Another sufficient potential is subsequently applied to select electrodes in the array to deprotect at least one chemical functional group on the bonded molecule or another of the molecules bearing at least one protected chemical functional group. A second monomer or pre-formed molecule having at least one protected chemical functional group is subsequently bonded to a deprotected chemical functional group of the bonded molecule or the other deprotected molecule. The selective deprotection and bonding steps can be repeated sequentially until polymers or oligonucleotides of a desired sequence and length are obtained. The selective deprotection step is repeated by applying another potential sufficient to effect deprotection of a chemical functional group on a bonded protected monomer or a bonded protected molecule. The subsequent bonding of an additional monomer or pre-formed molecule to the deprotected chemical functional group(s) until at least two separate polymers or oligonucleotides of desired length are formed on the substrate. FIGS. 1–5 generically illustrate the above-discussed embodiments.

Preferred embodiments of the present invention use a buffering or scavenging solution in contact with each electrode, which is buffered towards the electrochemically generated reagents, in particular, towards protons and/or hydroxyl ions, and that actively prevents chemical cross-talk caused by diffusion of the electrochemically generated ions from one electrode to another electrode in an array. For example, when an electrode exposed to an aqueous or partially aqueous media is biased to a sufficiently positive (or negative) potential, protons (or hydroxyl ions) are produced as products of water hydrolysis. Protons, for example, are useful for removing electrochemical protecting groups from several molecules useful in combinatorial synthesis, for example, peptides, nucleic acids, and polysaccharides.

In order to produce separate and pure polymers, it is desirable to keep these protons (or hydroxyl ions) confined to the area immediately proximate the selected electrode(s) in order to minimize, and, if possible to eliminate, chemical cross-talk between nearby electrodes in an array. The spatial extent of excursion of electrochemically generated reagents can be actively controlled by the use of a buffering or scavenging solution that reacts with the reagents that move away from the selected electrodes, thus preventing these reagents from reacting at a nearby electrode.

Another technique for confining these electrochemically generated reagents to the area immediately proximate the selected electrode(s) is to place a "getter" structure in proximity to the selected electrode(s) and substantially exposed to the external environmental. Such a "getter" structure may be used in conjunction with or in place of a scavenging solution. A "getter" structure may be designed of any suitable material and formed into any suitable shape or size as skilled artisans will readily appreciate. The most important criteria for such a "getter" structure is that it function to scavenge electrochemically generated reagents that may diffuse away from the selected electrode(s). The "getter" structure may function passively by reacting chemically with the electrochemically generated reagents. Alternatively, the "getter" structure may function actively to scavenge the electrochemically generated reagents. This may be performing by applying sufficient potential to the "getter" structure to cause electrochemical scavenging. Another function of the "getter" structure may be to prevent the diffusion of ions toward or into circuitry such as transistors that may be operably linked to the selected electrode (s). In accordance with this function, the "getter" structure may be placed substantially at the interface between an insulating dielectric and a metallization layer operably linked to the selected electrode(s).

Some preferred embodiments of such as "getter" structure include a metal sheet that may cover or substantially cover the surface of the circuitry of the electrode device used in the present invention. An example of such a structure is depicted in FIG. 34. This metal sheet may have holes existing where the electrodes are placed. The electrodes may in turn be separated from the "getter" structure by a dielectric as is demonstrated in FIG. 31. Even more preferred embodiments of such a "getter" structure include a ring electrode around the selected electrode(s). A ringed "getter" structure offers at least two advantages over other embodiments such as those described above. First, much of the diffusion of ions occurs along defect sites that form at the interface between the selected electrode(s) and the dielectric. Second, it is relatively easy to monitor the effects of the "getter" structure on the environment when such a structure is utilized. Such a structure is exemplified in FIGS. 31 and 34–36.

The "getter" structure according to the present invention further solves the problem associated with exposing semiconductor devices that may be used in conjunction with the selected electrodes to environments that contain ions that diffuse into the device. In particular, ions from solutions to which a semiconductor device is exposed may diffuse into regions of a semiconductor device that have been doped with ions in a precise manner to impart particular electrical properties to these regions. An important example is the gate of a metal oxide semiconductor (MOS) transistor circuit element. Here either positive or negative ions (e.g, p-doped or n-doped) have been diffused into the gate region to make the region semiconducting. The threshold voltage and current-voltage characteristics of the transistor gate depend in a sensitive way on doping levels. The long term reliability of many semiconductor devices depends on isolating them effectively from ionic contamination. For example, the adhesives and encapsulants used in the semiconductor industry are treated to render the ion concentrations in these materials as low as possible, often less than parts per million.

Semiconductor transistors are rapidly destroyed when silicon chips are used in ion-containing solutions. Semiconductor transistors are presently manufactured with a thin layer of partially conductive material in their transistor junctions. This partially conductive layer is infused or doped with a concentration of particles, i.e. ions, to achieve a balanced level of conductivity. This is typically done at present by doping the junction with a substrate rich in ions such as arsenic, boron or phosphorous. When too many ions are present, the material functions as a metal and becomes highly conductive. When there are two few ions present, the material functions as an insulator and demonstrates very low conductivity. In order to perform properly as a transistor, the material much achieve a very specific level of conductivity intermediate between that of a metal and that of an insulator. Contamination of the partially conductive layer at the transistor junction by ions diffusing into a semiconductor device changes conductivity of the junction and thus destroys the transistor.

Ion contamination represents a serious obstacle for exposing semiconductor circuitry to hostile or ion-containing solutions. This presents a major impediment to devices according to some embodiments of the present invention wherein semiconductor circuitry may be operably linked to selected electrode(s), which are in turn immersed in high concentration ionic solution for extended periods of time. As a result, embodiments according to the present invention that utilize structures such as a "getter" structure are designed both to monitor and to obviate ion contamination are particularly preferred.

Such devices may be designed to work by scavenging ions that diffuse into the device from solutions to which the electrode and associated circuitry may be exposed. Contaminating ions may be scavenged passively by reacting chemically with a material that is placed between them and the active circuitry. Alternatively, they can be scavenged actively by applying a voltage to a second electrode placed proximate to the selected electrode(s) that sets up an electric field that causes ions to migrate to the electrode and away from the active circuitry. Ion contamination can be monitored by placing transistor gates adjacent to the getter structure and monitoring shifts in threshold voltage. Such "getter" structures may be designed by skilled artisans of any suitable material in any suitable size or shape and thereby be adapted to any electrode geometrics. Moreover, it is generally preferable to place the "getter" structure beneath an electrically insulating or dielectric layer such as a silicon nitride that generally covers a semiconductor and thereby separates the semiconductor from the environment, and, in particular, from the ionic solutions required in the practice of the present invention. It is particularly preferable to place the "getter" structure in a ring either substantially beneath or substantially within a dielectric layer and substantially surrounding the select electrode(s). An exemplary cross-section of such a structure is presented in FIG. 34. As a result of the "getter" structure used in accordance with the present invention, selected electrode(s) may be advantageously controlled by automated computer circuitry while maintaining a viable lifespan for the same in the environment of ionic solutions. Thus, it is practical to synthesize a variety of chemical molecules on the surface of electrodes integrated into or operably linked to a computer chip in accordance with methods well known to those of skill in the art.

The present invention advantageously minimizes, and preferably eliminates, chemical cross-talk between nearby areas of polymer or nucleic acid sequence synthesis on a substrate, thus enabling the synthesis of separate arrays of pure polymers or nucleic acid sequences in a small specified area on a substrate using conventional electrochemically generated reagents and known electrochemical reactions. The ability of the inventive methods to place materials at specific locations on a substrate enables the inventive method to be used in several areas of synthesis in addition to polymer synthesis. Several examples of this synthesis include DNA and oligonucleotide synthesis, monomer decoration, which involves the addition of chemical moieties to a single monomer, and inorganic synthesis, which involves the addition of, for example, metals to porphyrins.

Other embodiments of the present invention contemplate an array of electrodes of small micron size, for example, ranging from 1 to 100 microns in diameter, and separated by many microns. However, it is also contemplated that electrodes separated by only submicron distances can be used, if desired. This arrangement affords a large quantity of separate and pure polymers or nucleic acid sequences to be synthesized simultaneously in a small area on a substrate in accordance with the inventive method. This capability renders the inventive method easily automated. The ability of the present invention to be automated easily while retaining the capability of producing separate and diverse arrays of pure polymers and nucleic acid sequences makes the present invention ideal for use in the rapidly developing areas of combinational chemistry and functional genomics.

Essentially, any conceivable substrate may be employed in accordance with the present invention. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat, but may take on a variety of alternative structure configurations. For example, the substrate may contain raised or depressed regions on which synthesis may take place. The substrate and its surface preferably form a rigid support on which to carry out the reactions described herein. The substrate and the area for synthesis of each individual polymer or small molecule may be of any size and shape. Moreover, a substrate may comprise different materials at different regions.

Contemplated materials, which are preferable used as substrates and which are capable of holding and insulating electrically the electrodes, include: undoped semiconductors, such as silicon nitride, silicon oxide, silicon, diamond, chalcopyrites, wurtzites, sphalerites, halites, Group III–V compounds, and Group I–IV compounds; glass, such as, cobalt glass, pyrex glass, vycor glass, borosilicate glass and quartz; ceramics, such as, alumina, porcelain, zircon, corderite, titanates, metal oxides, clays, and zeolites; polymers, such as, paralyene, high density polyethylene, teflons, nylons, polycarbonates, polystyrenes, polyacylates, polycyanoacrylates, polyvinyl alcohols, polyimides, polyamides, polysiloxanes, polysilicones, polynitriles, polyvinyl chlorides, alkyd polymers, celluloses, epoxy polymers, melamines, urethanes, copolymers and mixtures of any of the above with other polymers, and mixtures of any of the above with glass or ceramics; and waxes, such as apeizon. Other substrate materials will be readily apparent to those of skill in the art upon review of this disclosure.

The substrate of the invention is proximate to at least one electrode, i.e., an electrically conducting region of the substrate that is substantially surrounded by an electrically insulating region. The electrode(s), by being "proximate" to the substrate, can be located at the substrate, i.e., embedded in or on the substrate, can be next to, below, or above the substrate, but need to be in close enough proximity to the substrate so that the reagents electrochemically generated at the electrode(s) can accomplish the desired deprotection of the chemical functional groups on the monomer(s) and/or molecule(s).

In addition to being proximate to at least one electrode, the substrate has on a surface thereof, at least one molecule, and preferably several molecules, bearing at least one chemical functional group protected by an electrochemically removable protecting group. These molecules bearing protected chemical functional groups also need to be proximate to the electrode(s). In this regard, the molecules on the surface of the substrate need to be in close enough proximaity to the electrode(s) so that the electrochemical reagents generated at the electrode can remove the protecting group from at least one protected functional group on the proximate molecule(s).

The molecules bearing a protected chemical functional group that are attached to the surface of the substrate may be selected generally from monomers, linker molecules and pre-formed molecules. Preferably, the molecules attached to the surface of the substrate include monomers, nucleotides, and linker molecules. All of these molecules generally bond to the substrate by covalent bonds or ionic interactions. Alternatively, all of these molecules can be bonded, also by covalent bonds or ionic interactions, to a layer overlaying the substrate, for example, a permeable membrane layer, which layer can be adhered to the substrate surface in several different ways, including covalent bonding ionic interactions, dispersive interactions and hydrophilic or hydrophobic interactions. In still another manner of attachment, a monomer or pre-formed molecule may be bonded to a linker molecule that is bonded to either the substrate or a layer overlaying the substrate.

The monomers, linker molecules and pre-formed molecules used herein, are preferably provided with a chemical functional group that is protected by a protecting group removable by electrochemically generated regeants. If a chemical functional group capable of being deprotected by an electrochemically generated reagent is not present on the molecule on the substrate surface, bonding of subsequent monomers or pre-formed molecules cannot occur at this molecule. Preferably, the protecting group is on the distal or terminal end of the linker molecule, monomer, or pre-formed molecule, opposite the substrate. That is, the linker molecule preferably terminates in a chemical functional group, such as an amino or carboxy acid group, bearing in electrochemically removable protective group. Chemical functional groups that are found on the monomers, linker molecules and pre-formed molecules include any chemically reactive functionality. Usually, chemical functional groups are associated with corresponding protective groups and will be chosen or utilized based on the product being synthesized. The molecules of the invention bond to deprotected chemical functional groups by covalent bonds or ionic interactions.

Monomers used in accordance with the present invention to synthesize the various polymers contemplated include all members of the set of small molecules that can be joined together to form a polymer. This set includes, but is not limited to, the set of common L-amino acids, the set of D-amino acids, the set of synthetic amino acids, the set of nucleotides and the set of pentoses and hexoses. As used herein, monomers include any member of a basis set for synthesis of a polymer. For example, trimers of L-amino acids form a basis set of approximately 8000 monomers for synthesis of polypeptides. Different basis sets of monomers may be used at successive steps in the synthesis of a polymer using the inventive method. The number of monomers that can be used in accordance with the inventive synthesis methods can vary widely, for example from 2 to several thousand monomers can be used, but in more preferred embodiments, the number of monomers will range from approximately 4 to approximately 200, and, more preferably, the number of monomers will range from 4–20.

Additional monomers that can be used in accordance with the invention also include the set of monomers that can be decorated, i.e., monomers to which chemical moieties can be added, such as prostaglandins, benzodiazapinies, thromboxanes and leukotrienes. Combinations of monomers useful for polymer synthesis and monomers that can be decorated are also contemplated by the invention. The above-discussed monomers may be obtained in unprotected form from most any chemical supply company, and most, if not all, can be obtained in protected form from Bachem, Inc., Torrance, Calif. Phosphoramidite monomers for nucleic acid synthesis can be obtained from Applied Biosystems, Inc., Foster City, Calif.

In a preferred embodiment of the invention, the monomers are amino acids containing a protective group at its amino or carboxy terminus that is removable by an electrochemically generated reagent. A polymer in which the monomers are alpha amino acids and are joined together through amide bonds is a peptide, also known as a polypeptide. In the context of the present invention, it should be appreciated that the amino acids may be the L-optical isomer or the D-optical isomer or a mixture of the two. Peptides are at least two amino acid monomers long, and often are more than 20 amino acid monomers long.

Furthermore, essentially any pre-formed molecule can be bonded to the substrate, a layer overlaying the substrate, a monomer or a linker molecule. Pre-formed molecules include, for example, proteins, including in particular, receptors, enzymes, ion channels, and antibodies, nucleic acids, polysaccharides, porphyrins, and the like. Pre-formed molecules are, in general, formed at a site other than on the substrate of the invention. In a preferred embodiment, a pre-formed molecule is bonded to a deprotected functional group on a molecule, monomer, or another pre-formed molecule. In this regard, a pre-formed molecule that is already attached to the substrate may additionally bear at least one protected chemical functional group to which a monomer or other pre-formed molecule may bond, following deprotection of the chemical functional group.

Protective groups are materials that bind to a monomer, a linker molecule or a pre-formed molecule to protect a reactive functionality on the monomer, linker molecule or pre-formed molecule, which may be removed upon selective exposure to an activator, such as an electrochemically generated reagent. Protective groups that may be used in accordance with the present invention preferably include all acid and base labile protecting groups. For example, peptide amine groups are preferably protected by t-butyloxycarbonyl (BOC) or benzyloxycarbonyl (CBZ), both of which are acid labile, or by 9-fluorenylmethoxycarbonyl (FMOC), which is base labile. Additionally, hydroxy groups on phosphoramidites may be protected by dimethoxytrityl (DMT), which is acid labile. Exocyclic amine groups on nucleosides, in particular on phosphoramidites, are preferably protected by dimethylformamidine on the adenosine and guanosine bases, and isobutyryl on the cytidine bases, both of which are base labile protecting groups. This protection strategy is known as fast oligonucleotide deprotection (FOD). Phosphoramidites protected in this manner are known as FOD phosphoramidites.

Additional protecting groups that may be used in accordance with the present invention include acid labile groups for protecting amino moieties; tert-butyloxycarbonyl, tert-amyloxycarbonyl, adamantyloxycarbonyl, 1-methylcyclobutyloxycarbonyl, 2-(p-biphenyl)propyl(2) oxycarbonyl, 2-(p-phenylazophenylyl)propyl(2) oxycarbonyl, α,α-dimethyl-3,5-dimethyloxybenzyloxycarbonyl, 2-phenylpropyl(2)oxycarbonyl, 4-methyloxybenzyloxycarbonyl, benzyloxycarbonyl, furfuryloxycarbonyl, triphenylmethyl (trityl, p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidinooxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl; and basic labile groups for protecting phosphotriester groups; cyanoethyl.

As mentioned above, any unreacted deprotected chemical functional groups may be capped at any point during a synthesis reaction to avoid or to prevent further bonding at such molecule. Capping groups "cap" deprotected functional groups by, for example, binding with the unreacted amino functions to form amides. Capping agents suitable for use in the present invention include: acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

In accordance with the invention, the surface of the substrate is preferably provided with a layer of linker molecules. Linker molecules allow for indirect attachment of monomers or pre-formed molecules to the substrate or a layer overlaying the substrate. The linker molecules are preferably attached to an overlaying layer via silicon-carbon bonds, using, for example, controlled porosity glass (CPG) as the layer material. Linker molecules also facilitate target recognition of the synthesized polymers. Furthermore, the linker molecules are preferably chosen based upon their hydrophilic/hydrophobic properties to improve presentation of synthesized polymers to certain receptors. For example, in the case of a hydrophilic receptor, hydrophilic linker molecules will be preferred so as to permit the receptor to approach more closely the synthesized polymer.

The linker molecules are preferably of sufficient length of permit polymers on a completed substrate to interact freely with binding entities exposed to the substrate. The linker molecules, when used, are preferably 650 atoms long to provide sufficient exposure of the functional groups to the binding entity. The linker molecules, which may be advantageously used in accordance with the invention include, for example, aryl acetylene, ethylene glycol oligomers containing from 2 to 10 monomer units, diamines, diacids, amino acids, and combinations thereof. Other linker molecules may be used in accordance with the different embodiments of the present invention and will be recognized by those skilled in the art in light of this disclosure.

According to another preferred embodiment, linker molecules may be provided with a cleavable group at an intermediate position, which group can be cleaved with an electrochemically generated reagent. This group is preferably cleaved with a reagent different from the reagent(s) used to remove the protective groups. This enables removal of the various synthesized polymers or nucleic acid sequences following completion of the synthesis by include: acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

In accordance with the invention, the surface of the substrate is preferably provided with a layer of linker molecules. Linker molecules allow for indirect attachment of monomers or pre-formed molecules to the substrate or a layer overlaying the substrate. The linker molecules are preferably attached to an overlaying layer via silicon-carbon bonds, using, for example, controlled porosity glass (CPG) as the layer material. Linker molecules also facilitate target recognition of the synthesized polymers. Furthermore, the linker molecules are preferably chosen based upon their hydrophilic/hydrophobic properties to improve presentation of synthesized polymers to certain receptors. For example, in the case of a hydrophilic receptor, hydrophilic linker molecules will be preferred so as to permit the receptor to approach more closely the synthesized polymer.

The linker molecules are preferably of sufficient length to permit polymers on a completed substrate to interact freely with binding entities exposed to the substrate. The linker molecules, when used, are preferably 650 atoms long to provide sufficient exposure of the functional groups to the binding entity. The linker molecules, which may be advantageously used in accordance with the invention include, for example, aryl acetylene, ethylene glycol oligomers containing from 2 to 10 monomer units, diamines, diacids, amino acids, and combinations thereof. Other linker molecules may be used in accordance with the different embodiments of the present invention and will be recognized by those skilled in the art in light of this disclosure.

According to another preferred embodiment, linker molecules may be provided with a cleavable group at an intermediate position, which group can be cleaved with an electrochemically generated reagent. This group is preferably cleaved with a reagent different from the reagent(s) used to remove the protective groups. This enables removal of the various synthesized polymers or nucleic acid sequences following completion of the synthesis by way of electrochemically generated reagents. In particular, derivatives of the acid labile 4,4'-dimethyoxytrityl molecules with an exocyclic active ester can be used in accordance with the present invention. These linker molecules can be obtained from Perseptive Biosystems, Framingham, Mass. More preferably, N-succinimidyl-4-[bis-(4-methoxyphenyl)-chloromethyl]-benzoate is used as a cleavable linker molecule during DNA synthesis. The synthesis and use of this molecule is described in a *Versatile Acid-Labile Linker for Modification of Synthetic Biomolecules,* by Brian D. Gildea, James M. Coull and Hubert Koester, *Tetrahedron Letters,* Volume 31, No. 49, pgs 7095–7098 (1990). Alternatively, other manners of cleaving can be used over the entire array at the same time, such as chemical reagents, light or heat.

The use of cleavable linker groups affords dissociation or separation of synthesized molecules, e.g., polymers or nucleic acid sequences, from the electrode array at any desired time. This dissociation allows transfer of the, for example, synthesized polymer or nucleic acid sequence, to another electrode array or to a second substrate. The second substrate could contain bacteria and serve to assay the effectiveness of molecules made on the original electrode array at killing bacteria. Alternatively, the second substrate could be used to purify the materials made on the original electrode array. Obviously, those skilled in the art can contemplate several uses for transferring the molecules synthesized on the original electrode to a second substrate.

The molecules of the invention, i.e., the monomers, linker molecules and pre-formed molecules, can be attached directly to the substrate or can be attached to a layer or membrane of separating material that overlays the substrate. Materials that can form a layer a membrane overlaying the substrate, such that molecules can be bound there for modification by electrochemically generated reagents, include: controlled porosity glass (CPG); generic polymers, such as, teflons, nylons, polycarbonates, polystyrenes, polyacylates, polycyanoacrylates, polyvinyl alcohols, polyamides, polyimides, polysiloxanes, polysilicones, polynitriles, polyelectrolytes, hydrogels, expoxy polymers' melamines, urethanes and copolymers and mixtures of these and other polymers; biologically derived polymers, such as, polysaccharides, polyhyaluric acids, celluloses, and chitons; ceramics, such as, alumina, metal oxides, clays, and zeolites, surfactants; thiols; self-assembled monolayers; porous carbon; and fullerine materials. The membrane can be located onto the substrate by spin coating, dip coating or manual application, or any other art acceptable form of coating.

Reagents that can be generated electrochemically at the electrodes fall into two broad classes: oxidants and reductants. There are also miscellaneous reagents that are useful in accordance with the invention. Oxidants that can be generated electrochemically include iodine, iodate, periodic acid, hydrogen peroxide, hypochlorite, metavanadate, bromate, dichromate, cerium (IV), and permanganate. Reductants that can be generated electrochemically include chromium (II), ferrocyanide, thiols, thiosulfate, titanium (III), arsenic (III) and iron (II). The miscellaneous reagents include bromine, chloride, protons and hydroxyl ions. Among the foregoing reagents, protons, hydroxyl ions, iodine, bromine, chlorine and the thiols are preferred.

Figure 37:
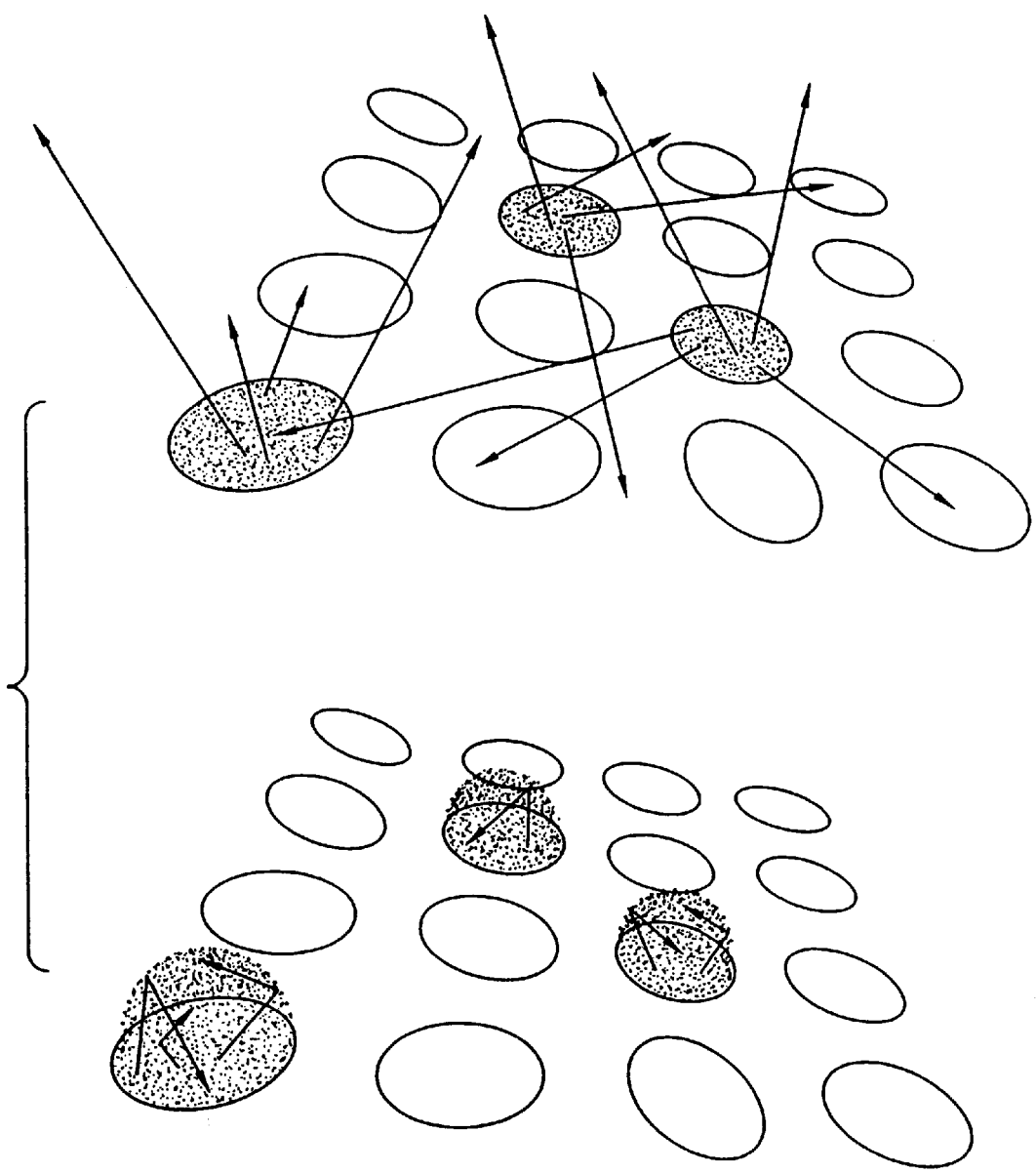
FIG. 37 illustrates how the methods of the present invention function to isolate contaminating ions and thereby prevent chemical cross-talk between neighboring selected electrodes. The buffering and/or scavenging solutions of the present invention alone or combination with a "getter" structure effectively isolate reactive electrochemically generated regents thereby allowing multiple chemical reactions in close proximity.

In accordance with preferred embodiments of the present invention, a buffering and/or scavenging solution is in contact with each electrode. The buffering and/or scavenging solutions that may be used in accordance with the invention are preferably buffered toward, or scavenge, ions such as protons and/or hydroxyl ions, although other electrochemically generated reagents capable of being buffered and/or scavenged are clearly contemplated. The buffering solution functions to prevent chemical cross-talk due to diffusion of electrochemically generated reagents from one electrode in an array to another electrode in the array, while a scavenging solution functions to seek out and neutralize/deactivate the electrochemically generated reagents by binding or reacting with them. Thus, the spatial extent of excursion of electrochemically generated reagents can be actively controlled by the use of a buffering solution and/or a scavenging solution. This function is graphically explained in FIG. 37. In accordance with the invention, the buffering and scavenging solutions may be used independently or together. Preferably, a buffering solution is used because the capacity of a buffering solution is more easily maintained, as compared with a scavenging solution.

Buffering solutions that can be used in accordance with the present invention include all electrolyte salts used in aqueous or partially aqueous preparations. Buffering solutions preferably used in accordance with the present invention include: acetate buffers, which typically buffer around pH 5; borate buffers, which typically buffer around pH 8; carbonate buffers, which typically buffer around pH 9; citrate buffers, which typically buffer around pH 6; glycine buffers, which typically buffer around pH 3; HEPES buffers, which typically buffer around pH 7; MOPS buffer, which typically buffer around pH 7; phosphate buffers, which typically buffer around pH 7; TRIS buffers, which typically buffer around pH8; and 0.1 M KI in solution, which buffers the iodine concentration by the equilibrium reaction $I_2+I^-=I_3^-$, the equilibrium coefficient for this reaction being around $10^{-2}$.

Alternatively, or in combination with a buffering solution, a scavenging solution may be used that contains species such as ternary amines that function as hydroxyl ion scavengers or sulfonic acids that function as proton scavengers in nonaqueous media. The rate at which a reagent/species is scavenged depends both on the intrinsic rate of the reaction occurring and on the concentration of the scavenger. For example, solvents make good scavengers because they are frequently present in high concentrations. Most molecules scavenge in a nonselective way, however, some molecules, such as superoxide dismutase and horseradish peroxidase, scavenge in a selection manner.

Of particular interest to the present invention are scavenger molecules that can scavenge the different reactive species commonly generated, for example, by water hydrolysis at electrodes, including hydroxyl radicals, superoxides, oxygen radicals, and hydrogen peroxide. Hydroxyl radicals are among the most reactive molecules known, their rate of reaction is diffusion controlled, that is, they react with the first reactant/species they encounter. When hydroxyl radicals are generated by water hydrolysis, the first molecule they usually encounter is a water molecule. For this reason, water is a rapid and effective scavenger of hydroxyl radicals. Superoxides are also a relatively reactive species, but can be stable in some nonequeous or partially aqueous solvents. In aqueous media, superoxides rapidly react with most molecules, including water. In many solvents, they can be scavenged selectively with superoxidase dismutase.

Oxygen radicals are a family of oxygen species that exist as free radicals. They can be scavenged by a wide variety of molecules such as water or ascorbic acid. Hydrogen peroxide is a relatively mild reactive species that is useful, in particular, in combinatorial synthesis. Hydrogen peroxide is scavenged by water and many types of oxidizing and reducing agents. The rate at which hydrogen peroxide is scavenged depends on the redox potential of the scavenger molecules being used. Hydrogen peroxide can also be scavenged selectively by horseradish peroxidase. Another electrochemically generated species that can be scavenged is iodine. Iodine is a mild oxidizing reagent that is also useful for combinatorial synthesis. Iodine can be scavenged by reaction with hydroxyl ions to form iodide ions and hypoiodite. The rate at which iodine is scavenged is pH dependent; higher pH solutions scavenge iodine faster. All of the scavenger molecules discussed above may be used in accordance with the present invention. Other scavenger molecules will be readily apparent to those skilled in the art upon review of this disclosure.

In accordance with the present invention, the buffering solutions are preferably used in a concentration of at least 0.01 mM. More preferably, the buffering solution is present in a concentration ranging from 1 to 100 mM, and still mor preferably, the buffering solution is present in a concentration ranging from 10 to 100 mM. Most preferably, the buffering solution concentration is approximately 30 mM. A buffering solution concentration of approximately 0.1 molar, will allow protons or hydroxyl ions to move approximately 100 angstroms before buffering the pH to the bulk values. Lower buffering solution concentrations, such as 0.00001 molar, will allow ion excursion of approximately several microns, which still may be acceptable distance depending on the distance between electrodes in an array.

In accordance with the present invention, the concentration of scavenger molecules in a solution will depend on the specific scavenger molecules used since different scavenging molecules react at different rates. The more reactive the scavenger, the lower the concentration of scavenging solution needed, and vice versa. Those skilled in the art will be able to determine the appropriate concentration of scavenging solution depending upon the specific scavenger selected.

The at least one electrode proximate the substrate of the invention is preferably an array of electrodes. Arrays of electrodes of any dimension may be used, including arrays containing up to several million electrodes. Preferably, multiple electrodes in an array are simultaneously addressable and controllable by an electrical source. More preferably, each electrode is individually addressable and controllable by its own electrical source, thereby affording selective application of different potentials to select electrodes in the array. In this regard, the electrodes can be described as "switchable".

Figure 6:
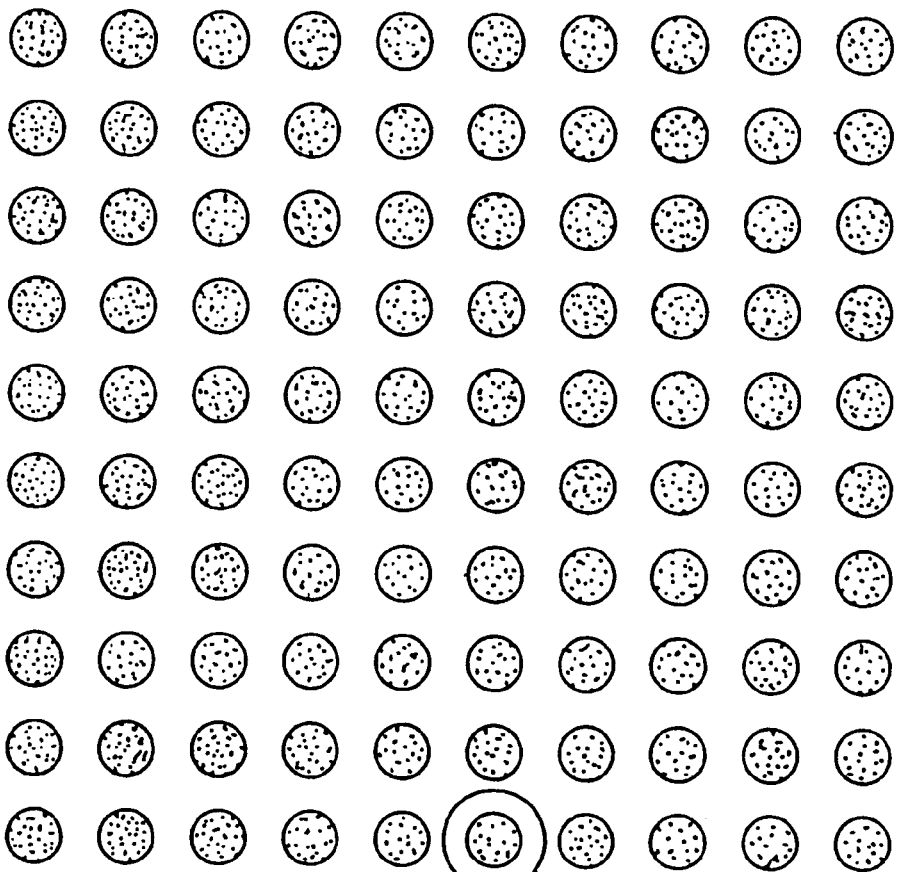
FIG. 6 illustrates a top view diagram of a substrate having at its surface a 10×10 electrode array, having 100 electrodes. A side view of an exemplary electrode at the surface of the substrate is also shown.

The arrays need not be in any specific shape, that is, the electrodes need not be in a square matrix shape. Contemplated electrode array geometries include: squares; rectangles; rectilinear and hexagonal grid arrays with any sort of polygon boundary; concentric circle grid geometries wherein the electrodes form concentric circles about a common center, and which may be bounded by an arbitrary polygon; and fractal grid array geometries having electrodes with the same or different diameters. Interlaced electrodes may also be used in accordance with the present invention. Preferably, however, the array of electrodes contains at least 100 electrodes in a 10×10 matrix. One embodiment of a substrate that may be used in accordance with the present invention having a 10×10 matrix of electrodes is shown in FIG. 6. A side view of an electrode at the surface of the substrate is also shown.

More preferably, the array of electrodes contains at least 400 electrodes in, for example, an at least 20×20 matrix. Even more preferably, the array contains at least 2048 electrodes in, for example, an at least 64×32 matrix, and still more preferably, the array contains at least 204,800 electrodes in, for example, an at least 640×320 array. Other sized arrays that may be used in accordance with the present invention will be readily apparent to those of skill in the art upon review of this disclosure.

Electrode arrays containing electrodes ranging in diameter from approximately less than 1 micron to approximately 100 microns (0.1 millimeters) are advantageously used in accordance with the present invention. Further, electrode arrays having a distance of approximately 10–1000 microns from center to center of the electrodes, regardless of the electrode diameter, are advantageously used in accordance with the present invention. More preferably, a distance of 50–100 microns exists between the centers of two neighboring electrodes.

As shown in the side view of FIG. 6, the electrodes may be flush with the surface of the substrate. However, in accordance with a preferred embodiment of the present invention, the electrodes are hemisphere shaped, rather than flat disks. More specifically, the profile of the hemisphere shaped electrodes is represented by an arctangent function that looks like a hemisphere. Those skilled in the art will be familiar with electrodes of this shape. Hemisphere shaped electrodes help assure that the electric potentials is constant across the radial profile of the electrode. That is, hemisphere shaped electrodes help assure that the electric potential is not larger near the edge of the electrode than in the middle of the electrode, thus assuring that the generation of electrochemical reagents occurs at the same rate at all parts of the electrode.

Electrodes that may be used in accordance with the invention may be composed of, but are not limited to, noble metals such as iridium and/or platinum, and other metals, such as, palladium, gold, silver, copper, mercury, nickel, zinc, titanium, tungsten, aluminum, as well as alloys of various metals, and other conducting materials, such as, carbon, including glassy carbon, reticulated vitreous carbon, basal plane graphite, edge plane graphite and graphite. Doped oxides such as indium tin oxide, and semiconductors such as silicon oxide and gallium arsenide are also contemplated. Additionally, the electrodes may be composed of conducting polymers, metal doped polymers, conducting ceramics and conducting clays. Among the noble metals, platinum and palladium are especially preferred because of the advantageous properties associated with their ability to absorb hydrogen, i.e., their ability to be "preloaded" with hydrogen before being used in the methods of the invention.

In accordance with other preferred embodiments of the present invention, one or more of the electrodes are proximate to a "getter" structure. Preferably the "getter" structure comprises a second electrode. The second electrode may be of any shape or size. However, it may function to scavenge electrochemically generated reagents alone or in conjunction with a scavenging solution and/or a buffering solution or it may function to reduce or eliminate diffusion of ions into nearby electric sources such as semiconductor circuitry. Such second electrodes may be made of the same material as the selected electrodes discussed above.

The electrode(s) used in accordance with the invention may be connected to an electric source in any known manner. Preferred ways of connecting the electrodes to the electric source include CMOS switching circuitry, radio and microwave frequency addressable switches, light addressable switches, and direct connection from an electrode to a bond pad on the perimeter of a semiconductor chip. The placement of a "getter" structure in accordance with the description set forth above and such as the structure exemplified in FIGS. 31 and 34–36 effectively prolongs the life of a semiconductor chip thereby making such a connection particularly advantageous.

CMOS switching circuitry involves the connection of each of the electrodes to a CMOS transistor switch. The switch is accessed by sending an electronic address signal down a common bus to SRAM (static random access memory) circuitry associated with each electrode. When the switch is "on", the electrode is connected to an electric source. This is a preferred mode of operation.

Radio and microwave frequency addressable switches involve the electrodes being switched by a RF or microwave signal. This allows the switches to be thrown both with and/or without using switching logic. The switches can be tuned to receive a particular frequency or modulation frequency and switch without switching logic. Alternatively, the switches can use both methods.

Light addressable switches are switched by light. In this method, the electrodes can also be switched with and without switching logic. The light signal can be spatially localized to afford switching without switching logic. This is accomplished, for example, by scanning a laser beam over the electrode array; the electrode being switched each time the laser illuminates it. Alternatively, the whole array can be flood illuminated and the light signal can be temporally modulated to generate a coded signal. However, switching logic is required for flood illumination.

One can also perform a type of light addressable switching in an indirect way. In this method, the electrodes are formed from semiconductor materials. The semiconductor electrodes are then biased below their threshold voltage. At sufficiently low biases, there is no electrochemistry occurring because the electrons do not have enough energy to overcome the band gap. The electrodes that are "on" will already have been switched on by another method. When the electrodes are illuminated, the electrons will acquire enough energy from the light to overcome the band gap and cause electrochemistry to occur.

Thus, an array of electrodes can be poised to perform electrochemistry whenever they are illuminated. With this method, the whole array can be flood illuminated or each electrode can be illuminated separately. This technique is useful for very rapid pulsing of the electrochemistry without the need for fast switching electronics. Direct connection from an electrode to a bond pad on the perimeter of the semiconductor chip is another possibility, although this method of connection could limit the density of the array.

Electrochemical generation of the desired type of chemical species requires that the electric potential of each electrode have a certain minimum value. That is to say, a certain minimum potential is necessary, which may be achieved by specifying either the voltage or the current. Thus, there are two ways to achieve the necessary minimum potential at each electrode: either the voltage may be specified at the necessary value or the current can be determined such that it is sufficient to accommodate the necessary voltage. The necessary minimum potential value will be determined by the type of chemical reagent chosen to be generated. One skilled in the art can easily determine the necessary voltage and/or current to be used based on the chemical species desired. The maximum value of potential that can be used is also determined by the chemical species desired. If the maximum value of potential associated with the desired chemical species is exceeded, undesired chemical species may be resultantly produced.

The substrates prepared in accordance with the present invention will have a variety of uses including, for example, screening large numbers of polymers for biological activity. To screen for biological activity, for example, in the field of pharmaceutical drug discovery, the substrate is exposed to one or more receptors such as antibodies, whole cells, receptors on vesicles, lipids, or any one of a variety of other receptors. The receptors are preferably labeled with, for example, an electrochemical marker, an electrochemiluminescent marker, a chemiluminescent marker, a fluorescent marker, a radioactive marker, or a labeled antibody reactive with the receptor. The location of the marker on the substrate is detected with, for example, electrochemical, fluorescence or autoradiographic techniques. Through knowledge of the sequence of the material at the location where binding is detected, it is possible to determine quickly which sequence binds with the receptor and, therefore, the technique can be used to screen large numbers of peptides.

The present invention can also be used for therapeutic materials development, i.e., for drug development and for biomaterial studies, as well as for biomedical research, analytical chemistry and bioprocess monitoring. An exemplary application of the present invention includes diagnostics in which various ligands for particular receptors can be placed on a substrate and, for example, blood sera can be screened. Another exemplary application includes the placement of single or multiple pre-formed receptor molecules at selected sites on a substrate and, for example, drug screening could be conducted by exposing the substrate to drug candidate molecules to determine which molecules bind to which pre-formed receptor molecules.

Yet another application includes, for example, sequencing genomic DNA by the technique of sequencing by hybridization. Another contemplated application includes the synthesis and display of differing quantities of molecules or ligands at different spatial locations on an electrode array chip and the subsequent performance of dilution series experiments directly on the chip. Dilution series experiments afford differentiation between specific and non-specific binding of, for example, ligands and receptors. Non-biological applications are also contemplated, and include the production of organic materials with varying levels of doping for use, for example, in semiconductor devices. Other examples of non-biological uses include anticorrosives, antifoulants, and paints.

It is specifically contemplated that the present invention may be used for developing materials. Materials may be developed by methods according to the present invention for many purposes including, but not limited to corrosion resistant, battery energy storage, electroplating, low voltage phosphorescence, bone graft compatibility, resisting fouling by marine organisms, superconductivity, epitaxial lattice matching, or chemical catalysis. Materials for those or other utilities may be formed proximate to one or a plurality of electrodes. Alternatively, materials may be formed by modifying the surface of one or a plurality of electrodes by generating reagents electrochemically. Additionally, materials may be formed by modifying the bulk electrode material of one or a plurality of electrodes using electrochemically generated reagents.

It is further contemplated that methods according to the present invention may be used to develop protocols for testing materials. That is, reagents electrochemically generated by methods according to the present invention may be used to test the physical and chemical properties of materials proximate to one or a plurality of electrodes. For instance, skilled artisans may readily develop protocols to evaluate such properties as corrosion resistance, electroplating efficiency, chemical kinetics, superconductivity, electrochemiluminescence and catalyst lifetimes using electrochemically generated reagents in accordance with the present invention.

The present invention will further be clarified and illustrated by the following examples, which are intended to be merely exemplary of the invention.

EXAMPLES

Example 1

Combinatorial Synthesis of the Leu-enkephalin Epitope

Background

Endorphins are naturally occurring small peptides (including approximately 20–40 amino acids) that bind to opiate receptors in the brain. It has been discovered that most of the activity of endorphins is due to the last five amino acids on the peptides. These terminal pentapeptides are called enkephalins.

The immunofluorescent technique for detecting the Leu-enkephalin epitope follows standard detection protocols. See for example, F. M. Ausubel et al., *Short Protocols in Molecular Biology*, Third edition, Unit 14, pgs. 14–23ff (1995). This assay requires a primary antibody, e.g., the 3-E7 monoclonal antibody, and a secondary antibody-fluorochrome conjugate specific to the source species of primary antibody, e.g., the goat anti-mouse fluorescent conjugate. The 3-E7 antibody is a mouse monoclonal antibody against endorphins that bind to leu-enkephalins. Both of the antibodies for this technique can be obtained from Boehringer Mannheim Biochemicals, Indianapolis, Ind.

For additional information regarding the 3-E7 monoclonal antibody, see, e.g. Meo, Tommaso, et al., "Monoclonal antibody to the message sequence TryGly-Gly-Phe of opioid peptides exhibits the specificity requirements of mammalian opioid receptors," *Proc. Natl. Acad. Sci USA* 80, pgs. 4084–4088 (1983).

Preparation of an Electrode Array for Use in Combinatorial Synthesis

An 10×10 platinum electrode array is used, as is shown in FIG. 6. Columns 1 and 10 are used as counter electrodes. The active columns of the array are columns 2, 3, 5, 6 and 7. Columns 4, 8 and 9 are never activated in this synthesis.

The surface of the array is modified with a permeable membrane layer formed from controlled porosity glass (CPG) that is applied to the array by deposition of silicon dioxide under appropriate conditions in the semiconductor manufacturing process. The CPG forms a chemically inert membrane that is permeable to ions. This membrane is functionalized by silanation with chloromethyl silane. The chloromethyl silane groups are further modified by ethylene glycol linker molecules containing ten ethylene glycol moieties by reacting the silanized CPG membrane with a molecule containing ten ethylene glycol moieties and two amino groups at each end. This membrane provides a layer overlaying the surface of the array that is functionalized by amine groups that are, in turn, attached to the CPG matrix via a silane moiety. The diamino ethylene glycol molecules act as linker molecules (spacer groups) between the membrane and the epitope molecules which are formed.

Addition of Protected Functional Groups to the Membrane

Figure 7:
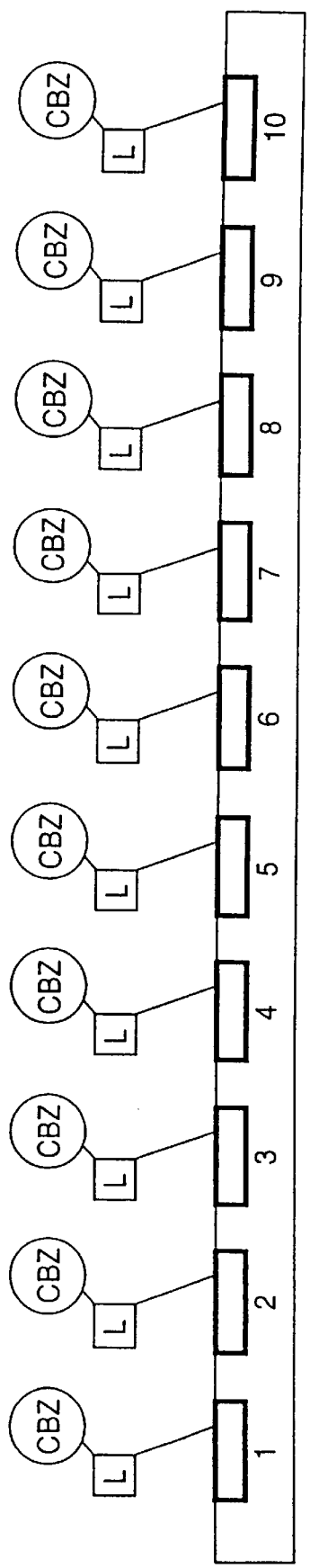
FIG. 7 illustrates a substrate having a permeable attachment layer or membrane having CBZ-protected leucine monomers (L) bonded thereto. The layer/membrane overlays the electrodes at the surface of the substrate.

The functionalized CPG membrane covered electrode array is exposed to a DMF solution of benzyloxycarbonyl (CBZ) protected 1-leucine containing coupling reagents, such as, but not limited to, dicyclohexylcarbodiimide (DCC) or diisopropylcarbodiimide, at room temperature for approximately two hours. This exposure produces a CPG membrane layer covering the array that is completely covered with CBZ-protected 1-leucine moieties attached to the membrane layer by ethylene glycol linker molecules. This moiety covered membrane layer is shown in FIG. 7. This is the bed of molecules on which the epitope molecule is built.

The moiety covered membrane layer is then washed three times with an aqueous 0.1 M phosphate buffered solution having a pH of 7.4.

Removal of the Protecting Groups (Deprotection)

Removal of the CBZ protecting groups from the protected amino acids, i.e., deprotection, using electrochemically generated reagents (protons) is performed as follows.

Referring to the electrode array of FIG. 6, a preconditioning step is performed: columns 2, 3, 5, 6, and 7 are biased negative with respect to columns 1 and 10, which serve as counter electrodes. There is no reference electrode in this system. The potential difference is approximately 3 volts, which voltage is applied for approximately 10 seconds. This preconditioning step causes hydroxyl ions to be formed at the electrodes with a negative bias and protons to be formed at the counter electrodes having a positive bias. This preconditioning step also causes protons to be reduced to hydrogen molecules at electrodes with a negative bias. The platinum electrodes absorb and hold some of these hydrogen molecules in the bulk metal.

Following the preconditioning step, the bias is then reversed. The electrodes of columns 1 and 10 (counter electrodes) are biased negative with respect to columns 2, 3, 5, 6, and 7. The potential difference is approximately 2.6 volts, which voltage is applied for approximately three seconds. This step causes protons to be formed at the electrodes with a positive bias both from hydrolysis of water and from oxidation of hydrogen molecules that are absorbed into the platinum electrodes during the preconditioning step. As a result of the preconditioning step and this subsequent step, the CBZ protecting groups are removed from the leucine amino acid moieties at the electrodes in columns 2, 3, 5, 6, and 7.

Figure 8:
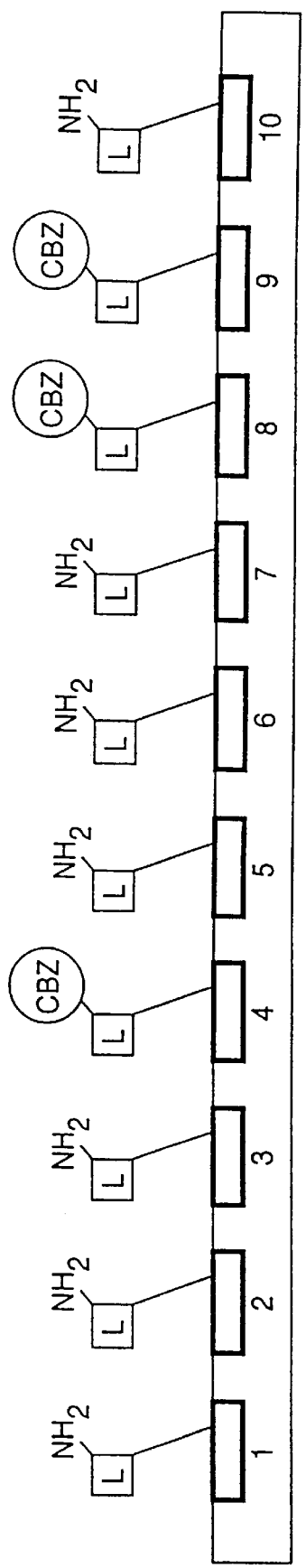
FIG. 8 illustrates a substrate having a permeable attachment layer or membrane overlaying the electrodes at the surface, which layer/membrane contains leucine monomers (L) bearing reactive amine functionalities, e.g., following removal of protecting groups (P=CBZ) at monomers proximate electrodes 2, 3, 5, 6, and 7 and counter electrodes 1 and 10.

These two steps result in deprotected reactive amine moieties remaining attached to the leucine molecules at these sites (columns 2, 3, 5, 6, and 7) as illustrated in FIG. 8.

Preparation of the Membrane for Coupling

Figure 9:
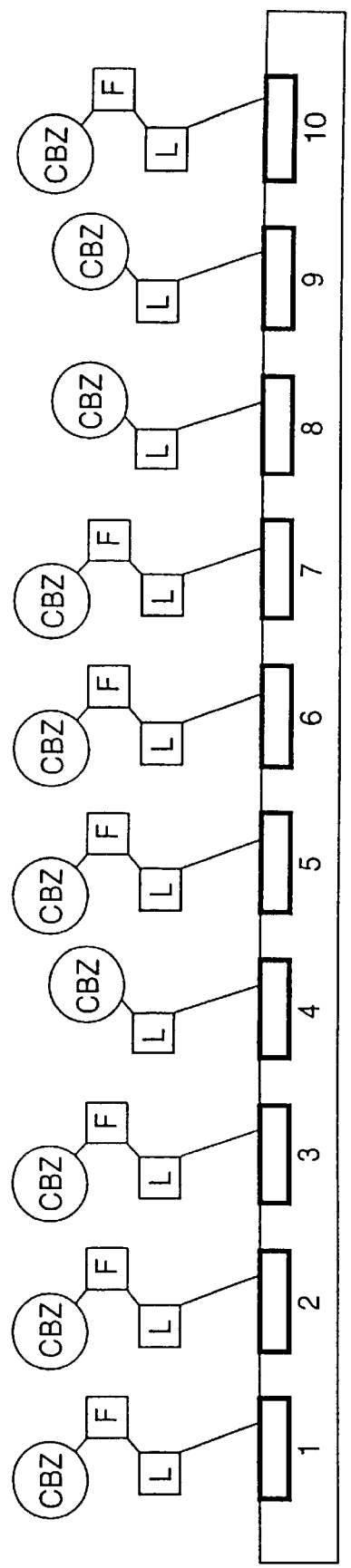
FIG. 9 illustrates modification of monomers proximate electrodes 2, 3, 5, 6, and 7 following CBZ-protected phenylalanine monomers (F) have bonded with the reactive amine functionalities on the leucine monomers proximate these electrodes (a dipeptide is formed).

To prepare the reactive amine moiety covered membrane for coupling CBZ-L-phenylalanine to the deprotected leucine groups, the following steps are performed:

The electrode array containing the reactive amine moiety covered membrane is washed twice with pure DMF. The electrode array is then exposed to a DMF solution containing CBZ-L-phenylalanine and coupling reagents, such as DCC room temperature for approximately two hours. This step results in the electrodes of columns 2, 3, 5, 6, and 7 being modified with an CBZ-protected dipeptide of leucine and phenylalanine. This is shown in FIG. 9.

Figure 10:
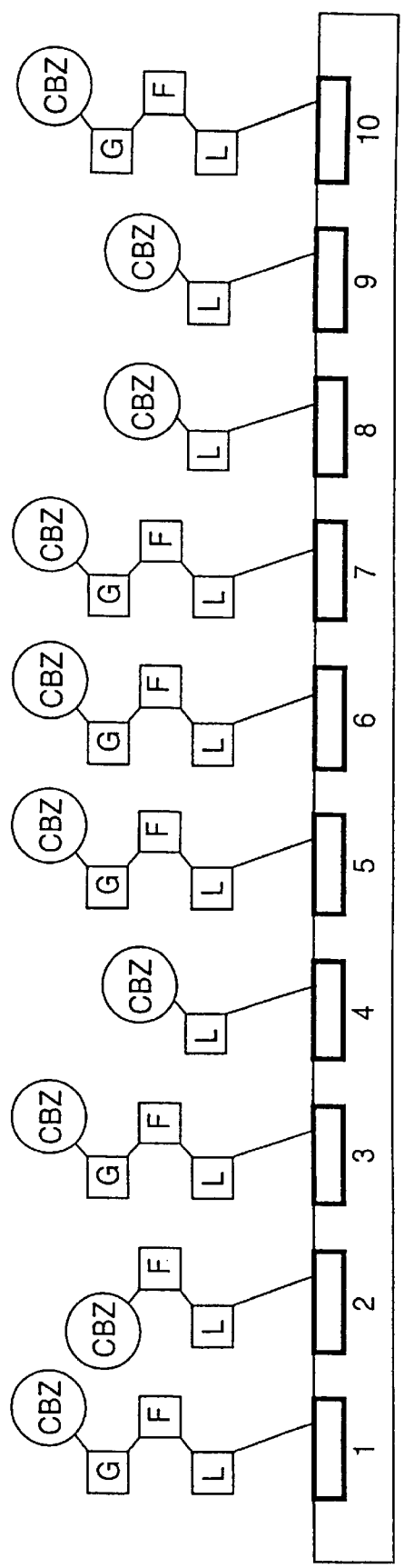
FIG. 10 illustrates modification of the substrate surface by CBZ-projected tripeptides, glycine-phenylalanine-leucine (G-F-L) proximate electrodes 3, 5, 6, and 7.

The deprotection and coupling steps are then repeated at columns 3, 5, 6, and 7. That is, the electrode array is again exposed to an aqueous 0.1 M phosphate buffer solution having a pH of 7.4. The electrode array is then exposed to a DMF solution of CBZ-protected glycine and coupling reagents for approximately 2 hours at room temperature. This results in the electrodes in columns 3, 5, 6, and 7 being modified with the CBZ-protected tripeptide glycine-phenylalanine-leucine (G-F-L), as shown in FIG. 10.

The deprotection and coupling steps are then repeated at columns 5, 6, and 7. That is, the electrode array is again exposed to an aqueous 0.1 M phosphate buffer solution having a pH of 7 4 and then exposed to a DMF solution of CBZ-protected glycine and coupling reagents for approximately two hours at room temperature. This results in the electrodes in columns 5, 6, and 7 being modified with the CBZ-protected tetrapeptide glycine-glycine-phenylalanine-leucine (G-G-F-L).

Figure 11:
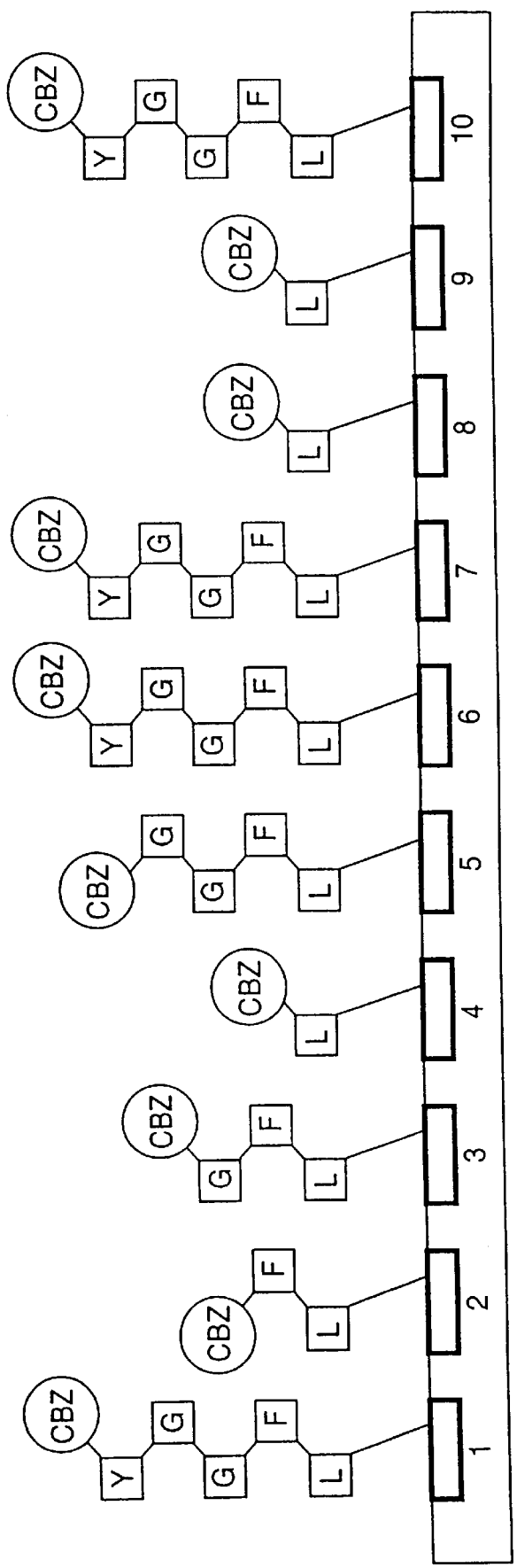
FIG. 11 illustrates modification of the substrate surface by CBZ-protected pentapeptides, tyrosine-glycine-glycine-phenylalanine-leucine (Y-G-G-F-L) proximate electrodes 6 and 7.

The deprotection and coupling steps are then repeated at columns 6 and 7 while the electrode array is again exposed to an aqueous 0.1 M phosphate buffer solution having a pH of 7.4. The electrode array is then exposed to a DMF solution of DBZ-protected 1-tyrosine and coupling reagents for approximately two hours at room temperature. This results in the electrodes in columns 6 and 7 being modified with the CBZ-protected pentapeptide tyrosine-glycine-glycine-phenylalanine-leucine (Y-G-G-F-L), as shown in FIG. 11. This is the CBZ-protected version of the desired Leu-enkephalin epitope.

The deprotecting step is then repeated at columns 2, 3, 5, and 6, without a preconditioning step, to remove the CBZ protecting groups from the terminal amino acids of the combinatorial sequences. This procedure produces the following sequences:

Columns 1 and 10: modified with the protected Leu-enkephalin epitope (these are the counter electrodes).

Column 2: modified with the deprotected dipeptide F-L.

Column 3: modified with the deprotected tripeptide G-F-L.

Columns 4, 8 and 9: modified with the CBZ-protected leucine amino acid.

Column 5: modified with the deprotected tetrapeptide G-G-F-L.

Column 6: modified with the deprotected Leu-enkephalin epitope.

Column 7: modified with the CBZ-protected Leu-enkephalin epitope.

3-E7 Monoclonal Antibody Assay

Figure 12:
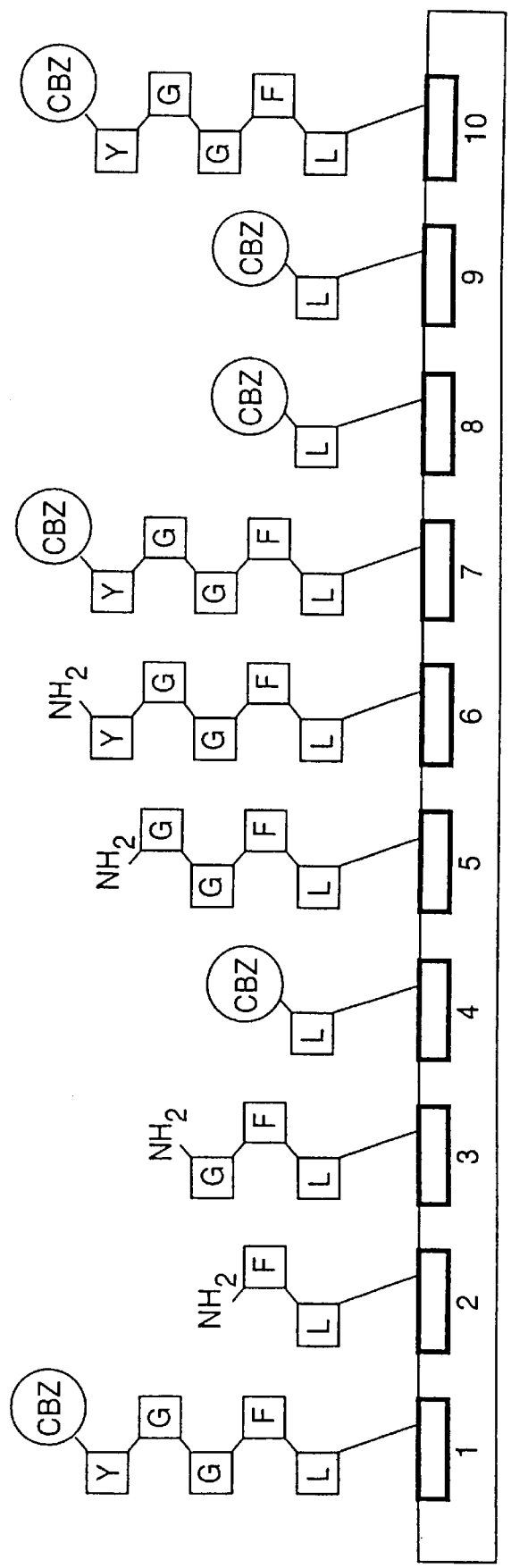
FIG. 12 illustrates a protected leu-enkephalin epitope proximate electrode 7 and counter electrodes 1 and 10, and a deprotected leu-enkephalin epitope proximate electrode 6.
Figure 13:
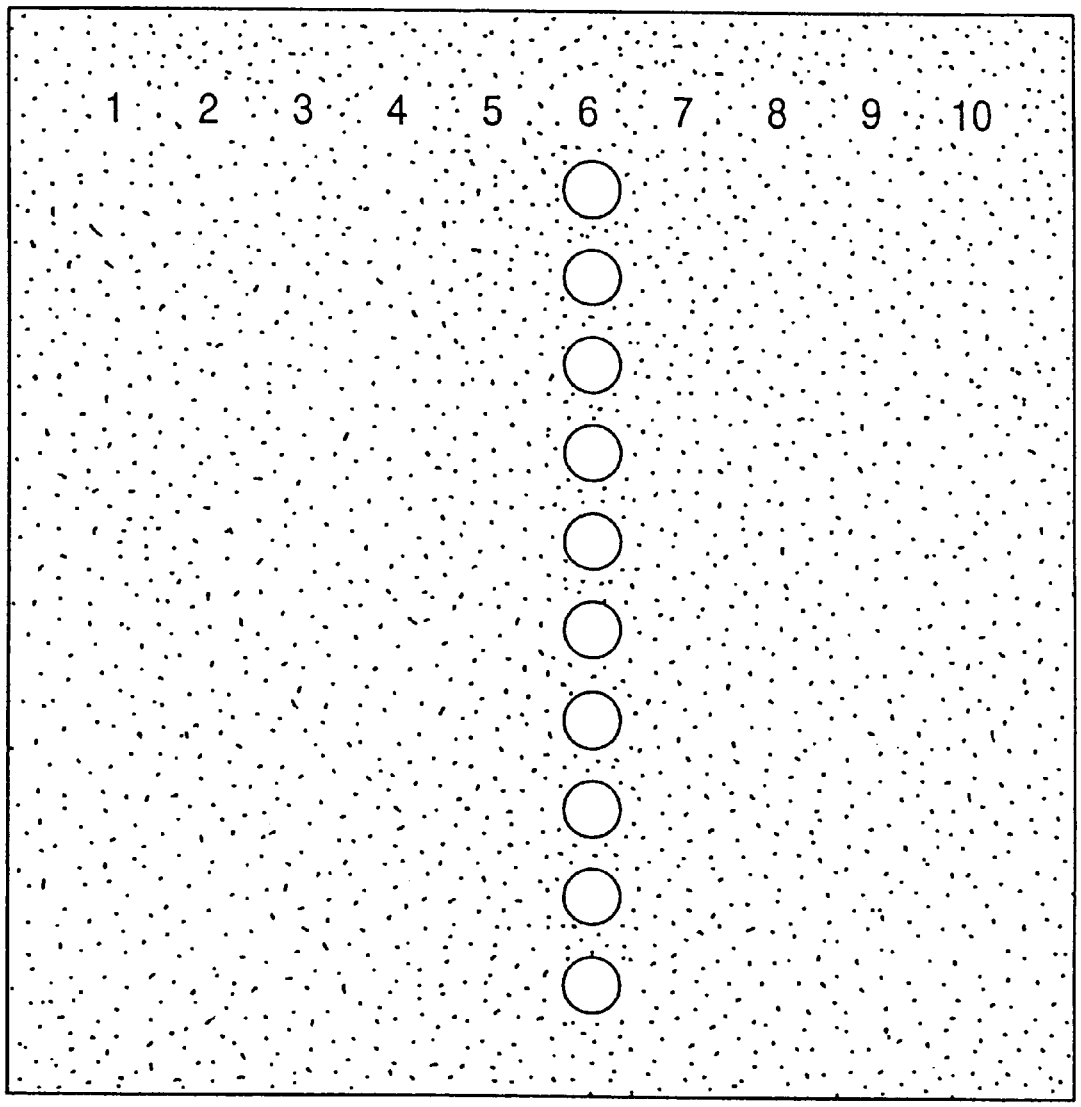
FIG. 13 illustrates representative results as would be observed using an epifluorescent microscope following exposure to the antibody and fluorescent conjugate in accordance with Example 1.

The modified electrode array, i.e., with the 10 modified columns, is exposed, via the Leu-enkephalin epitope detection technique discussed above, to the 3-E7 monoclonal antibody, followed by exposure to the goat anti-mouse fluorescent conjugate. The electrode array is then examined using an epifluorescent microscope. The expected results are shown in FIGS. 12 and 13. As is shown in FIGS. 12 and 13, the active Leu-enkephalin epitope is present proximate to the electrodes of column 6. (Column 6 is the only column modified with the deprotected Leu-enkephalin epitope).

Note: The synthesis proceeds at the counter electrodes (electrodes 1 and 10) because protons are generated at the counter electrodes during each preconditioning (deprotecting) step. Since a preconditioning step is not performed in the final deprotection step, no protons are produced at the counter electrodes in the final step and a protected Leu-enkephalin epitope is produced at the counter electrodes, which does not react upon exposure to the antibody and fluorescent conjugate.

Example 2

Combinatorial Synthesis of Deoxyribonucleic Acids

Background

The monomer units for combinatorial synthesis of DNA are called phosphoramidites. Phosphoramidites are linked together into a single strand nucleic acid polymer through phosphodiester bonds. Since the phosphorus is protected by a cyanoethyl ether moiety during synthesis, the bonds are phosphotriester bonds. The cyanoethyl group can be removed by a base at the end of synthesis to give the phosphodiester linkage. Phosphoramidites have two ends that are called 3' and 5' ends. The 3' end of one phosphoramidite will couple with the 5' end of another. Usually the 3' end is attached to a solid support and the 5' end is modified by another phosphoramidite to start the synthesis cycle. The 5' end is a hydroxy group that can be protected by a molecule called dimethyltrityl (DMT). DMT groups are acid labile protecting groups.

There are four naturally occurring deoxyribonucleotide monomers that form DNA polymers. They are adenosine (A), thymidine (T), cytosine (C), and guanosine (G). DNA is considered an acid because the phosphodiester groups that bind the monomers together are acidic. The nucleosides (A,T,C,G) are organic bases. DNA in nature is normally tens of millions to billions of base units long. A fifteen base unit long piece of DNA will be prepared in the following example. A piece of DNA of this length is known as a oligonucleotide. DNA molecules should be at least this long, otherwise it is very difficult to distinguish between them.

The nucleosides are protected because the exocyclic amine bases (A, C, G) are susceptible to depurination by acids. The protecting groups on these bases are base labile. There are three kinds of protecting groups on phosphoramidites. They are the DMT groups, which protect the 5' hydroxyl groups, the cyanoethyl ether groups, which protect the phosphorus, and the FOD (fast oligonucleotide deprotection) groups, which protect the exocyclic amines on the nucleoside bases. The DMT groups are acid labile and the others are base labile.

DNA is found in nature mostly as the "duplex" form having the famous double helix structure. This means that two single strands of DNA are bound together by interactions between the nucleoside bases. The nucleoside base T interacts with the nucleoside base A to form an A-T linkage. The nucleoside base C interacts with the nucleoside base G to form a C-G linkage. The A-T and the C-G interactions are the only stable interactions; other combinations are weak. Linkages that are not A-T or C-G can occur, and are called mismatches. When two complimentary single strands of DNA come together to form a duplex, this is called hybridization. When the single strands of DNA in a duplex come apart, the duplex DNA is said to have denatured. DNA duplexes typically denature when they are exposed to heat and/or low ionic strength aqueous solutions.

To determine whether or not a specific DNA sequence has been synthesized at a particular site, one uses probe strands of DNA that are complimentary with the strands that presumably were synthesized at that site. These probe strands are labeled covalently with a fluorescent dye. The probe strands will bind to DNA molecules on the surface with both the correct sequence and the incorrect sequence. However, the melting temperatures are much lower for the DNA duplexes that contain mismatches, i.e., non A-T and C-G links, than those that are complimentary, i.e., A-T and C-G links. Thus, upon heating, the probes forming duplexes with the incorrect DNA strands will denature first. By increasing the temperature to a level where all of the mismatched DNA duplexes have denatured, it is possible to detect only the DNA molecules wit the correct sequence by observing the fluorescent dye using epifluorescent microscopy. Alternatively, the test surface can be washed with low ionic strength aqueous solutions. This has the same effect as raising the temperature and is more convenient experimentally.

Synthesis Procedure

The electrode array is first modified with an acrylate/polyvinyl alcohol copolymer layer or membrane. The copolymer layer contains numerous pendant hydroxyl groups that are reactive toward phosphoramidites. The polymer modified electrode array is then exposed to DMT-protected cytidine phosphoramidite and tetrazole at a concentration of 0.05 M in an anhydrous acetonitrile for 30 seconds at room temperature. The cytosine base and all of the other bases used in this example are protected using the FOD protecting scheme. (FOD protecting groups afford the best protection against depurination of exocyclic amines.) The array is then washed with anhydrous acetonitrile. Any unreacted hydroxyl groups on the surface are then capped by exposing the surface to an anhydrous acetonitrile solution of acetic anhydride and 1-methylimidizole for thirty seconds. This results in a surface modified everywhere with DMT protected C base units.

The trivalent phosphite linkage between the polymer and the phosphoramidite is oxidized to the more stable pentavalent phosphotriester linkage by electrochemically generated iodine. The iodine is produced electrochemically by the oxidation of iodide ions in an aqueous THF solution of potassium iodide. Iodine can be confined to the local area where it is formed by both an iodine buffering reaction and a scavenging reaction. Iodine is buffered by an equilibrium reaction with iodide ions to form the triiodide ion. The triiodide ion is not a useful reagent. Further, the solution can be buffered with respect to hydroxyl ions such that it is slightly basic. Iodine reacts with hydroxyl ions to form iodide ions and hypoiodite. Both of these chemical species are unreactive. Thus, hydroxyl ions serve as scavengers for iodine. Because the electrochemical oxidation of iodide ions to iodine can occur under conditions that also produce protons, the local environment can be made acidic while the iodine is being generated. There will be no scavenging in the acidic regions where iodine needs to be active. As a result, there are stable phosphodiester linkages to the polymer film only over those electrodes that electrochemically generate iodine. The unoxidized phosphite linked groups will eventually fall off after repeated exposure to the acidic anhydride capping solution.

The electrode array is next exposed to an aqueous 0.1 M sodium phosphate solution. A positive potential is applied for one second to first selected areas and the DMT protecting groups are removed from the cytidine phosphoramidites in first selected areas. The array is then washed with anhydrous acetic anhydride. The reactive array is then exposed to a 0.05 M solution of thymidine phosphoramidite, T, and tetrazole in anhydrous acetonitrile for 30 seconds. The T nucleotides react with the C nucleotides at the first selected sites to form a C-T dimer. The remaining unreacted C nucleotides are capped and the phosphite linkages are reduced to phosphotriester linkages as outlined above.

This procedure is repeated at second, third, fourth, and so on, selected sites to synthesize combinatorially four different fifteenmer oligonucleotides at selected sites on the array. The array is then exposed to a 0.1 M aqueous ammonium hydroxide solution at 50° C. for an hour. The FOD protective groups and the cyanoethyl protecting groups on the phosphotriester are removed by the hydroxyl ions. The resulting array consists of single strands of the oligomer nucleic acids bound covalently to the polymer membrane.

Evaluation of the Fidelity of the Array

The fidelity of the combinatorial array is tested using four different fluorescently labeled oligonucleotide probes that are complimentary to the oligonucleotides synthesized on the array. The array is exposed to a first 100 nanomolar solution of a fluorescently labeled oligonucleotide probe in a 0.1 M sodium phosphate buffer at pH 7.2 at room temperature for thirty minutes. The array is then washed three times with a 0.1 M sodium phosphate buffer solution at pH 7.2. The array is then examined with an epifluorescent microscope. Bright spots appear in first areas where the oligonucleotide probe is present. To ensure that the oligonucleotide probe and its compliment actually hybridized, the array is washed several times with deionized water at 70° C. for five minutes. Reexamination of the array with the epifluorescent microscope reveals a dark field. This means that the probe hybridized to its compliment and the results are not due to nonspecific absorption. The array is then exposed to a second 100 nanomolar solution of another fluorescently labeled oligonucleotide probe in 0.1 M aqueous sodium phosphate buffer at pH 7.2. The array is subsequently washed, examined with the epifluorescent microscope and then checked for nonspecific absorption. Bright spots appear in the second areas where the nucleotide probes are synthesized. The procedure is repeated for the third and fourth oligonucleotide sequences. The control areas will not bind the fluorescently labeled probe and become bright at any point in the assay.

Example 3 and Comparative Example 4

For the following example and comparative example, results were recorded and reproduced in the form of video photomicrographs that were captured digitally of the respective electrode array chips under various conditions.

Recording of Results—Taking of Pictures

The photomicrographs were taken using an Olympus BX60 microscope with a Pulnix TM-745 integrating CCD camera. The camera was controlled by, and the images were captured by, a Data Translation DT3155 video capture card run by a Pentium-based personal computer. The software that controlled the DT3155 card can easily be written by one of ordinary skill in the art.

Most of the photomicrographs were taken with a 10× objective that allowed approximately 16 electrodes to be seen in each image; however, for purposes of evaluation, the images were sometimes cropped to focus on the activity of the electrodes of interest. At times, a 4× objective was also used. Two types of photomicrographs were taken. A few were taken using white light illumination. In these, the electrodes appear reflective. For example, see FIG. 14. The majority of the photomicrographs were taken using epifluorescent illumination. In these, the electrodes appear dark in the photomicrographs when they are uncoated, i.e., when no fluorescent coating is present, because the metal of the electrodes, e.g., the platinum, quenches any fluorescence present.

Epifluorescent micrscopy involves illuminating the electrode array chip from a position above the chip surface, along a path normal to the chip surface. The illuminating beam is filtered to obtain a narrow band centered at the excitation wavelength of the fluorescent dye being used. The fluorescent dye used in the following example and comparative example was Texas Red, which has an absorption maximum at 595 nm. This dye emits a fluorescent light with an emission maximum of 615 nm when it is excited with light of approximately 595 nm. Texas Red can be obtained from Molecular Probes, Eugene Oreg. Filters in the Olympus BX60 microscope prevent the excitation light from traveling to the optical detector of the CCD camera. The Olympus BX60 microscope is equipped with an ancillary art-recognized instrumentation module to perform epifluorescent microscopy using Texas Red dye.

Figure 14:
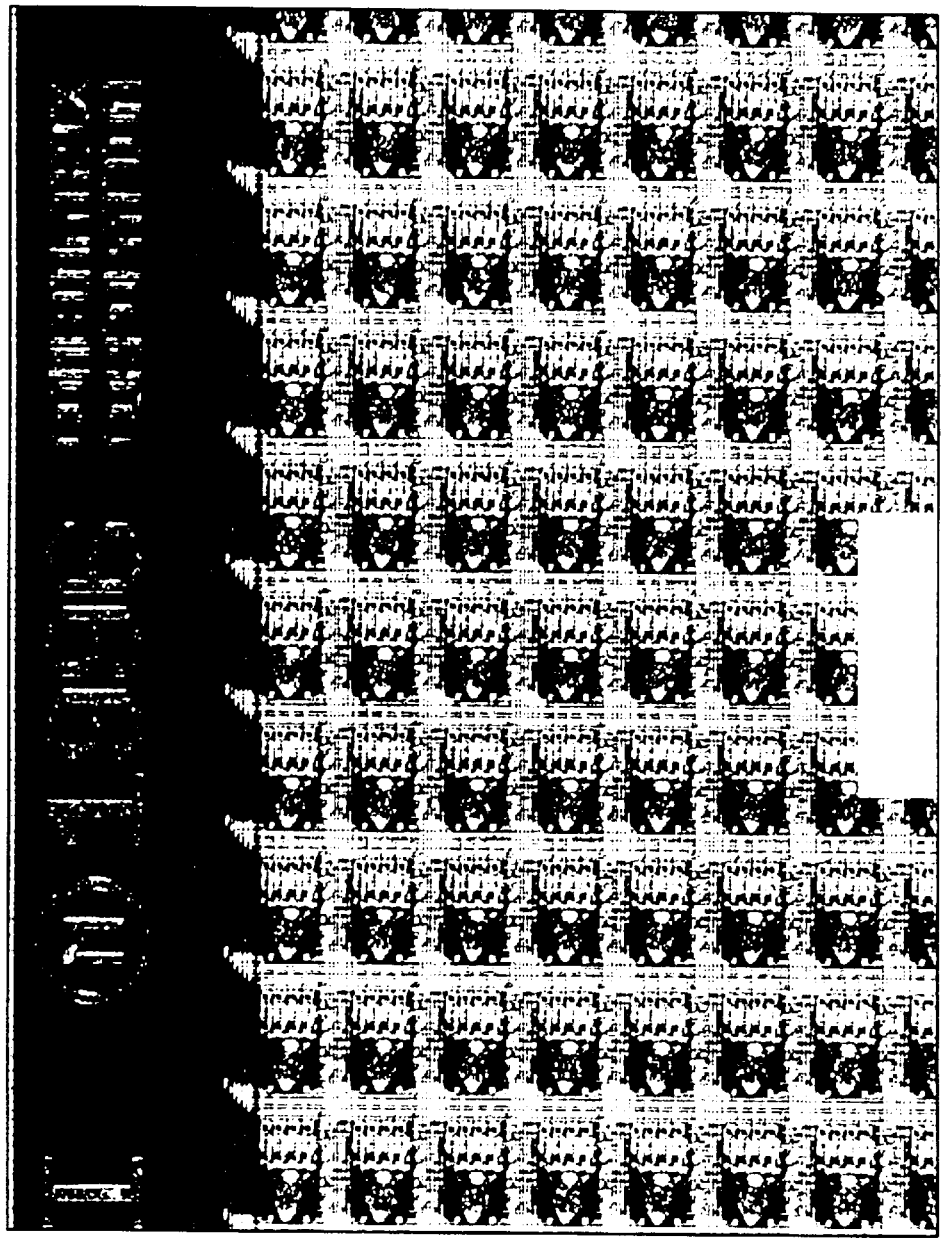
FIG. 14 is a digitally captured white light photomicrograph of an uncoated electrode array chip showing a approximately seventy electrodes. This photomicrograph was taken using a 4 x objective by an Olympus BX60 microscope with a Pulnix TM-745 integrating CCD camera. Note, there is no electrical circuitry associated with these independently addressable electrodes.
Figure 15:
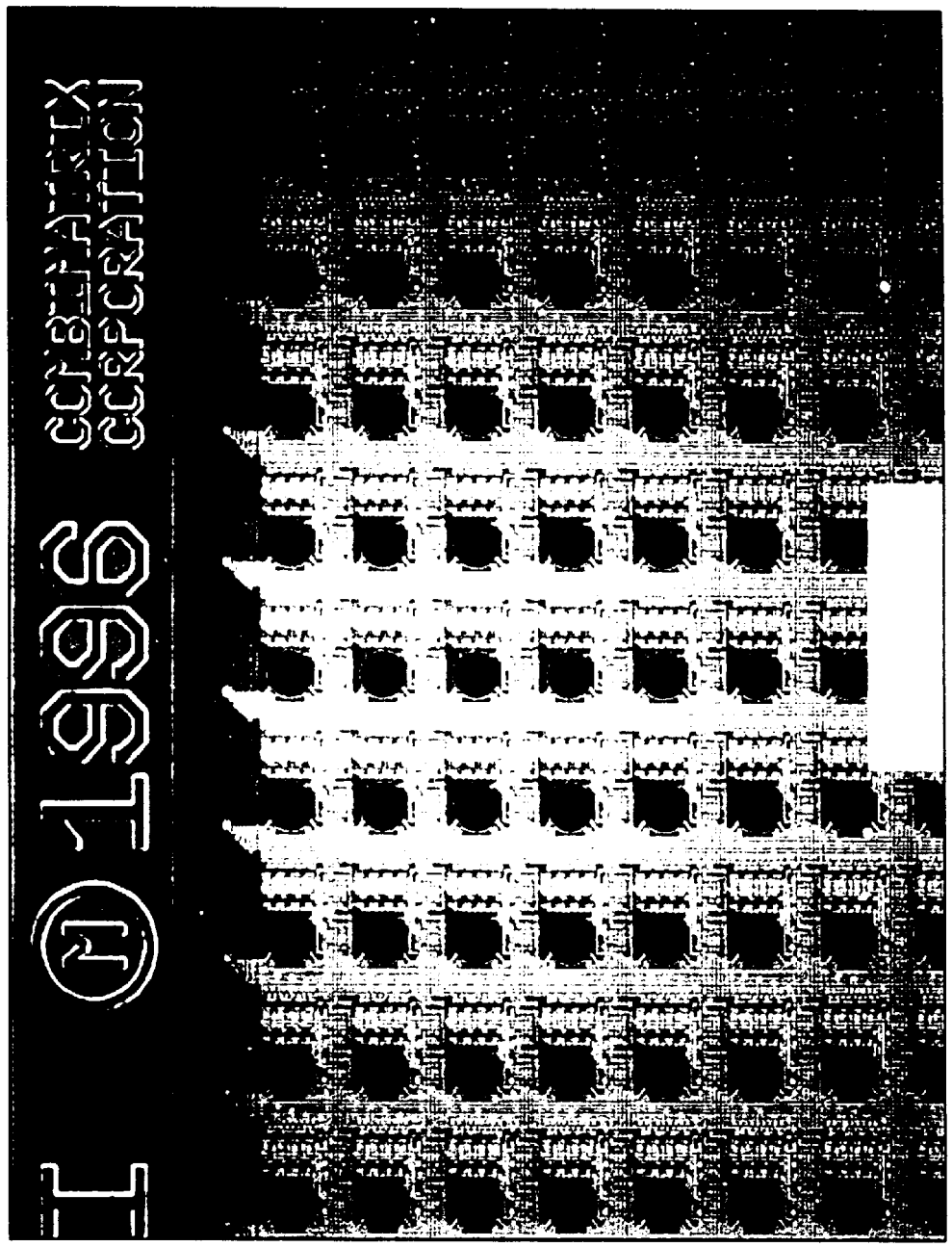
FIG. 15 is a digitally captured epifluorescent photomicrograph of the same array of electrodes pictured in FIG. 14, at the same magnification. This photomicrograph shows that on an uncoated electrode array chip, without any fluorescent coating material thereon, the electrodes are dark. The darkness of the electrodes is explained by the metal of the electrode (platinum) quenching any fluorescence present.
Figure 16:
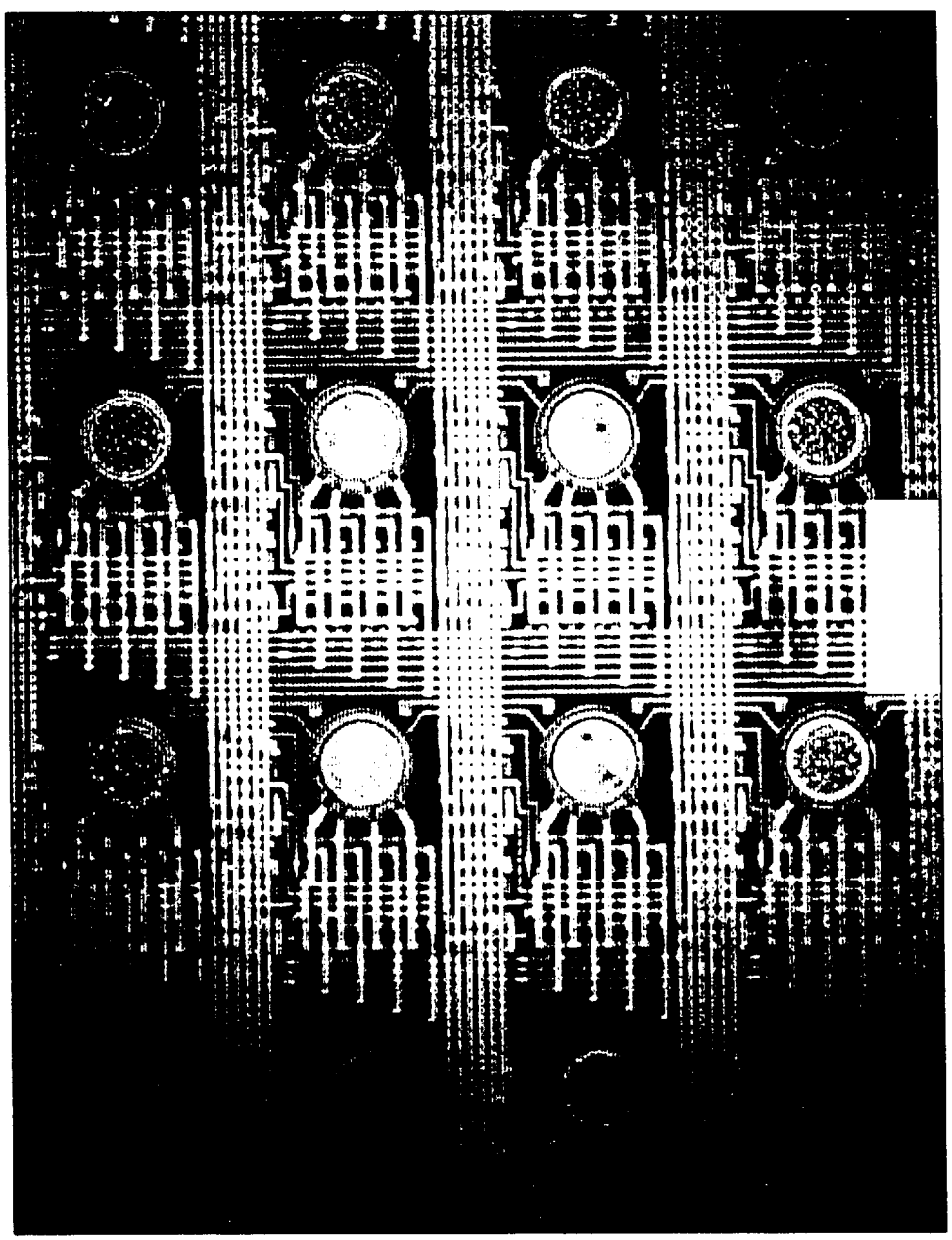
FIG. 16 is a digitally captured epifluorescent photomicrograph of electrodes in the same array as in FIGS. 14 and 15, but taken using a 10 x objective and showing only sixteen electrodes. This photomicrograph is of a chip that is coated with a fluorescent membrane material, i.e., there are fluorescent labeled molecules attached to a membrane overlaying the electrodes. This photomicrograph shows that when the electrodes are coated with a membrane containing florescent material, the area proximate/over the electrodes is bright. The fluorescent material used for this photomicrograph was streptavidin molecules labeled with Texas Red dye.

Exemplary photomicrographs taken using white illumination and epifluorescent illumination are shown in FIGS. 14–16. FIGS. 14 and 15 depict an uncoated electrode array chip, while FIG. 16 depicts an electrode array chip coated with a fluorescent membrane.

Description and Preparation of the Electrode Array Chips

The chips prepared and used in the following example and comparative example were rectangular devices with a 16 (in the x-direction) by 64 (in the y-direction) array of 100 micron diameter platinum electrodes. The total number of electrodes in these arrays was 1024. The dimensions of the chips were approximately 0.5 cm (x-direction) by 2.3 cm (y-direction), and the total surface area of the chips was approximately 1 square centimeter. The electrodes in each array were approximately 250 microns apart in the x-direction and approximately 350 microns apart in the y-direction, measured from the center of the electrodes.

Each electrode in the array was capable of being addressed independently using an SRAM cell (static random access memory), a standard art-recognized way to address independently electric circuitry in an array. The SRAM cell was located next to the electrodes in the electrical circuitry associated with electrode. Each electrode in the array had four separate switchable voltage lines that attached to it, allowing each electrode in the array to be switched independently from one voltage line to another. The voltage was arbitrary and was set by an external voltage source.

Figure 17:
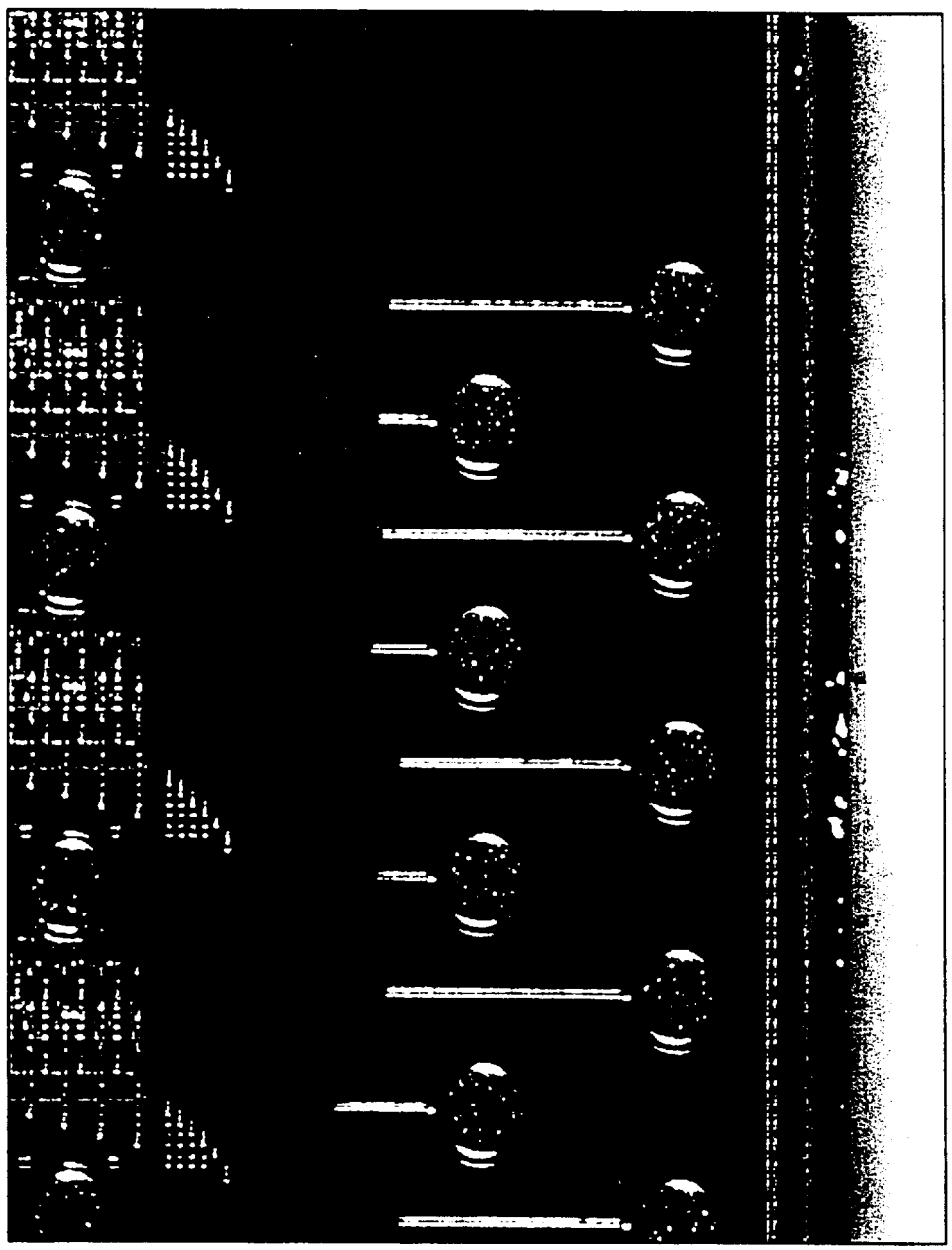
FIG. 17 is a digitally captured white light photomicrograph similar to FIG. 14, except that these electrodes are hard wired, as shown by the leads connecting the electrodes to the electrical source located off the micrograph. In addition, this photomicrograph was taken using a 10 x objective. These hardwired electrodes are located on the side of the electrode array chips. Note, there is no circuitry associated with these hard wired-electrodes.

In the chips used in the following examples and comparative example, there were additionally 13 electrodes on the side of the chips that were hard wired to bond pads, meaning they were not switchable or independently addressable as were the electrodes in the 16×64 array. These 13 electrodes had no circuitry associated with them except for a single voltage line, and thus allowed protocols to be run on them without engaging the associated electrode array. These 13 electrodes were 100 microns in diameter and were spaced differently from the electrodes in the array. See, for example, FIG. 17, showing the triangular orientation of the hard-wired electrodes, wherein the electrodes are 250 microns apart from the centers of the electrodes.

The chips were made by a 3 micron process using hybrid digital/analog very large scale integration (VLSI). One skilled in the art would be familiar with such a process and could easily prepare a chip for use in accordance with the present invention. See, Mead, C., *Analog VLSI and Neural Systems, Addison Wesley* (1989). The circuitry used was CMOS (complimentary metal-oxide silicon) based and is also well known to those of ordinary skill in the art.

The chips were controlled by at least one Advantech PCL-812 digital I/O card (in the computer) that was driven by a Pentium based personal computer. These digital I/O cards can be obtained from Cyber Research, Branford, Conn. Preferably the chip is connected through interface hardware, i.e., an interface card, to the I/O card. The software for driving the I/O card can easily be written by one of ordinary skill in the art. DC voltage for powering the chips was provided by the PCL-812 and/or a Hewlett-Packard E3612A DC power supply. Voltage for the electrodes was supplied by the PCL-812 card and/or by an external Keithley 2400 source-measure unit.

Figure 18A:
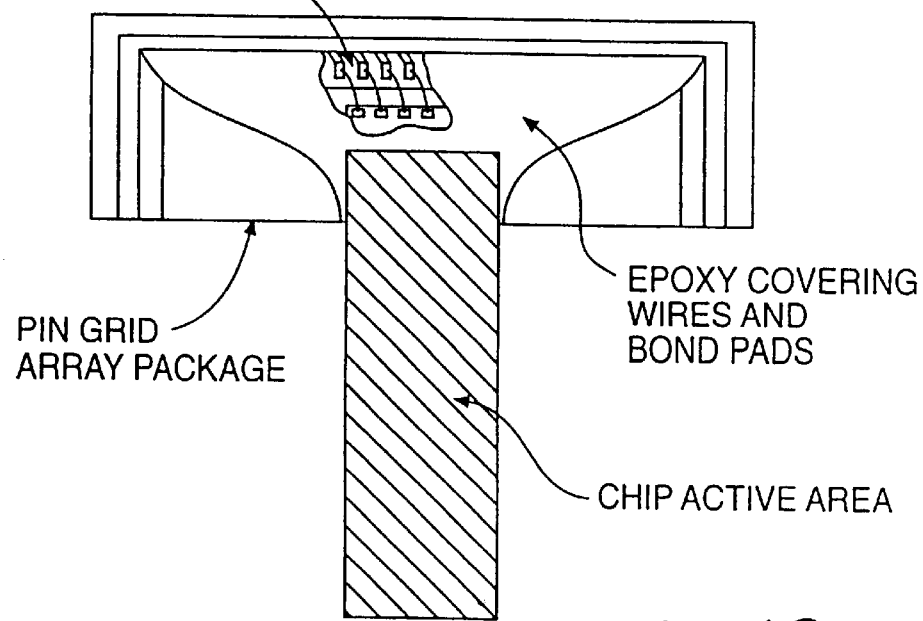
FIGS. 18a and 18b depict the chip/pin grid array (PGA) package assembly.
Figure 18B:
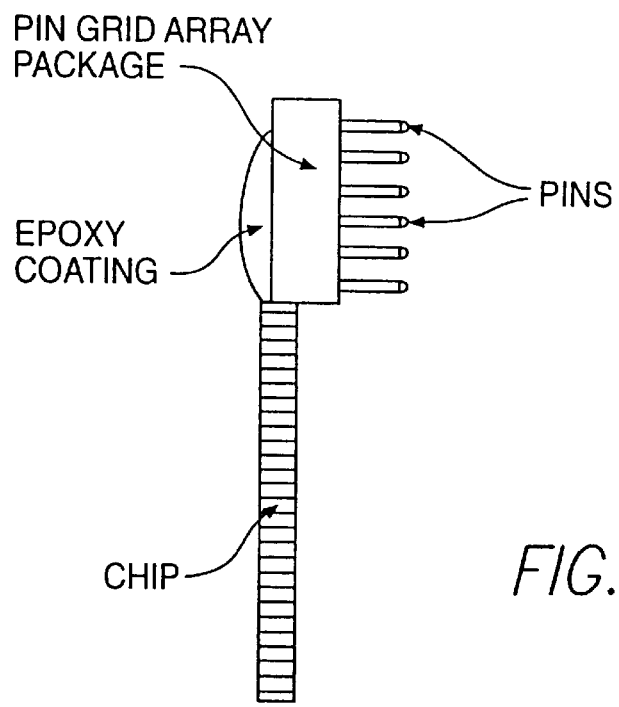

The electrode array chips were designed so that the bond pads for all of the on-chip circuitry were located at one end of the long side of the chips. See FIGS. 18a and 18b. The chips were attached to a standard 121 pin PGA (pin grid array) package that had been sawn in half so that approximately 2 cm of the chip extended out from the end, analogous to a diving board. See FIG. 18b. PGA packages can be obtained from Spectrum Semiconductor Materials, San Jose, Calif. Connecting wires ran between the bond pads on the chip and the contacts (bond pads) on the PGA package. The bond pads on the chip, the connecting wires, and the contacts on the PGA package were covered with epoxy for protection and insulation. See cut away in FIG. 18a. The section of the chips that extended into the air contained the electrode array and was not covered by epoxy. This section of the chips was available for dipping into solutions of interest for chemical synthesis at the electrodes at the surface of the chip. One of ordinary skill in the art could easily set up and design chips appropriate for use in accordance with the present invention.

Example 3

Inventive—Deprotection and Localization

Background Description

One of the above described electrode array chips comprising 16×64 platinum electrodes was used for this example. As indicated above, the chip contained 13 hardwired electrodes located at one end of the long side of the chip, however, these hardwired electrodes were not involved in this example.

The model chemical system used in this example to demonstrate localization and selective deprotection using electrochemically generated reagents involved attaching fluorescent labeled streptavidin molecules, a well-known variety of avidin, obtainable from vector Laboratories, Burlingame, Calif., to a membrane overlaying the electrode array chip via a trityl linker molecule. The overlaying membrane used was polysaccharide-based. The trityl linker molecule used was acid labile, i.e., labile to protons, and detached from the overlaying membrane in the presence of protons, taking with it the attached fluorescent labeled streptavidin molecule. More specifically, the trityl linker molecule used was a modified 4,4'-dimethoxytrityl molecule with an exocyclic active ester obtained from Perseptive Biosystem, Framingham, Mass.

Experimental Procedure

Preparation of the chip for attachment of molecules

To enable the attachment of molecules, in particular trityl linker molecules, to the surface of the electrode array chip for synthesis and/or deprotection proximate the electrodes, the chip was coated/modified with an overlaying membrane of a polysaccharide-based material. Specifically, a polygalactoside was used as the overlaying membrane material in this example. The polygalactoside membrane was dip coated onto the chip. However, dipping or coating according to any method known to one of ordinary skill in the art would be acceptable.

Attachment of the trityl linker molecules

Once the electrode array chip was coated with the polysaccharide membrane, the trityl linker molecules were attached to the chip. The trityl linker molecule used for this example was a modified 4,4'-dimethoxytrityl molecule with an exocyclic active ester, specifically the molecule was N-succinimidyl-4[bis-(4-methoxyphenyl)-chloromethyl]-benzoate. The synthesis and use of this molecule is described in *A Versatile Acid-Labile Linker for Modification of Synthetic Biomolecules*, by Brian D. Gildea, James M. Coull and Hubert Koester, *Tetrahedron Letters*, Volume 31, No. 49, pgs 7095–7098 (1990).

The trityl linker molecules were attached to the polysaccharide membrane via immersion of the polysaccharide membrane coated chip in a DMF solution containing 0.5M of tertbutyl ammonium perchlorate, 0.75M of 2,4,6-collidine and 0.2M of the trityl linker. The immersion of the polysaccharide membrane coated chip in the DMF linker solution lasted for 30 minutes at ambient temperature. The trityl linker coated chip was then washed with DMF to remove any remaining reactants. Next, the trityl linker coated chip was washed in an aqueous 0.1 M sodium phosphate buffer that was adjusted to pH 8.0, and dried.

Attachment of the fluorescent dye labeled molecules

The trityl linker coated chip was then immersed in an aqueous solution of fluorescent dye (Texas Red) labeled streptavidin molecules having a concentration of 50 micrograms per milliliter and allowed to remain in this solution for one hour at ambient temperature. During this immersion, the linker molecule was derivatized and the fluorescent dye labeled streptavidin molecules were attached to the linker molecules.

The chip containing fluorescent dye labeled streptavidin molecules was then washed with an aqueous 0.1M sodium phosphate buffer that was adjusted to pH 8.0 to remove remaining reactants, and dried. The chip was now ready for use in the electrochemical process of the invention, i.e., the selective deprotection step.

Figure 19A:
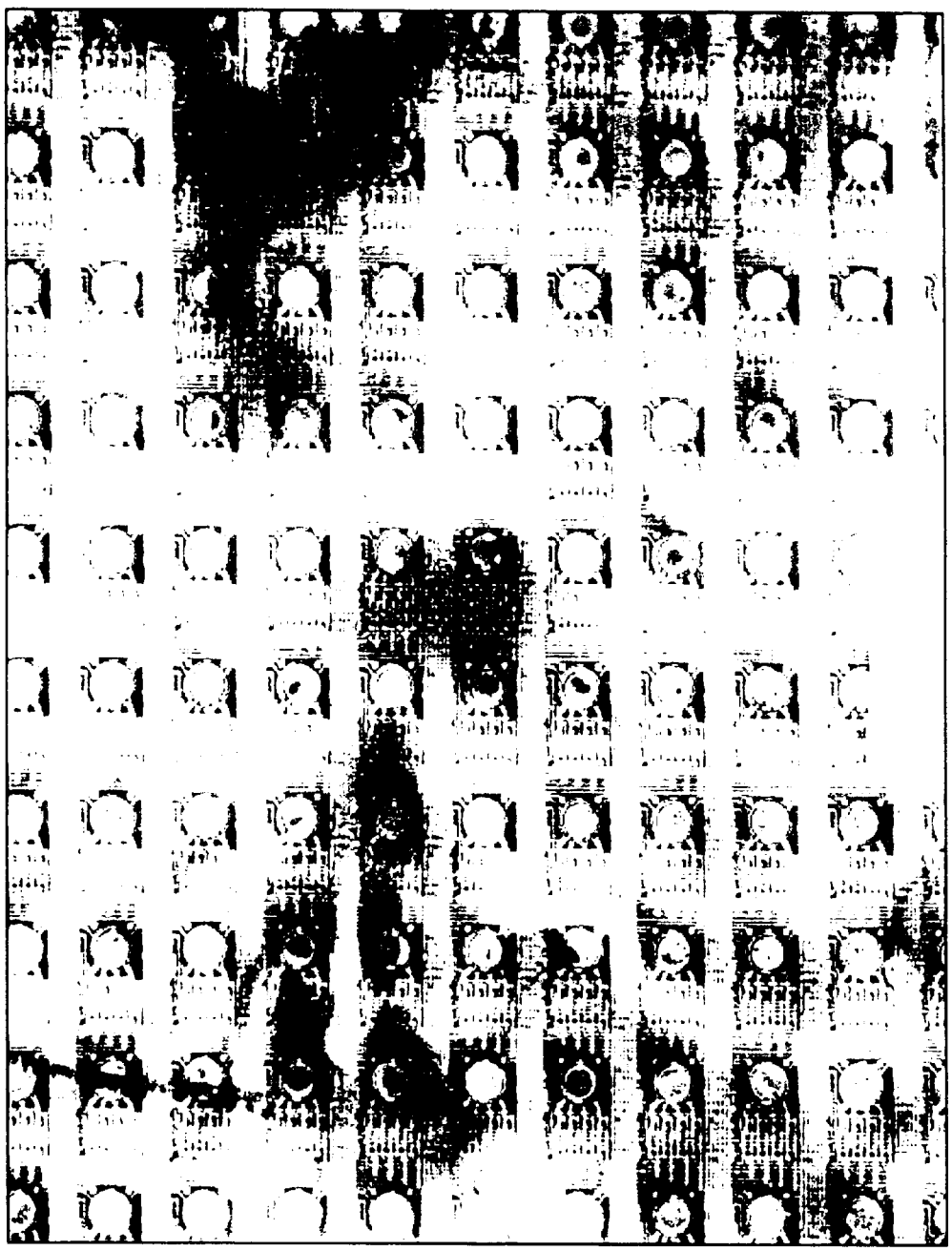
FIGS. 19a and 19b represent digitally captured epifluorescent photomicrographs showing an electrode array chip before (FIG. 19a) and after (FIG. 19b) application of voltage and performance of a deprotection step. Prior to application of any voltage, a 0.05M aqueous sodium phosphate buffer at a pH of 8.0 was placed in contact with all the electrodes of the array to enable production of electrochemical reagents.
Figure 19B:
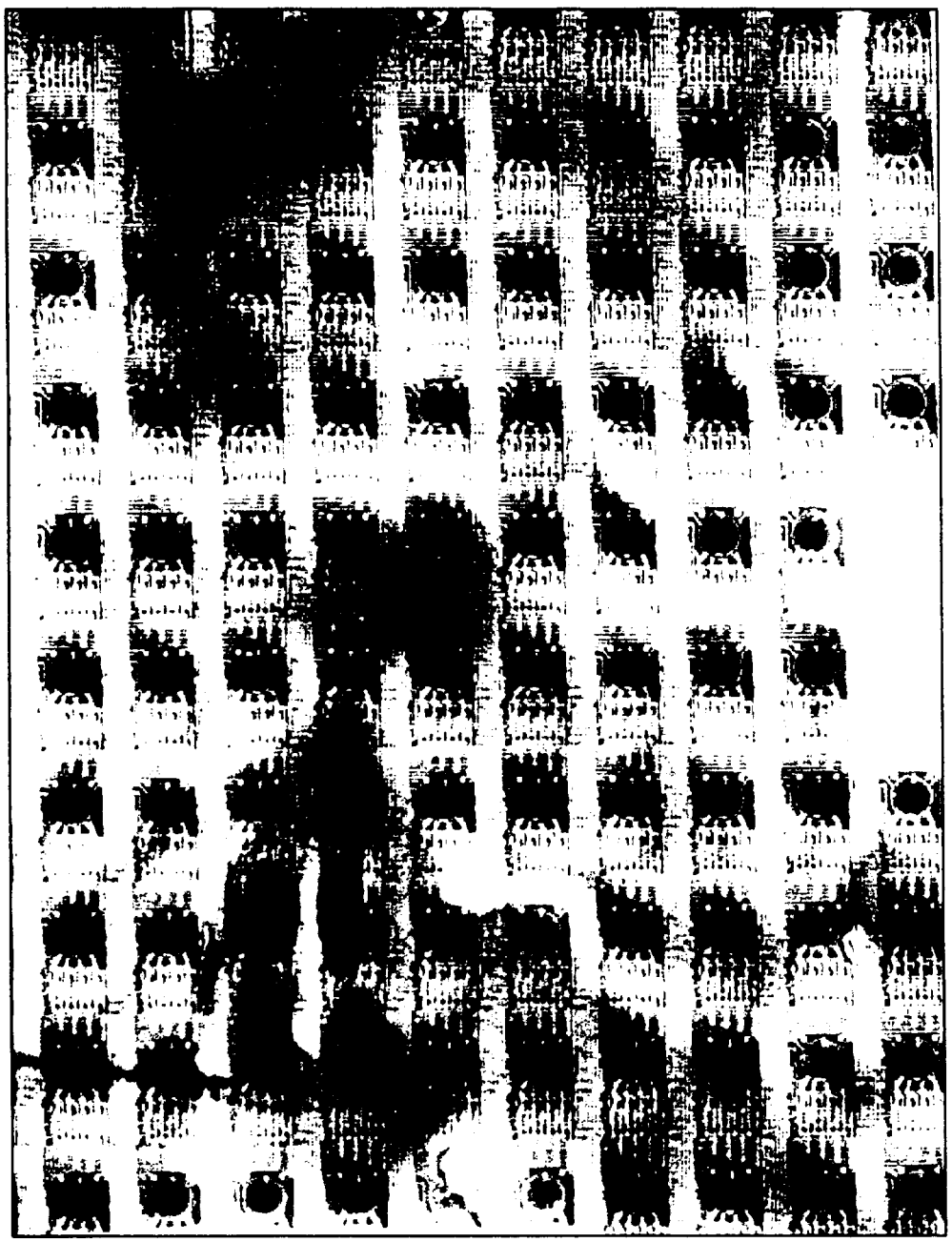

Following exposure of the prepared chip to the fluorescent labeled streptavidin molecules, but prior to any electrical current or voltage being applied, the electrodes in the array were all bright with fluorescence because the membrane proximate to them contained the fluorescent labeled streptavidin molecules bound to the membrane via the trityl linker. A photomicrograph of this is shown in FIG. 19*a*.

Selective Deprotection

To perform the selective deprotection step, the prepared chip was immersed in a 0.05M aqueous sodium phosphate buffer solution to enable electrochemical generation of reagents. A voltage difference of 2.8 volts was applied to select electrodes (alternating in a checkerboard pattern) for approximately 10 minutes, causing protons to be generated electrochemically at the anodes.

After the protons were electrochemically generate at the anodes, the anodes became dark because the trityl linker previously bound proximate to the anodes dissociated from the anodes and the fluorescent labeled streptavidin molecules were washed away. The extent to which this occurred at the anodes and not at the cathodes in the checkerboard pattern, is a measure of the chemical crosstalk occurring between the electrodes in the array. That is, if chemical crosstalk were occurring, the cathodes would also be dark because the protons would have migrated and dissociated the trityl linkers at the cathodes.

Thus, under epifluorescent microscopy, the bright electrodes (cathodes) indicate the presence of a Texas Red labeled streptavidin molecule bound to a linker molecule at the electrode and the dark electrodes (anodes) indicate the lack of a Texas Red labeled streptavidin molecule bound to a linker molecule at the electrode. This is shown in FIGS. 20 and 21, FIG. 20 having been taken using a 4× objective with an integration time of 2 seconds, and FIG. 21 having been taken using a 10× objective with a 500 millisecond integration time.

Results

Figure 20:
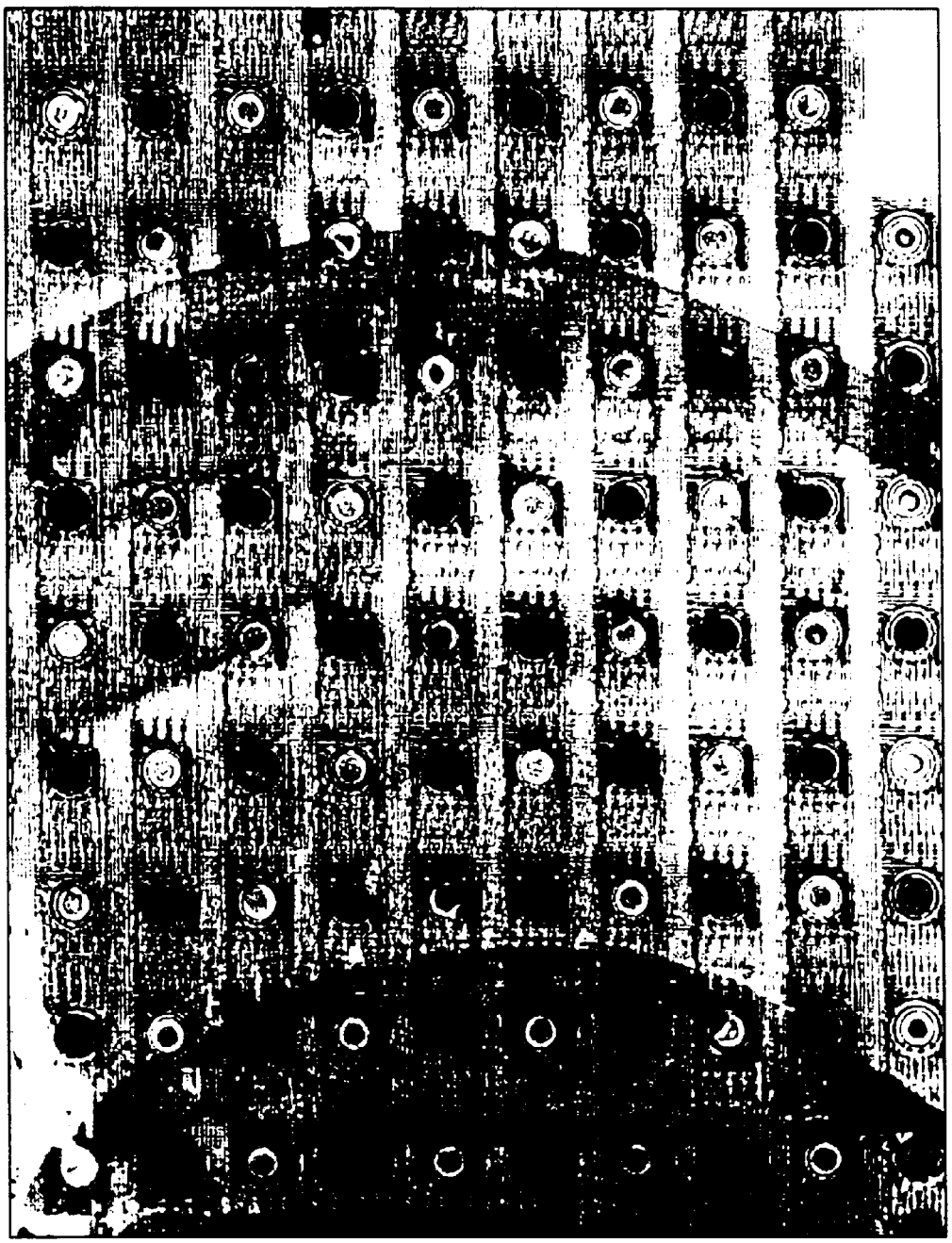
FIG. 20 represents a digitally captured epifluorescent photomicrograph showing a hardwired electrode array chip wherein the anodes (the dark electrodes) and the cathodes were alternating electrodes. The depicted checkerboard pattern was obtained following application of 2.8 volts for 10 minutes. The objective used to obtain this photomicrograph was 4x and the integration time was 1 second. Note, the localization of the acid at the anodes. The precision of the localization achieved in accordance with the present invention allowed the checkerboard pattern to be obtained.
Figure 21:
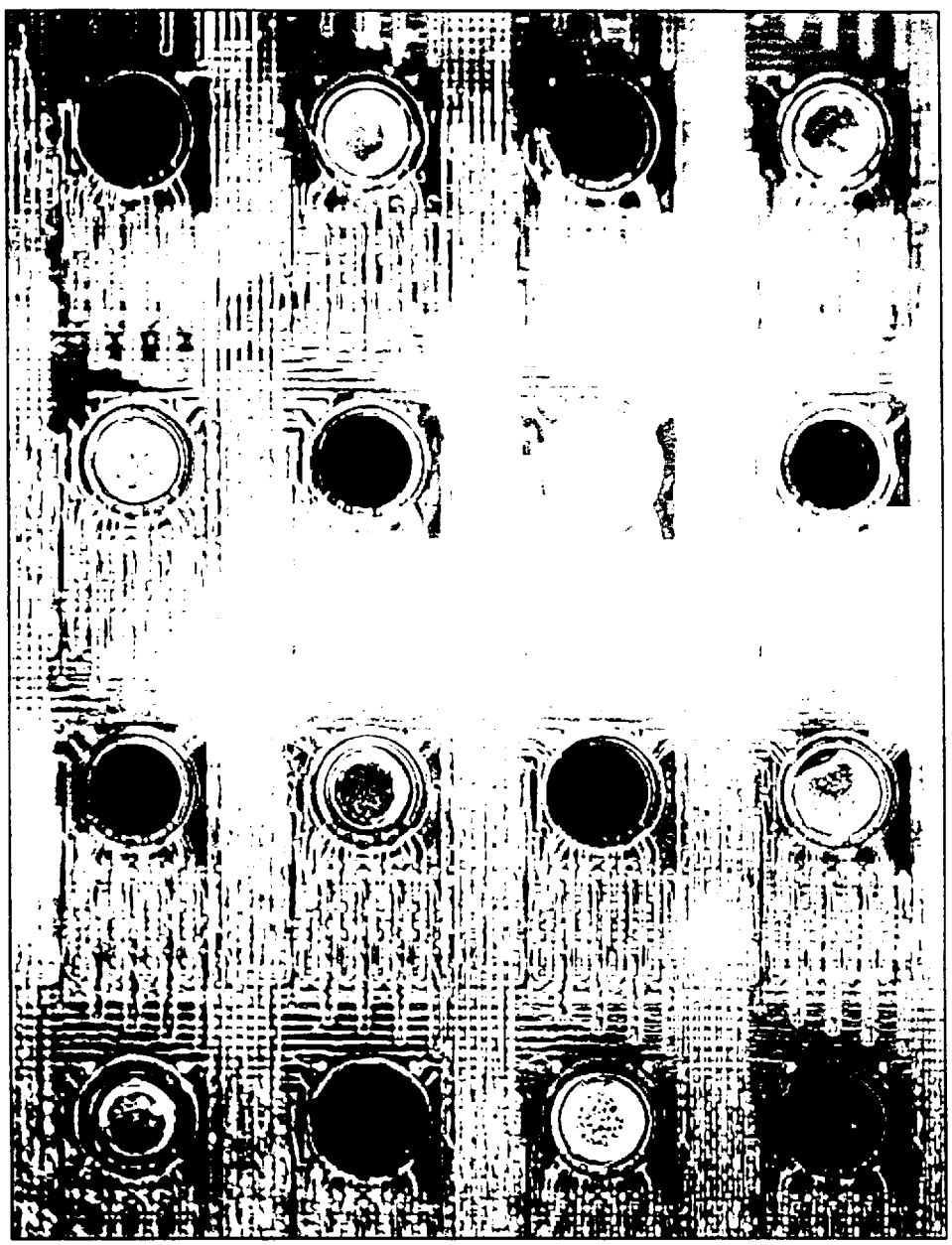
FIG. 21 represents a digitally captured epifluorescent photomicrograph showing the same hardwired electrode array chip as in FIG. 20, but this photomicrograph was taken using a 10 x objective with a 700 millisecond integration time.

Following drying of the chip, photomicrographs were taken of the electrode array following completion of the deprotection step, and are reproduced in FIGS. 20 and 21. As shown in these figures, selective deprotection was achieved using the process of the present invention. As is shown in these figures, a repeating checkerboard pattern was produced, exemplifying that the process of the present invention achieved localization of the protons generated at the anodes and prevented migration of these protons to the cathodes. The dark areas (anodes) are clearly defined and distinguished from the also clearly defined bright areas (cathodes). The clearly demarcated checkerboard pattern shown in the photomicrographs indicates that no, or very little, chemical cross talk occurred during the deprotection step.

Example 4

Comparative Example

Using two electrode array chips prepared in accordance with the present invention, one chip was processed using the selective deprotection procedure in accordance with the present invention using a buffering solution, and the second chip was processed using a selective deprotection procedure varying only in that the electrolyte used in the Examples of Southern (WO 93/22480, held Nov. 11, 1993) replaced the buffering solution of the present invention.

Rather than using an electrode array, this comparison was conducted on a few of the hard wired electrodes found on the side of the electrode array chips. FIG. 17 is a photomicrograph taken under the same conditions as FIG. 14, but showing the hard wired electrodes used in this example.

Deprotection in accordance with the invention

The steps of coating the chip with the polysaccharide membrane and attaching the trityl linker molecules to the membrane were performed in accordance with the procedures used above in Example 3.

The attaching of the fluorescent dye labeled streptavidin molecules and the deprotection steps were also performed in accordance with Example 3, but a 20 mM aqueous sodium phosphate buffer solution was used instead of the 0.05M solution used in Example 3, to enable the electrochemical generation of reagents. The voltage that was applied between selected electrodes was 2.8 volts, which was applied for approximately 30 seconds.

Similar results to Example 3 were obtained. These results are shown in FIGS. 22–24.

Figure 22:
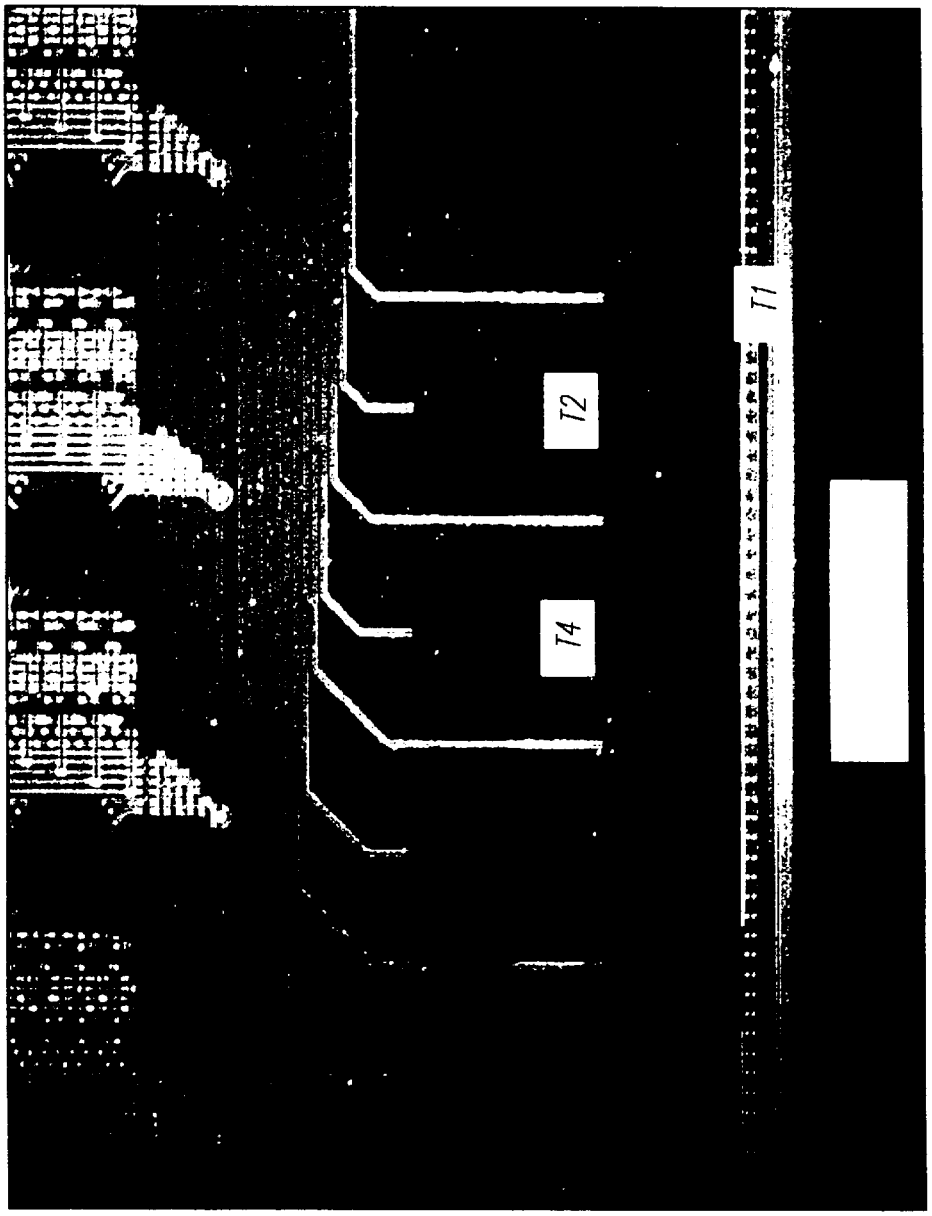
FIG. 22 is a digitally captured epifluorescent photomicrograph of an uncoated electrode array chip showing an array of hardwired electrodes. (The neighboring electrode array is also shown in this figure.) The orientation of the array shown allows accurate reading of the brightness of the electrodes. The electrodes shown are dark. The three electrodes to which electrical connection was provided, and of which brightness or darkness observations were made, are labeled "T1", "T2", and "T4".

FIG. 22 shows the hardwired electrodes involved in this process, labeled as T1, T2 and T4. In this process, T1 was the counter electrode, i.e., the cathode, and T2 and T4 were the anodes where protons were generated upon the application of the electric current or voltage. No voltage had been applied to the electrodes shown in FIG. 22.

Figure 23:
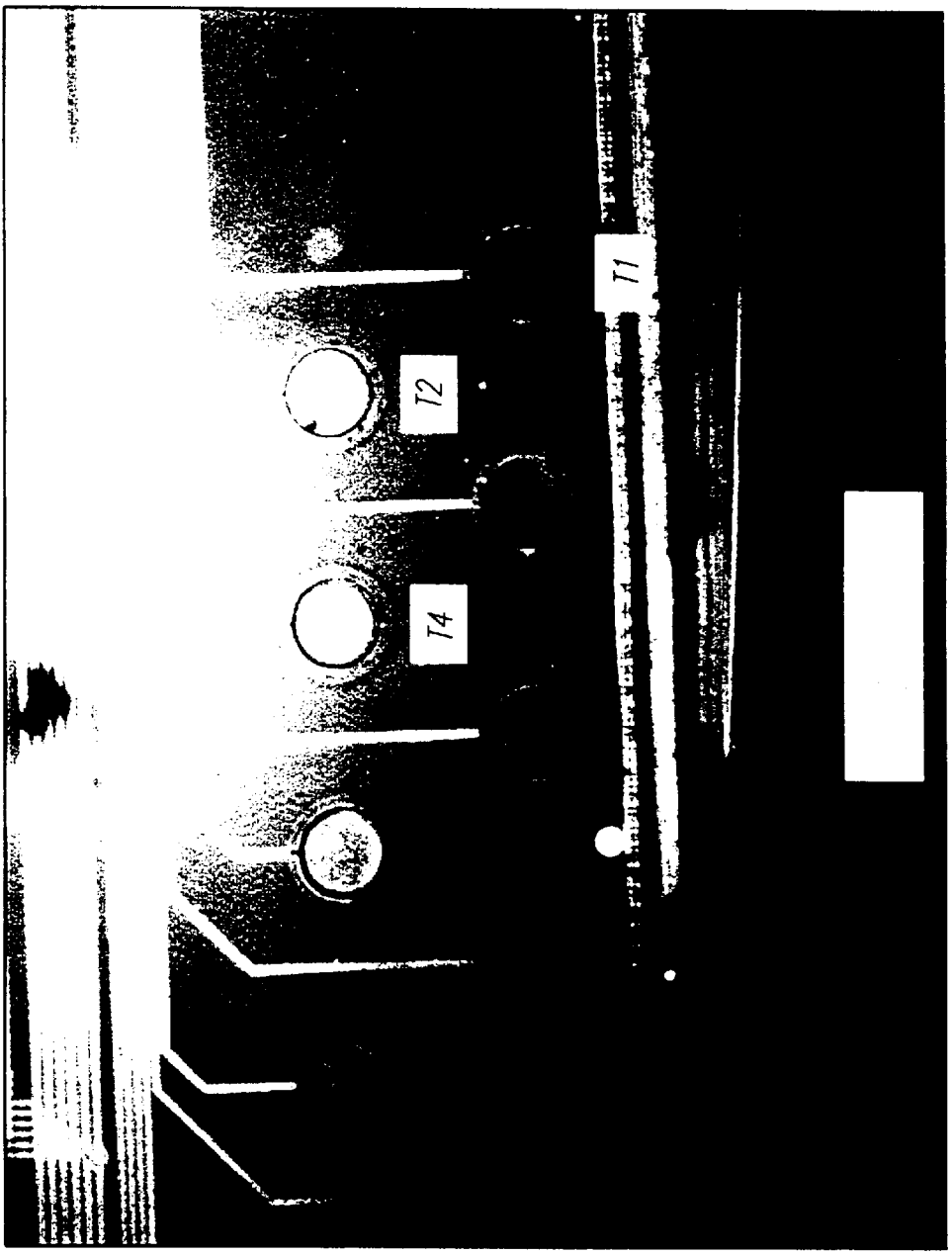
FIG. 23 is a digitally captured epifluorescent photomicrograph of a chip that is coated with a fluorescent membrane containing Texas Red labeled streptavidin molecules that are attached to the electrodes via trityl linker molecules. Electrodes T2 and T4 have a strong bright signal. Electrode T1 is dark. No voltage has been applied to the electrodes yet.

FIG. 23 shows the same electrodes following derivatization or bonding with the fluorescent labeled streptavidin molecules. As is shown, electrodes T2 and T4 are bright, indicating the presence of a Texas Red labeled streptavidin molecule bound to a linker molecule proximate each of these electrodes.

Figure 24:
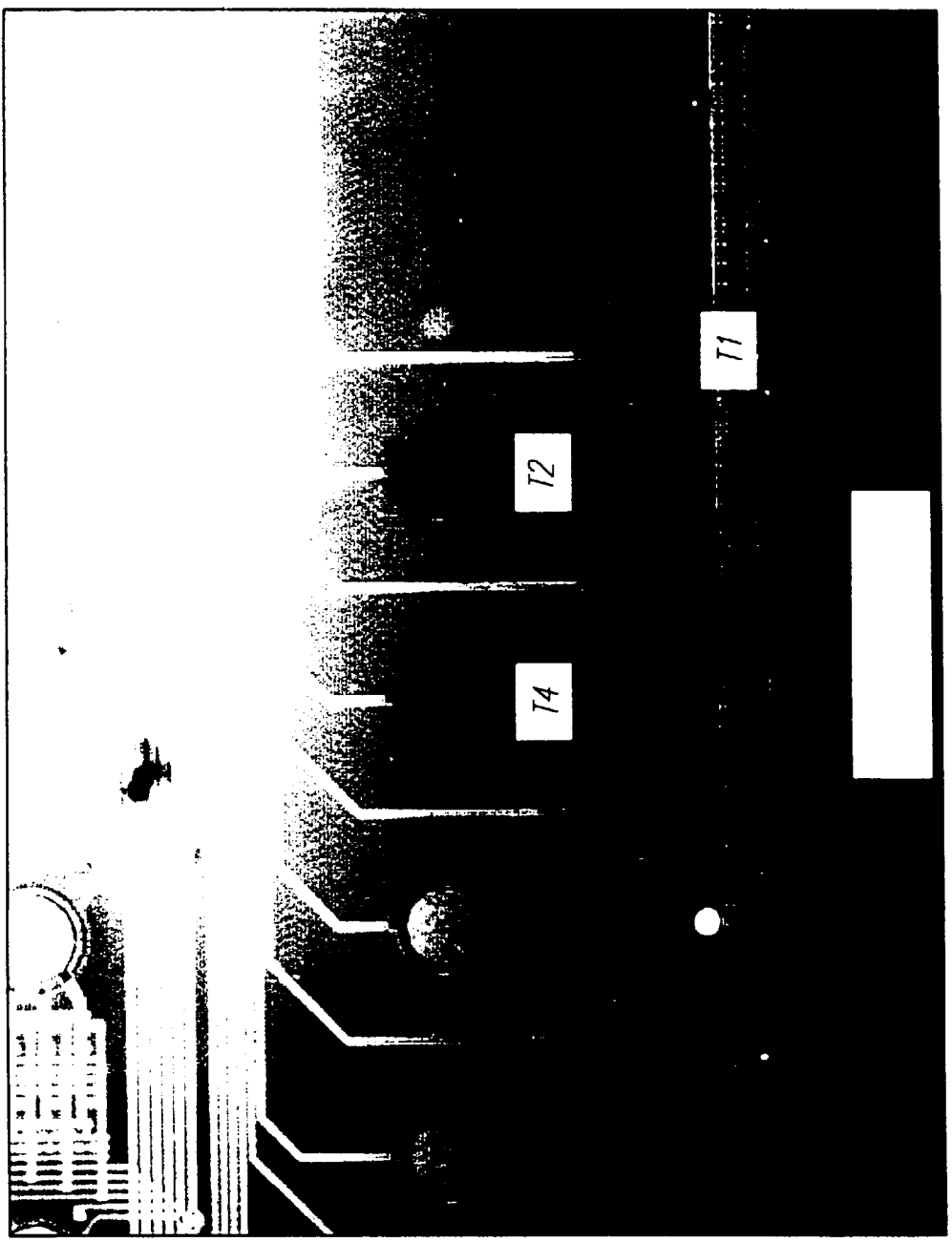
FIG. 24 is a digitally captured epifluorescent photomicrograph of the chip shown in FIG. 23 after positive voltage has been applied to electrodes T2 and T4. Positive voltage produced protons at these electrodes. Electrodes T2 and T4 are dark because the trityl linker molecule has dissociated from the membrane overlaying the electrodes. Electrode T1 was used as the counter electrode. Note that the dark areas are confined to electrodes T2 and T4, i.e., there is very little chemical cross talk occurring between neighboring electrodes.
Figure 25A:
FIGS. 25a and 25b represent digitally captured epifluorescent photomicrographs showing hardwired electrodes before (FIG. 25a) and after (FIG. 25b) a deprotection step performed in accordance with the reaction conditions, i.e., electrolyte, of the prior art, Southern WO 93/22480. These photomicrographs, taken through a 10 x objective, show the imprecision and randomness caused by "chemical crosstalk" between the electrodes. The large areas are black-out and white-out surrounding the electrodes in these photomicrographs represent the excursion of the electrochemical reagents (protons) away from the electrode at which they were generated.
Figure 25B:
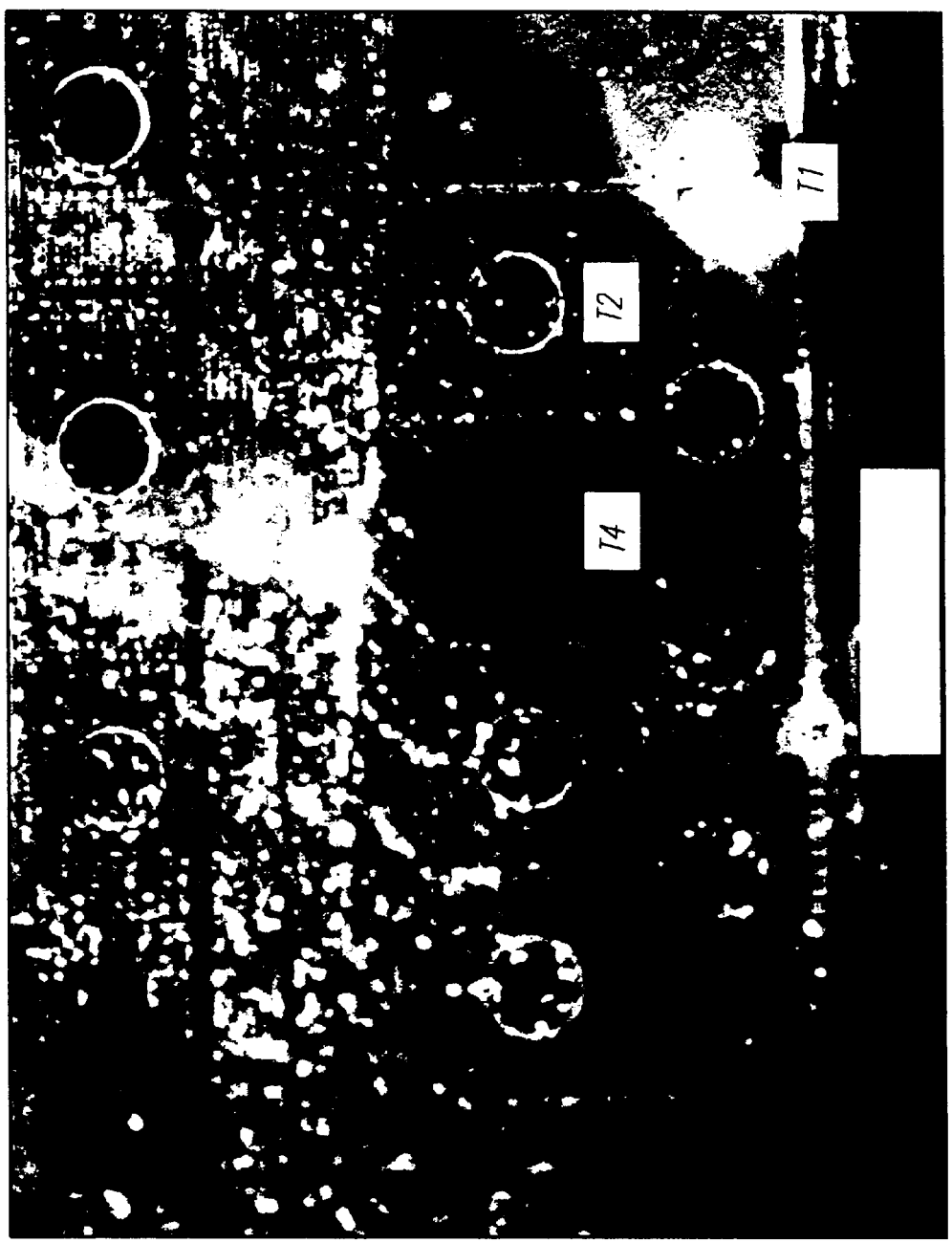
Figure 26A:
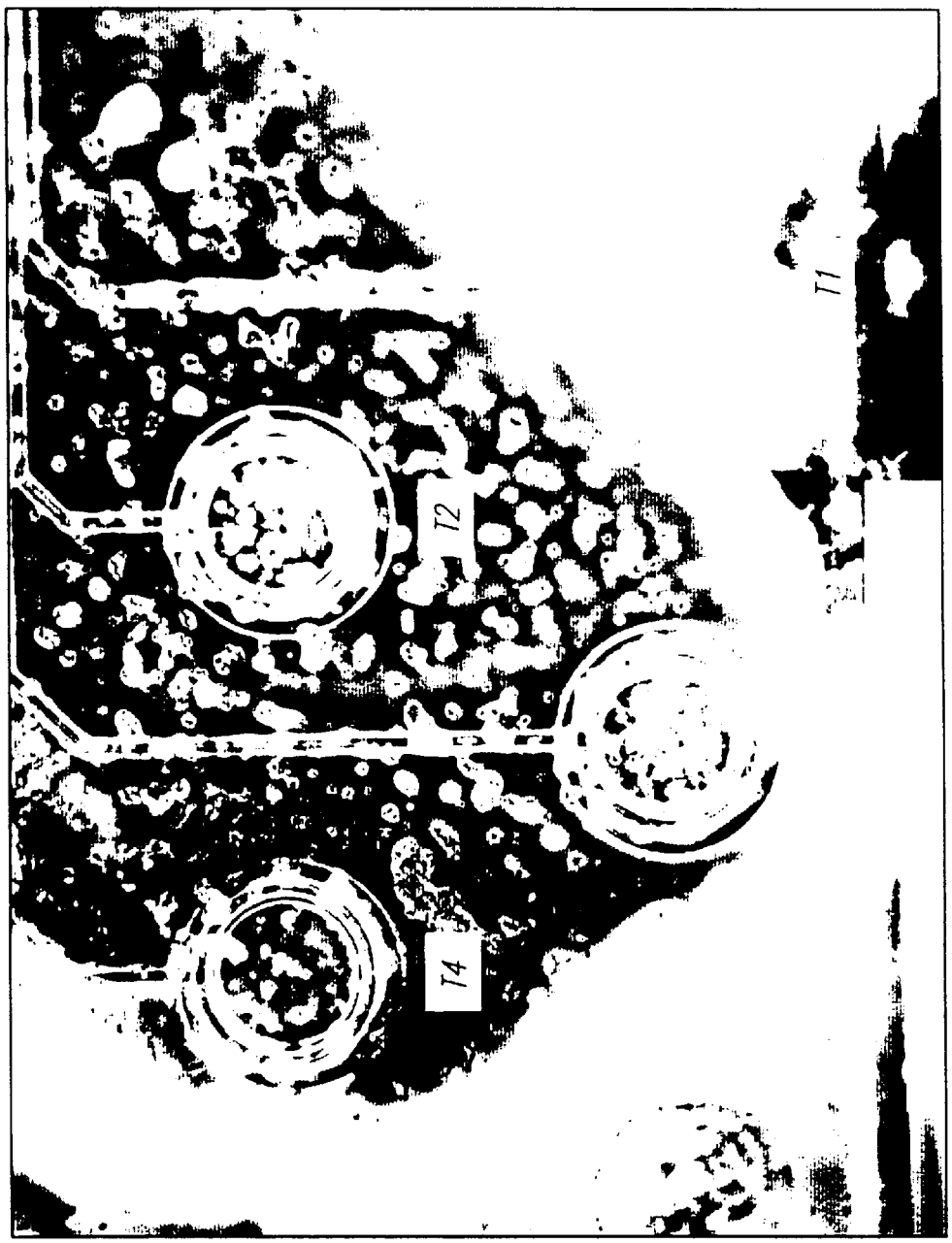
FIGS. 26a and 26b represent digitally captured epifluorescent photomicrographs taken through a 20 x objective with a 100 millisecond integration time of the same hardwired electrodes as shown in FIGS. 25a and 25b.
Figure 26B:
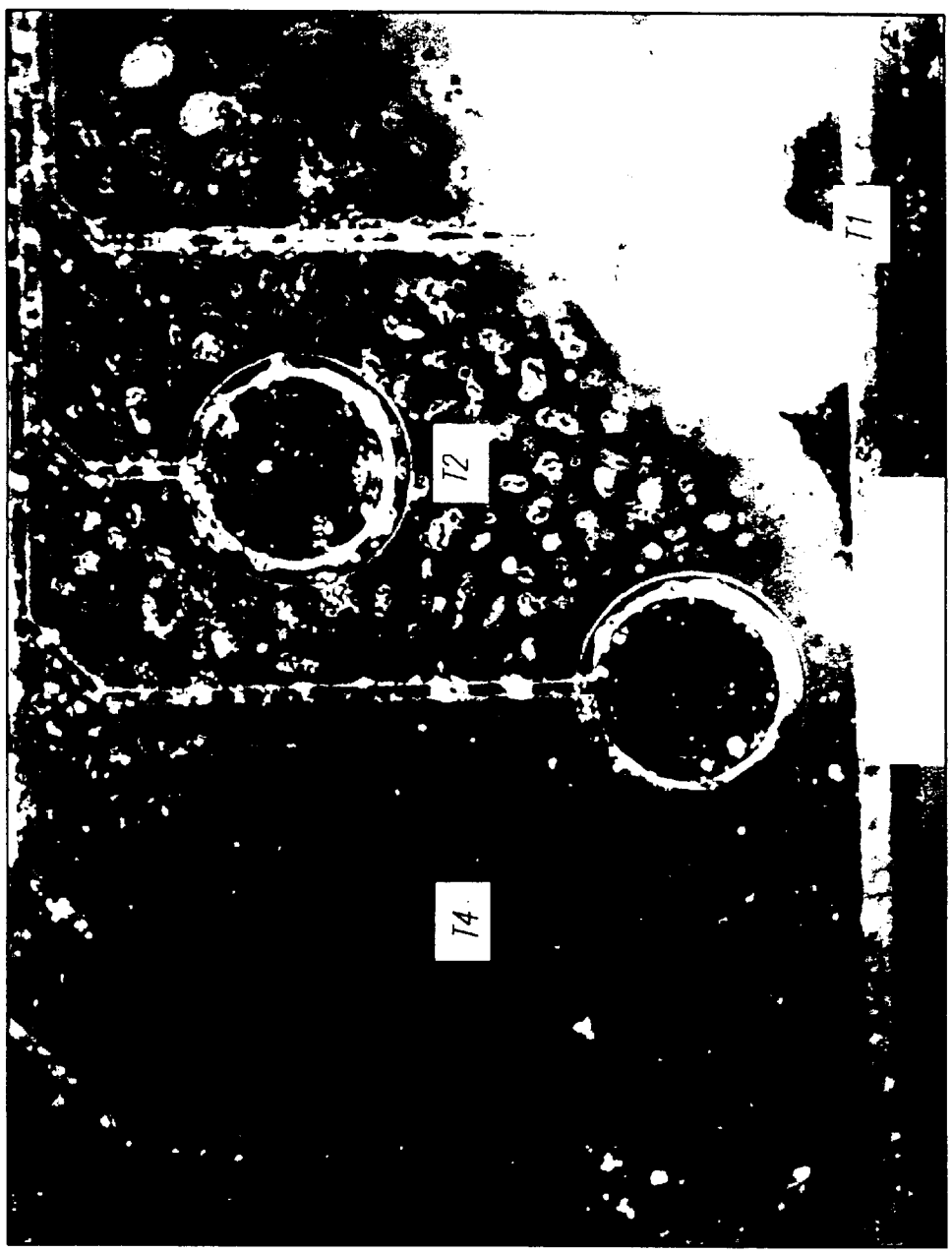

FIG. 24 shows the condition of anodes T2 and T4 following application of the voltage causing electrochemical generation of protons at the anodes and resultant dissociation of the trityl linker at these positions. Once dissociation occurred, the fluorescent labeled streptavidin molecules were washed away, leaving the anodes dark. Notably, anodes T2 and T4 are darker than the neighboring electrodes, indicating no chemical crosstalk was occurring.

As is shown by FIGS. 23 and 24, localization and selective deprotection were achieved at anodes T2 and T4, as was desired.

Deprotection using electrolyte of Southern (WO 93/24480)

All steps were performed identical to that for the above process in accordance with the present invention, except that instead of using a buffering solution in accordance with the invention, deprotection was performed in the presence of a 1% triethylammonium sulfate electrolyte in an acetonitrile solvent, as disclosed in the Examples of Southern.

The results of this process are shown in FIGS. 25a, 25b, 26a and 26b. In the electrodes shown, labeled T1 and T4, electrode T1 represented the cathode and electrode T4 represented the anode.

FIGS. 25a, 25b, 26a and 26b show that the membrane exhibited random and imprecise bright and dark areas. These bright and dark areas indicate that the protons generated at the anode (electrode T4) are not confined or localized to the area proximate the electrode, causing significant dissociation of the trityl linker over the entire field of the photomicrograph. T1 appears to have retained most of the fluorescence directly above the electrode. This is explained by the base that is generated at the T1 cathode, which neutralized the acid generated proximate the T4 anode.

As is seen from a comparison of the photomicrographs illustrating the results achieved in accordance with the present invention (i.e., using a buffering solution overlaying the electrodes) and those illustrating the results achieved from the analogous experiment performed using the electrolyte of Southern (WO 93/22480), superior localization of the electrochemical generated reagents was achieved using the process of the present invention. The superior localization achieved in accordance with the present invention greatly reduced, if not eliminated, undesirable chemical crosstalk between proximate electrodes. In contrast, very little localization of the electrochemical generated reagents was achieved using the electrolyte of the prior art, resulting in random and imprecise deprotection over the entire field of the micrograph.

Examples

Formation of Carbon-Carbon Bonds by Electrochemically-Catalyzed Olefin Addition Reactions Microscopy and chip control were performed according to the descriptions set forth in Examples 3 and 4 described above.

Electrode array chips comprising 16×64 platinum electrodes with thirteen ancillary hardwired electrodes were used in this example. Electrochemistry was conducted on a few of the hardwired electrodes found on the side of the array in this example. This example demonstrates the formation of carbon-carbon bonds by the method of this invention between an activated olefin immobilized proximate to one or a plurality of electrodes and an anhydride contained in a solution to which the one or a plurality of electrodes is exposed. The overlaying membrane was polysaccharide-based. The activated olefins were attached covalently to the overlaying membrane. More specifically, the activated olefins were acryloyl groups. The anhydride contained in the solution was a biotin anhydride.

An electrochemically activated catalyst was used to mediate the coupling of biotin to the immobilized olefins. More specifically vitamin $B_{12}$ was used as the catalyst. The active component of vitamin $B_{12}$ is +3 (Co(III)). Vitamin $B_{12}$ can be reduced electrochemically such that the formal oxidation state of the cobalt atom is +1(Co($\downarrow$)). The Co(I) species is active as a catalyst that mediates the formation of carbon-carbonbonds.

Experimental Procedure

Preparation of bulk acryloyl modified polysaccharide materials

Acryloyl groups were added to hydroxyl moieties on polysaccharides by the following procedure. A mixture of 0.2 g of the bulk polysaccharide, 0.05 g of acryloyl chloride (Aldich, Milwaukee, Wis.), 0.1 ml of pyridine (Alrich, Milwaukee, Wis.) in 5 ml of DMF (Aldrich, Milwaukee, Wis.) was stirred at room temperature for 30 minutes. The suspended polysaccharide was isolated by filtration. The acryloyl-modified polysaccharide was washed with DMF, then deionized water, and then acetone. The washed filter cake was dried in vacuo overnight at room temperature.

Preparation of biotin anhydride

A stirred suspension of 0.09 g of d-biotin (Sigma, St. Louis, Mo.) in 5 ml of dry THF (Aldrich, Milwaukee, Wis.) was degassed with dry nitrogen. 30 microliters of thionyl chloride (Aldrich, Milwaukee, Wis.) was added dropwise to the stirred suspension. The reaction mixture was stirred under nitrogen at room temperature for one hour. All of the suspended d-biotin went into solution upon reaction. The solvent was evaporated an the remaining solid material taken up in 5 ml of dry THF and filtered. The filtrate was added dropwise to a stirred suspension of 0.09 g of d-biotin and 44 microliters of triethyl amine in 5 ml of dry THF. The reaction mixture was stirred under nitrogen for one hour at room temperature. The contents were then filtered. The product biotin anhydride was isolated by removing the solvent from the filtrate.

Preparation of the chip for attachment of molecules

To enable the attachment of molecules by vitamin $B_{12}$ mediated carbon-carbon bond formation proximate to the surface of the electrode array chip, the chip was coated/modified with an overlaying membrane of a polysaccharide-based material. Specifically, a polygalactoside that was modified with acryloyl groups was used as overlaying membrane materials in this example. This membrane was applied by spin coating onto the chip.

Electrochemically mediated formation of carbon-carbon bonds between biotin and activated olefin groups A DMF solution that was 0.1 M in biotin anhydride, 0.37 mM in vitamin $B_{12}$ and 0.032M in tetrabutylammonium nitrate was prepared. A chip was immersed in the solution and a potential difference of 3.0 V was applied between the anode and the cathode for 5 minutes. This was repeated with different pairs of electrodes as needed. After the electrochemistry was completed, chips were removed from solution and washed with deionized water and acetone.

Assay with fluorescent dye labeled molecules

The electrochemically modified chip was immersed in an aqueous solution of fluorescent dye (Texas Red) labeled streptavidin molecules having a concentration of 50 micrograms per milliliter and allowed to remain in this solution for one hour. Fluorescent dye labeled streptavidin was obtained from Vector Laboratories (Burlingame, Calif.). During this immersion, biotin molecules attached to the membrane formed a complex with the fluorescent dye labeled streptavidin molecules.

The chip was then washed with an aqueous 0.1 M sodium phosphate buffer that was adjusted to pH 8.0 to remove dye labeled streptavidin that was not complexed with membrane bound biotin. The chip was now ready for evaluation by epifluorescent microscopy.

Results

Formation of carbon-carbon bond between acryloyl groups and biotin

A potential difference of 3.0 V was applied between hardwired electrodes $T_1$ and $T_2$ for 5 minutes. $T_1$ was the cathode and $T_2$ was the anode. Then, a 3.0 V potential difference was applied across hardwired electrodes $T_2$ and $T_4$. $T_4$ was the cathode and $T_2$ was the anode. Electrochemical reduction of vitamin $B_{12}$ occurred at the cathodes. The chip was then exposed to Texas Red labeled streptavidin as described and the photomicrograph of FIG. 27 was obtained. Bright spots at the cathodes indicate the presence of biotin bound to the overlaying membrane. Control experiments were performed to rule out the possibility of unanticipated artifacts causing a false positive.

Control Experiments

To demonstrate that the observed results were due to the formation of carbon-carbon bonds between biotin and an immobilized activated olefin the following control experiments were performed. The conditions used in the control experiments were identical to the conditions used for the carbon-carbon bond forming experiments.

Figure 27:
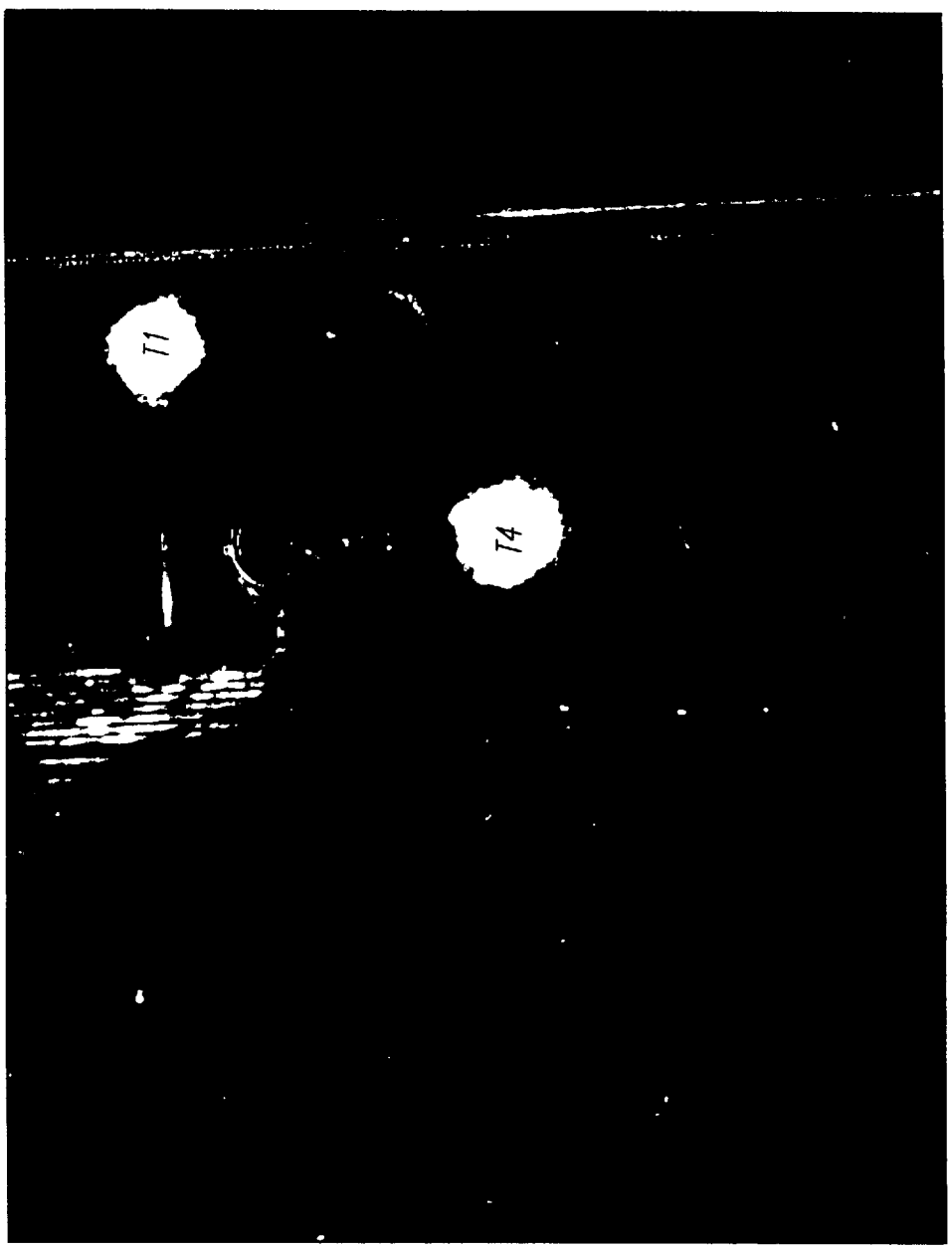
FIG. 27 represents electrochemical reduction of vitamin $B_{12}$ at the cathodes of electrode array chips described in Experiment 5. The chips were exposed to Texas Red labeled streptavidin and this photomicrograph was obtained. Bright spots at the cathodes indicate the presence of biotin bound to the overlaying membrane.
Figure 28:
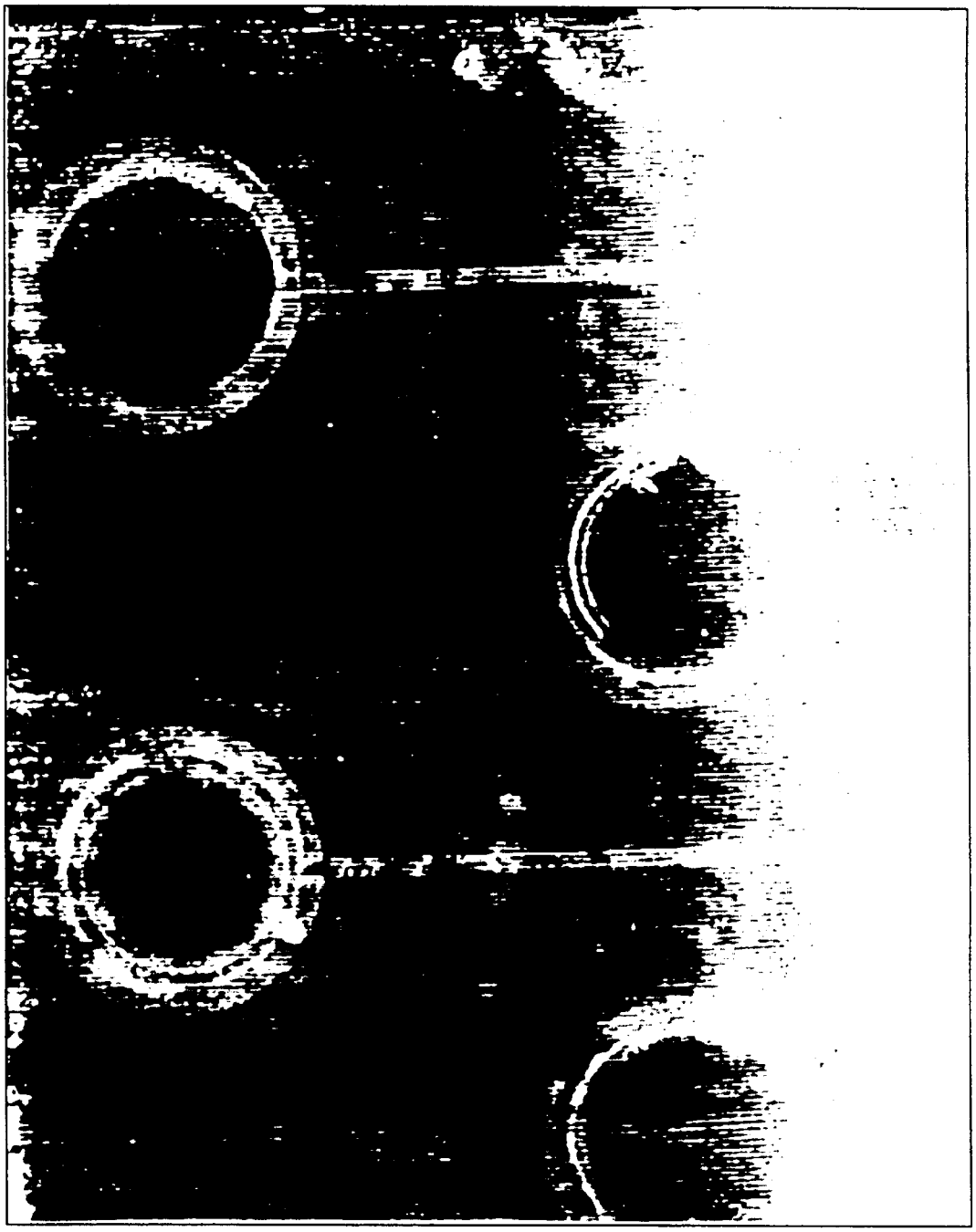
FIG. 28 confirms that the vitamin $B_{12}$ catalyst was necessary for the results depicted in FIG. 27. No vitamin $B_{12}$ was added to the solution and a voltage difference of 3.0 volts between the anode and the cathode was set. No observable current passed between the electrodes. At this potential difference, there are no electroactive species in solution without vitamin $B_{12}$. The chip was then exposed to Texas Red labeled streptavidin and washed. No evidence of carbon-carbon bond formation is seen.

A first control experiment was designed to confirm that the vitamin $B_{12}$ catalyst was necessary for the results obtained in FIG. 27. Chip was prepared with an acryloyl modified polysaccharide membrane as described. This chip was then immersed in a DMF solution identical to the DMF solution used to form carbon-carbon bonds, except that there was no vitamin $B_{12}$ added to the solution. A voltage difference of 3.0 volts between the anode and the cathode was set for 5 minutes. No observable current passed between the electrodes. At this potential difference, there are no electroactive species in solution without vitamin $B_{12}$. The first control chip was then exposed to Texas Red labeled streptavidin and washed in a procedure identical to the one outlined above. The results are shown in FIG. 28. No evidence of carbon-carbon bond formation is seen.

Figure 29:
FIG. 29 confirms that the biotin anhydride substrate was necessary to obtain the results depicted in FIG. 27. A chip was immersed in a DMF solution identical to the DMF solution used to form carbon-carbon bonds, except that there was no biotin anhydride added to the solution. A voltage difference of 3.0 volts between the anode and the cathode was set. The chip was then exposed to Texas Red labeled streptavidin and washed. No evidence of carbon-carbon bond formation is seen.

A second control experiment was designed to confirm that the biotin anhydride substrate was necessary to obtain the results of FIG. 27. A chip was prepared with an acryloyl modified polysaccharide membrane as described. The chip was then immersed in a DMF solution identical to the DMF solution used to form carbon-carbon bonds, except that there was no biotin anhydride added to the solution. A voltage difference of 3.0 volts between the anode and the cathode was set for 5 minutes. The second control chip was then exposed to Texas Red labeled streptavidin and washed in a procedure identical to the one outlined above. The results are shown in FIG. 29. No evidence of carbon-carbon bond formation is seen.

Figure 30:
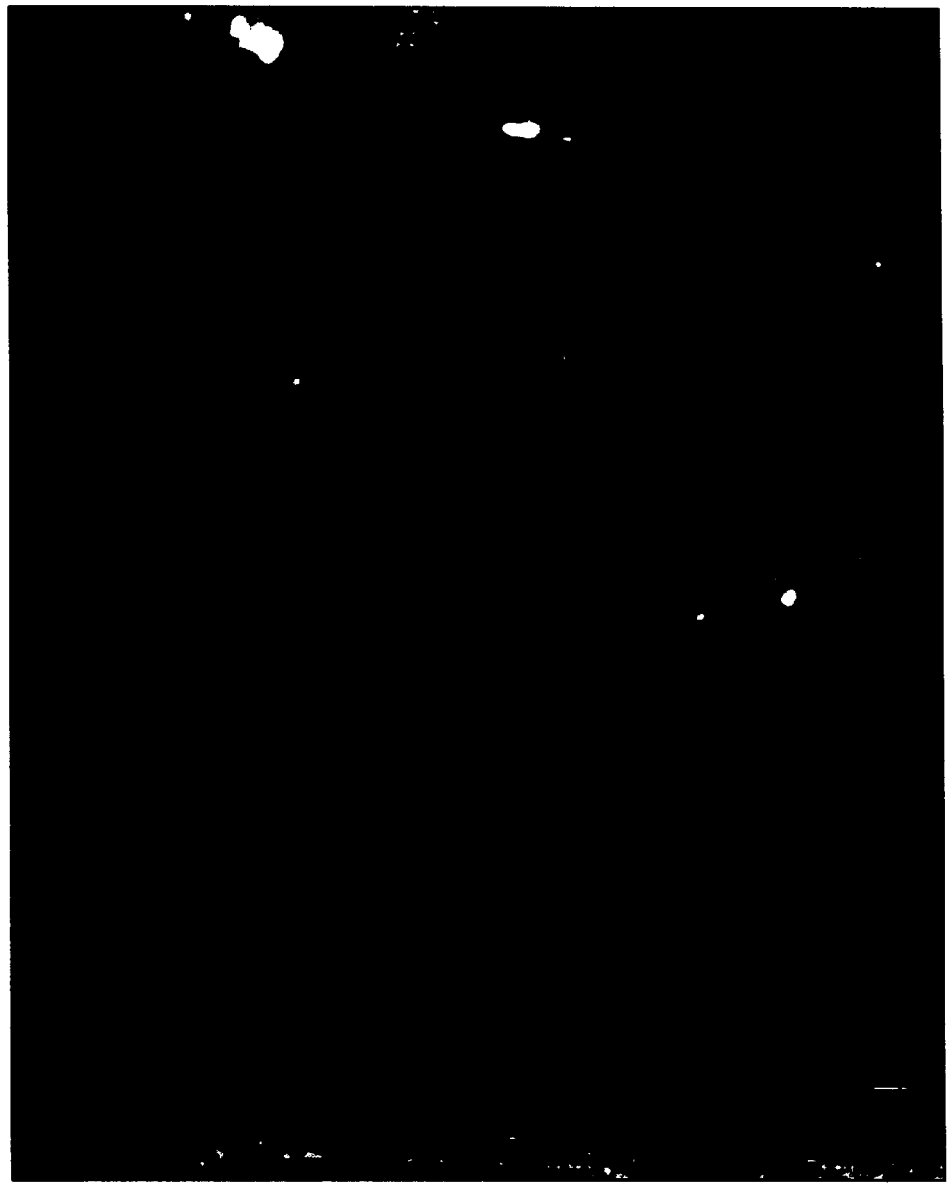
FIG. 30 confirms that the activated olefin was necessary to obtain the results depicted in FIG. 27. A chip was immersed in a DMF solution identical to the DMF solution used to form carbon-carbon bonds, except that there was no activated olefin attached to the overlaying membrane. A voltage difference of 3.0 volts between the anode and the cathode was set. The chip was then exposed to Texas Red labeled streptavidin and washed. No evidence of carbon-carbon bond formation is seen.

A third control experiment was designed to confirm that the activated olefin was necessary to obtain the results of FIG. 27. A chip was prepared with an unmodified polysaccharide membrane as described. The chip was then immersed in a DMF solution identical to the DMF solution used to form carbon-carbon bonds, except that there was no activated olefin attached to the overlaying membrane. A voltage difference of 3.0 volts between the anode and the cathode was set for 5 minutes. The third control chip was then exposed to Texas Red labeled streptavidin and washed in a procedure identical to the one outlined above. The results are shown in FIG. 30.

Example 6

Background

A major obstacle to exposing semiconductor devices to environments that contain ions is that the ions diffuse into the device. In particular, ions diffuse into regions of the device that have been doped with ions in a precise manner to impart particular electrical properties to these regions. An important example is the gate of a metal oxide semiconductor (MOS) transistor circuit element. Here either positive or negative ions (e.g., p-doped or n-doped) have been diffused into the gate region to make the region semiconducting. The threshold voltage and current-voltage characteristics of the transistor gate depend in a sensitive way on doping levels.

The long term reliability of many semiconductor devices depends on isolating them effectively from ionic contamination. The adhesives and encapsulants used in the semiconductor industry are treated to render the ion concentrations in these materials as low as possible, often less than pats per million.

Likewise, ion contamination represents a potential problem for utilizing devices comprising selected electrode(s) whose electrical activity is controlled by computer generated signalling because such devices would be immersed and operating in high concentration ionic solutions for extended period of time. As a result, it is desirable to incorporate structures into such that are designed both to monitor and to obviate ion contamination.

Such devices are designed to work by scavenging ions that diffuse into the device from the solutions to which they are exposed. These contaminating ions can be scavenged passively by reacting chemically with a material that is placed between them and the active circuitry. Alternatively, they can be scavenged actively by applying a voltage to an electrode that sets up an electric field that causes ions to migrate to the electrode and away from the active circuitry. We call these electrodes 'gettering' structures. Ion contamination can be monitored by placing transistor gates adjacent to the gettering electrodes and monitoring shifts in threshold voltage.

Figure 31:
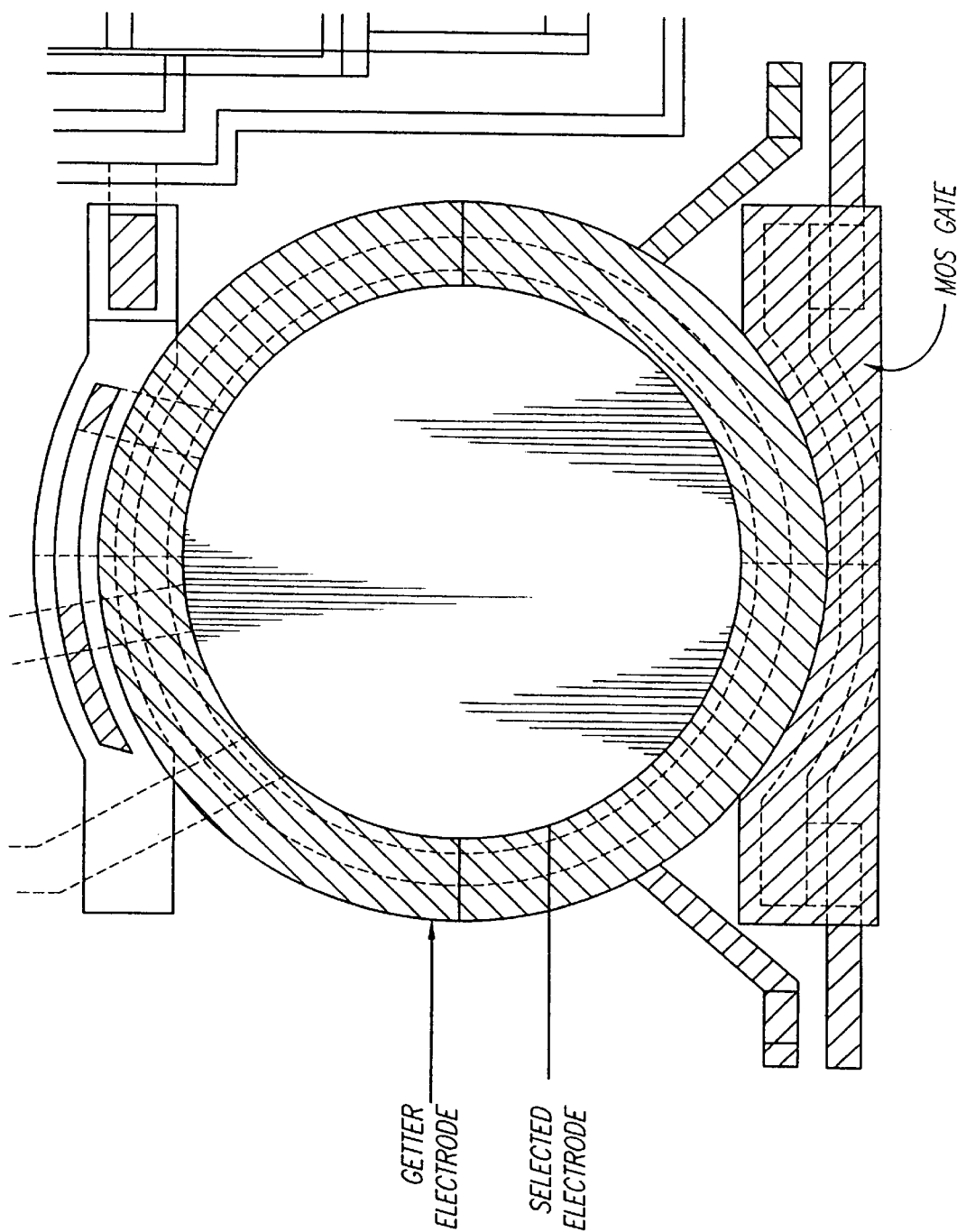
FIG. 31 depicts a transistor design representative of those used in electrode arrays in accordance with the present invention. A key feature is the placement of a "getter" structure which in this case is an electrode proximate to and in a ring around the selected electrode.
Figure 32:
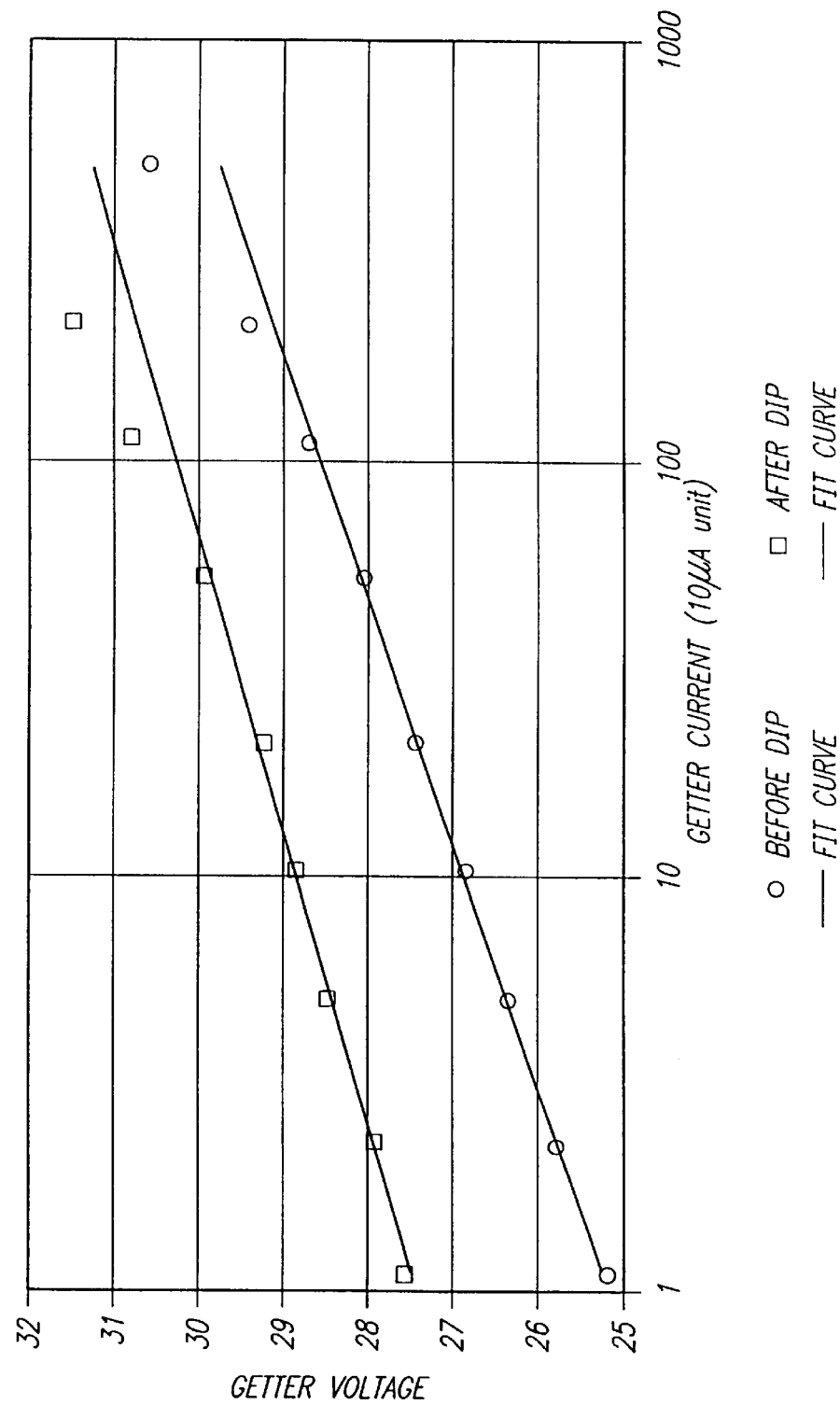
FIG. 32 demonstrates ionic contamination at the monitoring transistor when the chips were dipped into aqueous salt solutions. This illustrates the shift in the threshold voltage of the transistor monitoring device after a 20 minute exposure to a 0.1 M $NaPO_4$ solution. The measured data is fit to a subthreshold MOS curve of the form $V=Vo \ln(I/I_0)$.
Figure 36A:
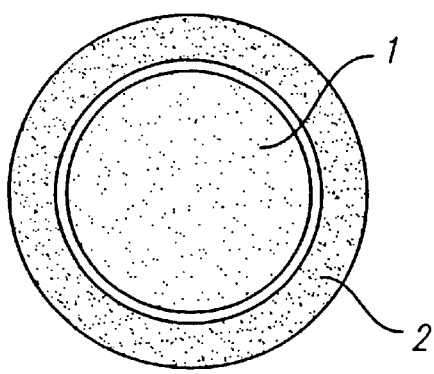
FIGS. 36a and 36b represent an exemplary selected electrode 1 useful according to the present invention having a "getter" structure 2 beneath the surface of the electrode. Such a configuration may be especially useful to control ion diffusion toward and into semiconductor circuitry.
Figure 35A:
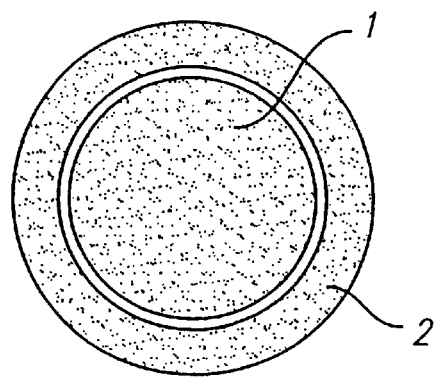
FIGS. 35a and 35b represent an exemplary selected electrode 1 useful according to the present invention having a "getter" structure 2 substantially exposed to the external environment. Such a configuration may be especially useful to control electrochemically generated reagents diffusing between electrodes in an array as well as ions diffusing toward and into semiconductor circuitry.
Figure 36B:
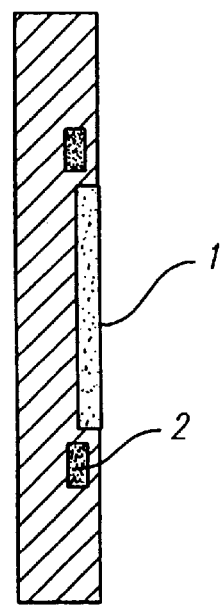
Figure 35B:
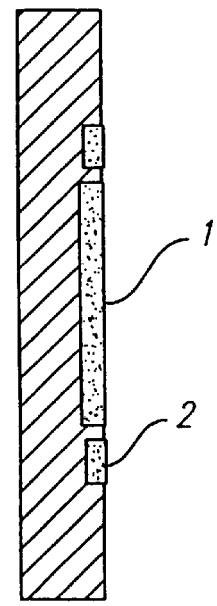

The time course of ionic contamination was monitored in such devices. To do this, a transistor using a ring getter electrode as a gate electrode was prepared. The MOS gate of this transistor was close to the electrochemical electrode. The MOS gate in this case is n-doped. The device was designed to allow getter voltages of up to 50 volts. The transistor design is illustrated in FIG. 31.

Results

Initial evaluation of the gettering device confirmed that there was ionic contamination at the monitoring transistor when the chips were dipped into aqueous salt solutions. FIG. 31 illustrates the shift in the threshold voltage of the transistor monitoring device after a 20 minute exposure to a 0.1 M $NaPO_4$ solution. The measured data is fit to a subthreshold MOS curve of the form $V=V_0 \ln(I/I_0)$.

Ions appear to contaminate the MOS gate of the monitoring transistor fairly quickly. The threshold voltage goes up, indicating that sodium ions are the primary contaminating species. The threshold voltage goes up because the conductivity of the MOS gate goes down. Since the MOS gate is n-doped, this means that positive sodium ions are, to some extent, neutralizing the negative ions that were used to dope the gate.

There is a secondary mode of contamination. It is possible that the surface layers of the chip are contaminated quickly, but the effects are not seen in the circuitry until much later. Because ions diffuse so slowly in the dielectric material of the chip, it may take some time before the ions in the surface contamination layer diffuse into the circuitry of the device. This was tested by immersing a chip for 20 minutes in an aqueous 0.1 M sodium phosphate solution. The chip was then removed from the solution, washed and dried. A getter electrode was set to 32 volts and the current monitored over time. The chip was not exposed to any solution after the initial 20 minute exposure. The results are shown in FIG. 33. The getter current continues to rise for several hours after the initial exposure to ions indicating a concomitant lowering in the threshold voltage of the gate. In other words, sodium ions are diffusing away from the gate region. The time course of the current rise follows an approximately logarithmic course for the first few hours. This is consistent with a self-screening diffusion process. Long term contamination is a problematic issue. Even though chips may seem fine after an initial exposure to salt solutions, they may fail later due to incipient surface contamination problems. Using a "getter" structure in accordance with the present invention effectively decreases such contamination.

What is claimed is:

1. A method for electrochemical placement of a material at a specific location on a porous substrate, which comprises the steps of:

providing a substrate having at its surface at least one electrode that is proximate to at least one molecule bearing at least one protected chemical functional group, placing a buffering solution in contact with the electrode and the porous substrate to prevent electrochemically generated reagents from leaving the locality of the electrode, wherein a buffering solution is one having the capacity to prevent pH changes upon addition of small amounts of acids or bases, applying a potential to said electrode sufficient to generate electrochemical reagents capable of deprotecting at least one of the protected chemical functional groups of said molecule, and bonding the deprotected chemical functional group with a monomer or a pre-formed molecule.

2. A method according to claim 1, further comprising placing a buffering or scavenging solution in contact with the electrode at the surface of the porous substrate to prevent the electrochemically generated reagents from leaving the locality of the electrode.

3. A method according to claim 2, wherein said buffering solution is selected from acetate buffers, borate buffers, carbonate buffers, citrate buffers, glycine buffers, HEPES buffers, MOPS buffers, phosphate buffers, RIS buffers and KI solutions.

4. A method according to claim 2, wherein said buffering solution is present in a concentration of at least 0.01 mM.

5. A method according to claim 1, wherein the concentration of the buffering solution ranges from 0.1 to 100 mM.

6. A method according to claim 1, wherein said monomer or preformed molecule has at least one other protected chemical functional groups at a site different from where bonding with the deprotected chemical functional group of the molecule occurs.

7. A method according to claim 1, wherein said monomer is an amino acid.

8. A method according to claim 1, wherein said pre-formed molecule is selected from proteins, nucleic acids, polysaccharides, and porphyrins.

9. A method according to claim 1, wherein said molecule is a linker molecule or a monomer.

10. A method according to claim 1, wherein said protected chemical functional groups are protected with an acid or base labile protecting group.

11. A method according to claim 1, wherein said at least one electrode comprises an array of electrodes.

12. A method according to claim 11, wherein said array of electrodes comprises at least 100 electrodes.

13. A method according to claim 6, further comprising sequentially deprotecting the other protected chemical functional group of the monomer or pre-formed molecule and bonding to the deprotected monomer or pre-formed molecule another monomer or pre-formed molecule.

14. A method for electrochemical synthesis of an array of separately formed polymers on a porous substrate, which comprises the steps of:

placing a buffering solution in contact with an array of electrodes that is proximate to a substrate surface, said surface being proximate to one of more molecules bearing at least one protected chemical functional group attached thereto, wherein a buffering solution is one having the capacity to prevent pH changes upon addition of small amounts of acids or bases;

selectively deprotecting at least one protected chemical functional group on at least one of said molecules;

bonding a first monomer having at least one protected chemical functional group to one or more deprotected chemical functional groups of aid molecule;

selectively deprotecting a chemical functional group on the bonded molecule or another of said molecules bearing at least one protected chemical functional group;

bonding a second monomer having at least one protected chemical functional group to a deprotected chemical functional group of the bonded molecule or said other deprotected molecule; and repeating the selective deprotection of a chemical functional group on a bonded protected monomer or a bonded protected molecule and the subsequent bonding of an additional monomer to said deprotected chemical functional group until at least two separate polymers of desired length are formed on the substrate surface.

15. A method according to claim 14, wherein during said selective deprotection steps, an electric potential is applied to one or more selected electrodes sufficient to generate electrochemical reagents at the selected electrodes capable of deprotecting the chemical functional groups on said proximate molecules or monomers.

16. A method according to claim 14, wherein said buffering solution prevents the electrochemical reagents generated at selected electrodes from deprotecting the chemical functional groups of molecules or monomers proximate to the unselected electrodes.

17. A method according to claim 14, wherein said buffering solution is selected from acetate buffers, borate buffers, carbonate buffers, citrate buffers, glycine buffers, HEPES buffers, MOPS buffers, phosphate buffers, TRIS buffers and KI solutions.

18. A method according to claim 14, wherein said buffering solution is present in a concentration of at least 0.01 mM.

19. A method according to claim 14, wherein the concentration of the buffering solution ranges from 0.1 to 100 mM.

20. A method according to claim 14, wherein said monomers are amino acids.

21. A method according to claim 14, wherein said molecules are linker molecules or monomers.

22. A method according to claim 21, wherein said linker molecule comprises a group cleavable by an electrochemically generated reagent, which cleavable group enables removal from said substrate of one or more bonded molecules.

23. A method according to claim 14, wherein said protected chemical functional groups are protected with an acid or base labile protecting group.

24. A method according to claim 14, wherein said substrate is formed from at least one material selected from undoped semiconductors, glass, ceramics, polymers, and waxes.

25. A method according to claim 14, wherein said array of electrodes comprises at least 100 electrodes.

26. A method according to claim 14, wherein said array of electrodes comprises a matrix having at least 2048 electrodes.

27. A method according to claim 26, wherein said array of electrodes comprises a matrix having at least 204,800 electrodes.

28. A method according to claim 14, wherein each of the electrodes in said array ranges in diameter from less than 1 micron to about 100 microns.

29. A method according to claim 14, wherein the electrodes of said array are formed from platinum or palladium.

30. A method according to claim 29, wherein said platinum or palladium electrodes are preloaded with hydrogen.

31. A method according to claim 18, which further comprises a capping step wherein unbonded deprotected chemical functional groups on said molecules or monomers are capped with acetic anhydride or n-methylimidizole.

32. A method according to claim 14, which further comprises an additional bonding step wherein a pre-formed molecule is bonded to a deprotected chemical functional group on one or more of said molecules or monomers.

33. A method according to claim 32, wherein said pre-formed molecule is selected from proteins, nucleic acids, polysaccharides, and porphyrins.

34. A method according to claim 32, wherein said pre-formed molecule bears at least one protected chemical functional group to which an additional monomer may bond following selective deprotection of the chemical functional group on the pre-formed molecule.

35. A method according to claim 15, wherein the one or more selected electrodes to which an electric potential is applied are selected by at a switching mechanism selected from CMOS switching circuitry, radio frequency addressable switches, microwave frequency addressable switches and light addressable switches.

36. A method according to claim 14, wherein said array of electrodes comprises at least 1024 electrodes.

37. A method for electrochemical synthesis of an array of separately formed oligonucleotides on a porous substrate, which comprises the steps of:

placing a buffering solution in contact with an array of electrodes that is proximate to a substrate surface, said surface being proximate to one of more molecules bearing at least one protected chemical functional group attached thereto, wherein a buffering solution is one having the capacity to prevent pH changes upon addition of small amounts of acids or bases;

selectively deprotecting at least one protected chemical functional group on at least one of said molecules;

bonding a first nucleotide having at least one protected chemical functional group;

bonding a second nucleotide having at least one protected chemical functional group to a deprotect chemical functional group of the nucleotide bonded molecule or said other deprotected molecule, and repeating the selective deprotection of a chemical functional group on a bonded protected nucleotide or a protected bonded molecule and the subsequent bonding of an additional nucleotide to said deprotected chemical functional group until at least two separate oligonucleotides of desired length are formed on the substrate surface.

38. A method according to claim 37, wherein during said selective deprotection steps, an electric potential is applied to one or more selected electrodes sufficient to generate electrochemical reagents at the selected electrodes capable of deprotecting the chemical functional groups on said proximate molecules or nucleic acids.

39. A method according to claim 37, wherein said buffering solution prevents the electrochemical reagents generated at selected electrodes from deprotecting the chemical functional groups or molecules or nucleotides proximate to unselected electrodes.

40. A method according to claim 8, wherein said preformed molecule is a nucleic acid.

41. A method for electrochemical placement of a material at a specific location on a porous substrate, which comprises the steps of:

providing a substrate having at its surface at least one electrode that is proximate to at least one molecule that is reactive with an electrochemically generated reagent, placing a substrate having at is surface at least one electrode that is proximate to at least one molecule that is reactive with an electrochemically generated reagent, and further placing a buffering solution in contact with the electrode and the porous substrate to prevent electrochemically generated reagents from leaving the locality of the electrode, wherein a buffering solution is one having the capacity to prevent pH changes upon addition of small amounts of acids or bases, applying a potential to said electrode sufficient to generate electrochemical reagents capable of reacting to the at least one molecule proximate to the electrode, and producing a chemical reaction thereby.

42. A method according to claim 41, wherein said buffering solution is selected from acetate buffers, borate buffers, carbonate buffers, citrate buffers, glycine buffers, HEPES buffers, MOPS buffers, phosphate buffers, TRIS buffers and KI solutions.

43. A method according to claim 41, wherein said buffering solution is present in a concentration of at least 0.01 mM.

44. A method according to claim 41, wherein the concentration of the buffering solution ranges from 0.1 to 100 mM.

* * * * *

(12) EX PARTE REEXAMINATION CERTIFICATE (6113th)
United States Patent
Montgomery

(10) Number: US 6,444,111 C1
(45) Certificate Issued: *Feb. 5, 2008

(54) ELECTROCHEMICAL SOLID PHASE SYNTHESIS OF POLYMERS

(75) Inventor: Donald D. Montgomery, Millbrae, CA (US)

(73) Assignee: Nanogen, Inc., San Diego, CA (US)

Reexamination Request:
No. 90/008,258, Oct. 4, 2006

Reexamination Certificate for:
Patent No.: 6,444,111
Issued: Sep. 3, 2002
Appl. No.: 09/416,860
Filed: Oct. 13, 1999

(*) Notice: This patent is subject to a terminal disclaimer.

Related U.S. Application Data

(63) Continuation of application No. 09/003,075, filed as application No. PCT/US97/11463 on Jul. 3, 1997, now Pat. No. 6,093,302.
(60) Provisional application No. 60/021,802, filed on Jul. 5, 1996.

(51) Int. Cl.
*B01J 19/00* (2006.01)
*C07K 1/04* (2006.01)
*C07K 1/00* (2006.01)

(52) U.S. Cl. .............. 205/334; 205/687; 205/688
(58) Field of Classification Search ............... None
See application file for complete search history.

(56) References Cited

U.S. PATENT DOCUMENTS

| 5,210,075 A | * | 5/1993 | Scholz et al. ............... 514/14 |
| 5,492,892 A | * | 2/1996 | Andersen et al. ........... 514/13 |
| 5,667,667 A | * | 9/1997 | Southern .................... 205/687 |
| 5,929,208 A |   | 7/1999 | Heller et al. ............... 530/333 |

OTHER PUBLICATIONS

Dube et al, "Electrocatalytic hydrogenation of cyclohexanone: Simple dynamic cell design," Journal of Applied Electrochemistry, vol. 33, pp. 541–547 (2003).*
Lofrano et al, "Electrocatalytic hydrogenation of carbonylic compounds using an electrode with platinum particles dispersed in films of poly–[allyl ether p–(2–aminoethyl) phenol] co–polymerized with allyl phenyl ether," Journal of Molecular Catalysis A: Chemical 218, pp. 73–79 (2004).*
Casadei et al., "A Selective Electrocatalytic Cleavage of the Benzyloxycarbonyl Group from Peptides," *Synthesis*, 1987, 1118–1119.
Couper et al., "Electrode materials for electrosynthesis," *Chem. Rev.*, 1990, 90(5), 837–865.

* cited by examiner

*Primary Examiner*—Alan Diamond

(57) ABSTRACT

A solid phase synthesis method for the preparation of diverse sequences of separate polymers or nucleic acid sequences using electrochemical placement of monomers of nucleic acids at a specific location on a substrate containing at least one electrode that is preferably in contact with a buffering or scavenging solution to prevent chemical crosstalk between electrodes due to diffusion of electrochemically generated reagents.

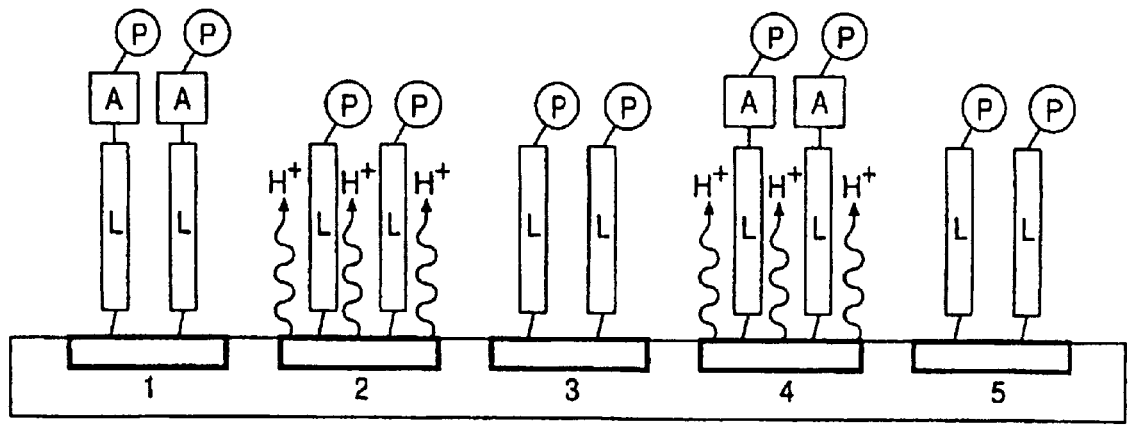

US 6,444,111 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–13 and 40–44 is confirmed.

Claims 14, 15, 37 and 38 are determined to be patentable as amended.

Claims 16–36 and 39, dependent on an amended claim, are determined to be patentable.

14. A method for electrochemical synthesis of an array of separately formed polymers on a porous substrate, which comprises the steps of:

placing a buffering solution in contact with an array of electrodes that is proximate to a substrate surface, said surface being proximate to one of more molecules bearing at least one protected chemical functional group attached thereto, wherein a buffering solution is one having the capacity to prevent pH changes upon addition of small amounts of acids or bases;

selectively deprotecting at least one protected chemical functional group on at least one of said molecules;

bonding a first monomer having at least one protected chemical functional group to one or more deprotected chemical functional groups of aid molecule;

selectively deprotecting a chemical functional group on the bonded molecule or another of said molecules bearing at least one protected chemical functional group;

bonding a second monomer having at least one protected chemical functional group to a deprotected chemical functional group of the bonded molecule or said other deprotected molecule; and repeating the selective deprotection of a chemical functional group on a bonded protected monomer or a bonded protected molecule and the subsequent bonding of an additional monomer to said deprotected chemical functional group until at least two separate polymers of desired length are formed on the substrate surface, *wherein during said selective deprotection steps, an electric potential is applied to one or more selected electrodes sufficient to generate electrochemical reagents at the selected electrodes capable of deprotecting the chemical functional groups on said proximate molecules or monomers.*

15. A method according to claim 14, wherein [during said selective deprotection steps, an electric potential is applied to one or more selected electrodes sufficient to generate electrochemical reagents at the selected electrodes capable of deprotecting the chemical functional groups on said proximate molecules or monomers] *said electrochemical reagents are selected from the group consisting of acidic reagents and basic reagents.*

37. A method for electrochemical synthesis of an array of separately formed oligonucleotides on a porous substrate, which comprises the steps of:

placing a buffering solution in contact with an array of electrodes that is proximate to a substrate surface, said surface being proximate to one of more molecules bearing at least one protected chemical functional group attached thereto, wherein a buffering solution is one having the capacity to prevent pH chances upon addition of small amounts of acids or bases;

selectively deprotecting at least one protected chemical functional group on at least one of said molecules;

bonding a first nucleotide having at least one protected chemical functional group;

bonding a second nucleotide having at least one protected chemical functional group to a deprotect chemical functional group of the nucleotide bonded molecule or said other deprotected molecule[.]; *and* repeating the selective deprotection of a chemical functional group on a bonded protected nucleotide or a protected bonded molecule and the subsequent bonding of an additional nucleotide to said deprotected chemical functional group until at least two separate oligonucleotides of desired length are formed on the substrate surface, *wherein during said selective deprotection steps, an electric potential is applied to one or more selected electrodes sufficient to generate electrochemical reagents at the selected electrodes capable of deprotecting the chemical functional groups on said proximate molecules or nucleic acids.*

38. A method according to claim 37, wherein [during said selective deprotection steps, an electric potential is applied to one or more selected electrodes sufficient to generate electrochemical reagents at the selected electrodes capable of deprotecting the chemical functional groups on said proximate molecules or nucleic acids] *said electrochemical reagents are selected from the group consisting of acidic reagents and basic reagents.*

\* \* \* \* \*